(12) United States Patent
Saliman et al.

(10) Patent No.: US 9,700,299 B2
(45) Date of Patent: Jul. 11, 2017

(54) SUTURE PASSER DEVICES AND METHODS

(75) Inventors: Justin D. Saliman, Los Angeles, CA (US); John G. McCutcheon, Menlo Park, CA (US); Christopher P. Bender, Oakland, CA (US); Mark Y. Hirotsuka, San Jose, CA (US); Michael Murillo, Menlo Park, CA (US); Michael J. Hendricksen, Redwood City, CA (US)

(73) Assignee: CETERIX ORTHOPAEDICS, INC., Fremont, CA (US)

( * ) Notice: Subject to any disclaimer, the term of this patent is extended or adjusted under 35 U.S.C. 154(b) by 0 days.

(21) Appl. No.: 13/323,391

(22) Filed: Dec. 12, 2011

(65) Prior Publication Data

US 2012/0283753 A1 Nov. 8, 2012

Related U.S. Application Data

(60) Provisional application No. 61/483,200, filed on May 6, 2011, provisional application No. 61/511,922, filed on Jul. 26, 2011.

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/062* (2013.01);
(Continued)

(58) Field of Classification Search
CPC ............ A61B 17/0469; A61B 17/0482; A61B 17/0485; A61B 17/062; A61B 2017/0496;
(Continued)

(56) References Cited

U.S. PATENT DOCUMENTS

| 1,037,864 A | 9/1912 | Carlson et al. |
| 1,815,725 A | 7/1931 | Pilling et al. |

(Continued)

FOREIGN PATENT DOCUMENTS

| CN | 201263696 Y | 7/2009 |
| CN | 101961256 A | 2/2011 |

(Continued)

OTHER PUBLICATIONS

Saliman et al.; U.S. Appl. No. 13/247,892 entitled "Meniscus Repair," filed Sep. 28, 2011.

(Continued)

*Primary Examiner* — Jing Ou
(74) *Attorney, Agent, or Firm* — Shay Glenn LLP

(57) ABSTRACT

Devices, systems and methods for passing a suture. In general, described herein are suturing devices, such as suture passers, as well as methods of suturing tissue. These suture passing devices are dual deployment suture passers in which a first distal jaw member is moveable at an angle with respect to the longitudinal axis of the elongate body of the device and the second distal jaw member is retractable proximally to the distal end region of the elongate body and/or the first jaw member. Methods of suturing tissue using a dual deployment suture passer are also described.

29 Claims, 54 Drawing Sheets

(51) Int. Cl.
*A61B 17/06* (2006.01)
*A61B 17/29* (2006.01)

(52) U.S. Cl.
CPC ....... *A61B 17/0485* (2013.01); *A61B 17/0625* (2013.01); *A61B 2017/0472* (2013.01); *A61B 2017/0496* (2013.01); *A61B 2017/06009* (2013.01); *A61B 2017/06014* (2013.01); *A61B 2017/06042* (2013.01); *A61B 2017/06176* (2013.01); *A61B 2017/2927* (2013.01)

(58) Field of Classification Search
CPC ........... A61B 2017/06176; A61B 2017/06014; A61B 17/0625; A61B 2017/0472; A61B 2017/2927; A61B 2017/06009; A61B 2017/06042
USPC ........ 606/139, 144–148, 153, 205–208, 223, 606/225, 226, 232, 51; 289/17
See application file for complete search history.

(56) References Cited

U.S. PATENT DOCUMENTS

| | | | |
|---|---|---|---|
| 2,738,790 A | 3/1956 | Todt, Sr. et al. | |
| 2,748,773 A | 6/1956 | Vacheresse, Jr. | |
| 3,470,875 A | 10/1969 | Johnson | |
| 3,580,256 A | 5/1971 | Wilkinson et al. | |
| 3,807,407 A | 4/1974 | Schweizer | |
| 3,842,840 A | 10/1974 | Schweizer | |
| 3,901,244 A | 8/1975 | Schweizer | |
| 4,021,896 A | 5/1977 | Stierlein | |
| 4,109,658 A | 8/1978 | Hughes | |
| 4,164,225 A | 8/1979 | Johnson et al. | |
| 4,236,470 A | 12/1980 | Stenson | |
| 4,345,601 A | 8/1982 | Fukuda | |
| 4,440,171 A | 4/1984 | Nomoto et al. | |
| 4,484,580 A | 11/1984 | Nomoto et al. | |
| 4,553,543 A | 11/1985 | Amarasinghe | |
| 4,605,002 A | 8/1986 | Rebuffat | |
| 4,621,640 A | 11/1986 | Mulhollan et al. | |
| 4,706,666 A | 11/1987 | Sheets | |
| 4,836,205 A * | 6/1989 | Barrett | 606/144 |
| 4,923,461 A * | 5/1990 | Caspari et al. | 606/146 |
| 4,957,498 A | 9/1990 | Caspari et al. | |
| 4,981,149 A | 1/1991 | Yoon et al. | |
| 5,002,561 A | 3/1991 | Fisher | |
| 5,011,491 A | 4/1991 | Boenko et al. | |
| 5,037,433 A | 8/1991 | Wilk et al. | |
| 5,059,201 A | 10/1991 | Asnis | |
| 5,112,344 A | 5/1992 | Petros | |
| 5,129,912 A | 7/1992 | Noda et al. | |
| 5,139,520 A | 8/1992 | Rosenberg | |
| 5,156,608 A | 10/1992 | Troidl et al. | |
| 5,193,473 A | 3/1993 | Asao et al. | |
| 5,211,650 A | 5/1993 | Noda | |
| 5,219,358 A | 6/1993 | Bendel et al. | |
| 5,222,962 A | 6/1993 | Burkhart | |
| 5,250,053 A | 10/1993 | Snyder | |
| 5,250,055 A | 10/1993 | Moore et al. | |
| 5,254,126 A | 10/1993 | Filipi et al. | |
| 5,281,237 A | 1/1994 | Gimpelson | |
| 5,312,422 A | 5/1994 | Trott | |
| 5,330,488 A | 7/1994 | Goldrath | |
| 5,336,229 A | 8/1994 | Noda | |
| 5,342,389 A * | 8/1994 | Haber et al. | 606/205 |
| 5,364,410 A | 11/1994 | Failla et al. | |
| 5,368,601 A | 11/1994 | Sauer et al. | |
| 5,389,103 A | 2/1995 | Melzer et al. | |
| 5,391,174 A | 2/1995 | Weston | |
| 5,397,325 A | 3/1995 | Della Badia et al. | |
| 5,403,328 A | 4/1995 | Shallman | |
| 5,405,352 A | 4/1995 | Weston | |
| 5,405,532 A | 4/1995 | Loew et al. | |
| 5,431,666 A | 7/1995 | Sauer et al. | |
| 5,437,681 A | 8/1995 | Meade et al. | |
| 5,454,823 A | 10/1995 | Richardson et al. | |
| 5,454,834 A | 10/1995 | Boebel et al. | |
| 5,468,251 A * | 11/1995 | Buelna | 606/223 |
| 5,474,057 A | 12/1995 | Makower et al. | |
| 5,478,344 A | 12/1995 | Stone et al. | |
| 5,478,345 A | 12/1995 | Stone et al. | |
| 5,480,406 A | 1/1996 | Nolan et al. | |
| 5,496,335 A | 3/1996 | Thomason et al. | |
| 5,499,991 A * | 3/1996 | Garman et al. | 606/148 |
| 5,507,757 A | 4/1996 | Sauer et al. | |
| 5,520,702 A | 5/1996 | Sauer et al. | |
| 5,522,820 A | 6/1996 | Caspari et al. | |
| 5,540,704 A | 7/1996 | Gordon et al. | |
| 5,540,705 A | 7/1996 | Meade et al. | |
| 5,562,686 A | 10/1996 | Sauer et al. | |
| 5,569,301 A | 10/1996 | Granger et al. | |
| 5,571,090 A | 11/1996 | Sherts | |
| 5,571,119 A | 11/1996 | Atala | |
| 5,575,800 A | 11/1996 | Gordon | |
| 5,578,044 A | 11/1996 | Gordon et al. | |
| 5,607,435 A | 3/1997 | Sachdeva et al. | |
| 5,616,131 A | 4/1997 | Sauer et al. | |
| 5,618,290 A | 4/1997 | Toy et al. | |
| 5,626,588 A | 5/1997 | Sauer et al. | |
| 5,632,751 A | 5/1997 | Piraka | |
| 5,643,289 A | 7/1997 | Sauer et al. | |
| 5,645,552 A | 7/1997 | Sherts | |
| 5,653,716 A | 8/1997 | Malo et al. | |
| 5,665,096 A | 9/1997 | Yoon | |
| 5,669,917 A | 9/1997 | Sauer et al. | |
| 5,674,229 A | 10/1997 | Tovey et al. | |
| 5,674,230 A | 10/1997 | Tovey et al. | |
| 5,681,331 A | 10/1997 | de la Torre et al. | |
| 5,690,652 A | 11/1997 | Wurster et al. | |
| 5,690,653 A * | 11/1997 | Richardson et al. | 606/148 |
| 5,709,708 A | 1/1998 | Thal | |
| 5,713,910 A | 2/1998 | Gordon et al. | |
| 5,728,107 A | 3/1998 | Zlock et al. | |
| 5,728,113 A | 3/1998 | Sherts | |
| 5,730,747 A | 3/1998 | Ek et al. | |
| 5,741,278 A * | 4/1998 | Stevens | 606/144 |
| 5,749,879 A * | 5/1998 | Middleman et al. | 606/139 |
| 5,755,728 A | 5/1998 | Maki | |
| 5,759,188 A | 6/1998 | Yoon | |
| 5,766,183 A | 6/1998 | Sauer | |
| 5,792,153 A | 8/1998 | Swain et al. | |
| 5,800,445 A | 9/1998 | Ratcliff et al. | |
| 5,814,054 A | 9/1998 | Kortenbach et al. | |
| 5,814,069 A | 9/1998 | Schulze et al. | |
| 5,824,009 A | 10/1998 | Fukuda et al. | |
| 5,827,300 A | 10/1998 | Fleega | |
| 5,843,100 A | 12/1998 | Meade | |
| 5,843,126 A | 12/1998 | Jameel | |
| 5,865,836 A | 2/1999 | Miller | |
| 5,871,490 A | 2/1999 | Schulze et al. | |
| 5,876,411 A | 3/1999 | Kontos | |
| 5,876,412 A | 3/1999 | Piraka | |
| 5,895,393 A | 4/1999 | Pagedas | |
| 5,895,395 A | 4/1999 | Yeung | |
| 5,897,563 A | 4/1999 | Yoon et al. | |
| 5,899,911 A | 5/1999 | Carter | |
| 5,899,920 A | 5/1999 | DeSatnick et al. | |
| 5,906,630 A | 5/1999 | Anderhub et al. | |
| 5,908,428 A | 6/1999 | Scirica et al. | |
| 5,910,148 A | 6/1999 | Reimels et al. | |
| 5,935,138 A | 8/1999 | McJames, II et al. | |
| 5,938,668 A | 8/1999 | Scirica et al. | |
| 5,944,739 A | 8/1999 | Zlock et al. | |
| 5,947,982 A | 9/1999 | Duran | |
| 5,980,538 A | 11/1999 | Fuchs et al. | |
| 5,993,466 A | 11/1999 | Yoon | |
| 5,997,554 A | 12/1999 | Thompson | |
| 6,042,601 A | 3/2000 | Smith | |
| 6,048,351 A | 4/2000 | Gordon et al. | |
| 6,051,006 A | 4/2000 | Shluzas et al. | |
| 6,053,933 A * | 4/2000 | Balazs et al. | 606/205 |
| 6,056,771 A | 5/2000 | Proto | |
| 6,071,289 A | 6/2000 | Stefanchik et al. | |
| 6,077,276 A | 6/2000 | Kontos | |

(56) References Cited

U.S. PATENT DOCUMENTS

| | | |
|---|---|---|
| 6,099,550 A | 8/2000 | Yoon |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,217,592 B1 | 4/2001 | Freda et al. |
| 6,221,085 B1 | 4/2001 | Djurovic |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,332,889 B1 | 12/2001 | Sancoff et al. |
| 6,355,050 B1 | 3/2002 | Andreas et al. |
| 6,368,334 B1 | 4/2002 | Sauer |
| 6,443,963 B1 | 9/2002 | Baldwin et al. |
| 6,454,778 B2 | 9/2002 | Kortenbach |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,605,096 B1 | 8/2003 | Ritchart |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,764 B1 | 4/2004 | Gellman et al. |
| 6,719,765 B2 | 4/2004 | Bonutti |
| 6,723,107 B1 | 4/2004 | Skiba et al. |
| 6,770,084 B1* | 8/2004 | Bain et al. .............. 606/144 |
| 6,896,686 B2 | 5/2005 | Weber |
| 6,921,408 B2 | 7/2005 | Sauer |
| 6,923,806 B2* | 8/2005 | Hooven et al. .............. 606/41 |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,377,926 B2* | 5/2008 | Topper et al. .............. 606/144 |
| 7,390,328 B2 | 6/2008 | Modesitt |
| 7,442,198 B2 | 10/2008 | Gellman et al. |
| 7,481,817 B2 | 1/2009 | Sauer |
| 7,491,212 B2 | 2/2009 | Sikora et al. |
| 7,588,583 B2 | 9/2009 | Hamilton et al. |
| 7,594,922 B2 | 9/2009 | Goble et al. |
| 7,608,084 B2 | 10/2009 | Oren et al. |
| 7,632,284 B2 | 12/2009 | Martinek et al. |
| 7,674,276 B2 | 3/2010 | Stone et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,938,839 B2 | 5/2011 | DiFrancesco et al. |
| 7,951,147 B2* | 5/2011 | Privitera et al. .............. 606/50 |
| 7,951,157 B2 | 5/2011 | Gambale |
| 7,951,159 B2* | 5/2011 | Stokes et al. .............. 606/157 |
| 7,972,344 B2 | 7/2011 | Murray et al. |
| 8,394,112 B2 | 3/2013 | Nason |
| 8,398,673 B2 | 3/2013 | Hinchliffe et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0083695 A1* | 5/2003 | Morris et al. .............. 606/222 |
| 2003/0105474 A1* | 6/2003 | Bonutti .............. 606/139 |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0010273 A1* | 1/2004 | Diduch et al. .............. 606/144 |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1* | 4/2006 | Privitera et al. .............. 606/50 |
| 2006/0106423 A1 | 5/2006 | Weisel et al. |
| 2006/0282098 A1 | 12/2006 | Shelton et al. |
| 2007/0032799 A1 | 2/2007 | Pantages et al. |
| 2007/0156150 A1 | 7/2007 | Fanton et al. |
| 2007/0219571 A1 | 9/2007 | Balbierz et al. |
| 2007/0250118 A1 | 10/2007 | Masini |
| 2007/0260260 A1* | 11/2007 | Hahn et al. .............. 606/102 |
| 2007/0260278 A1 | 11/2007 | Wheeler et al. |
| 2007/0270885 A1* | 11/2007 | Weinert et al. .............. 606/139 |
| 2008/0027468 A1 | 1/2008 | Fenton et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0294256 A1 | 11/2008 | Hagan et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1* | 3/2009 | Burkhart et al. .............. 606/148 |
| 2009/0105729 A1 | 4/2009 | Zentgraf |
| 2009/0105751 A1* | 4/2009 | Zentgraf .............. 606/206 |
| 2009/0112232 A1 | 4/2009 | Crainich et al. |
| 2009/0131956 A1 | 5/2009 | Dewey et al. |
| 2009/0209998 A1* | 8/2009 | Widmann .............. 606/207 |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1* | 11/2009 | Le et al. .............. 623/2.11 |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |

(56) References Cited

U.S. PATENT DOCUMENTS

| | | | |
|---|---|---|---|
| 2010/0228271 A1 | 9/2010 | Marshall et al. | |
| 2010/0241142 A1 | 9/2010 | Akyuz et al. | |
| 2010/0249806 A1 | 9/2010 | Oren et al. | |
| 2010/0249809 A1 | 9/2010 | Singhatat et al. | |
| 2010/0256656 A1 | 10/2010 | Park | |
| 2010/0280530 A1 | 11/2010 | Hashiba | |
| 2010/0305581 A1* | 12/2010 | Hart | 606/139 |
| 2010/0305583 A1 | 12/2010 | Baird et al. | |
| 2010/0331863 A2 | 12/2010 | Saliman | |
| 2011/0022063 A1 | 1/2011 | McClurg et al. | |
| 2011/0028998 A1 | 2/2011 | Adams et al. | |
| 2011/0060350 A1* | 3/2011 | Powers et al. | 606/144 |
| 2011/0071550 A1* | 3/2011 | Diduch et al. | 606/144 |
| 2011/0087245 A1* | 4/2011 | Weinert et al. | 606/144 |
| 2011/0087246 A1 | 4/2011 | Saliman et al. | |
| 2011/0100173 A1 | 5/2011 | Stone et al. | |
| 2011/0112555 A1 | 5/2011 | Overes et al. | |
| 2011/0112556 A1 | 5/2011 | Saliman | |
| 2011/0118760 A1* | 5/2011 | Gregoire et al. | 606/145 |
| 2011/0130773 A1* | 6/2011 | Saliman et al. | 606/145 |
| 2011/0152892 A1 | 6/2011 | Saliman et al. | |
| 2011/0190815 A1 | 8/2011 | Saliman | |
| 2011/0218557 A1 | 9/2011 | Saliman | |
| 2011/0251626 A1 | 10/2011 | Wyman et al. | |
| 2011/0270280 A1 | 11/2011 | Saliman | |
| 2012/0303046 A1 | 11/2012 | Stone et al. | |
| 2013/0072948 A1 | 3/2013 | States, III et al. | |
| 2013/0238040 A1 | 9/2013 | Saliman et al. | |
| 2013/0253647 A1 | 9/2013 | Saliman et al. | |
| 2014/0236192 A1 | 8/2014 | Hendricksen et al. | |
| 2014/0276987 A1 | 9/2014 | Saliman | |
| 2015/0034694 A1 | 2/2015 | Cappola | |
| 2015/0039030 A1 | 2/2015 | Saliman et al. | |
| 2015/0073442 A1 | 3/2015 | Saliman et al. | |
| 2015/0088163 A1 | 3/2015 | George et al. | |
| 2015/0142022 A1 | 5/2015 | George et al. | |

FOREIGN PATENT DOCUMENTS

| | | |
|---|---|---|
| EP | 0647431 A2 | 4/1995 |
| EP | 2081481 B1 | 11/2015 |
| JP | 3032847 U | 3/1991 |
| JP | 2009138029 A | 6/2009 |
| JP | 2009538190 | 11/2009 |
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/028532 A2 | 4/2003 |
| WO | WO 03/077771 A1 | 9/2003 |
| WO | WO 2005/037112 A1 | 4/2005 |
| WO | WO 2006/001040 A1 | 1/2006 |
| WO | WO 2006/007399 A1 | 1/2006 |
| WO | WO 2006/040562 A1 | 4/2006 |
| WO | WO 2010/036227 A1 | 4/2010 |
| WO | WO 2010/050910 A1 | 5/2010 |
| WO | WO 2010/141695 A1 | 12/2010 |
| WO | WO 2011/057245 A2 | 5/2011 |

OTHER PUBLICATIONS

Arthrex®, Arthrex, Inc., "The Next Generation in Shoulder Repair Technology," Product Brochure from Arthrex, Inc; Naples, Florida, 2007, 22 pages.

ArthroCare® Sportsmedicine, Sunnyvale, CA, SmartStitch® Suture Passing System with the PerfectPasserTM, Product brochure, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Cayenne Medical; CrossFix® II System (product webpage); 4 pgs.; downloaded Nov. 21, 2011 (www.cayennemedical.com/products/crossfix/).

Depuy Mitek, Inc; Raynham, MA, "Versalok Surgical Technique for Rotator Cuff Repair: The next generation in rotator cuff repair," Product brochure, 2007, 18 pages.

Linvatec Conmed Company, Largo, Florida, Product descriptions B17-19, B21; Tissue Repair Systems, Tissue Repair Accessories, and Master Arthroscopy Shoulder Instrument Set, 4 pages.

Ma et al; "Biomechanical Evaluation of Arthroscopic Rotator Cuff Stitches," J Bone Joint Surg Am, 2004; 86:1211-1216.

Nho et al; "Biomechanical fixation in Arthroscopic Rotator Cuff Repair," Arthroscopy: J of Arthroscop and Related Surg; vol. 23. No. 1 Jan. 2007: pp. 94-102.

Schneeberger, et al; "Mechanical Strength of Arthroscopic Rotator Cuff Repair Techniques: An in Vitro Study," J Bone Joint Surg Am., 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Tornier, Inc.; CINCH(TM) Knotless Fixation Implant System; 510K (K080335); 6 pgs.; Feb. 6, 2008.

USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.

USS SportsMedicine ArthoSewTM Suturing Device, <http://www.uss-sportsmed.com/SportsMedicine/pageBuilder.aspx?webPageID=0&topicID=7141&xs1=xsl/productPagePrint.xsl>, product description, accessed Apr. 25, 2007, 3 pages.

Asik et al.; Strength of different meniscus suturing techniques; Knee Sur, Sports Traumotol, Arthroscopy; vol. 5; No. 2; pp. 80-83; (month unavailable) 1997.

Asik et al.; Failure strength of repair devices versus meniscus suturing techniques; Knee Surg, Sports Traumatol, Arthrosc; vol. 10; No. 1; pp. 25-29; Jan. 2002.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Saliman et al.; U.S. Appl. No. 13/462,760 entitled "Methods of Meniscus Repair," filed May 2, 2012.

Saliman et al.; U.S. Appl. No. 13/462,728 entitled "Devices, Systems and Methods for Meniscus Repair," filed May 2, 2012.

Murillo et al.; U.S. Appl. No. 13/462,773 entitled "Suture Passer Devices and Methods," filed May 2, 2012.

Saliman, Justin D.; U.S. Appl. No. 13/347,184 entitled "Implant and method for repair of the anterior cruciate ligament," filed Jan. 10, 2012.

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

Medsfera; Suturing devices; accessed Dec. 4, 2012 at <http://www.medsfera.ru/shiv.html> 13 pages.

Baena et al.; Inside-out medial meniscus suture: an analysis of the risk of injury to the popliteal neurovascular bundle; Arthroscopy; 27(4):516-21; Apr. 2011.

Eggli et al.; Long-term results of arthroscopic meniscal repair. An analysis of isolated tears; Am J Sports Med; 23(6):715-20; Nov.-Dec. 1995.

Grant et al.; Comparison of inside-out and all-inside techniques for the repair of isolated meniscal tears: a systematic review; Am J Sports Med preview; Jul. 7, 2011; pp. 1-10.

(56) References Cited

OTHER PUBLICATIONS

Klecker et al.; The aberrant anterior tibial artery: magnetic resonance appearance, prevalence, and surgical implications; Am J Sports Med; 36(4):720-7; Apr. 2008.
Lozano et al.; All-inside meniscus repair: a systematic review; Clin Orthop Relat Res; 455:134-41; Feb. 2007.
Paxton et al.; Meniscal repair versus partial meniscectomy: a systematic review comparing reoperation rates and clinical outcomes; Arthroscopy; 27(9):1275-88; Sep. 2011.
Pujol et al.; Meniscal healing after meniscal repair: a CT arthrography assessment; Am J Sports Med; 36(8):1489-95; Aug. 2008.
Rockborn et al.; Results of open meniscus repair. Long-term follow-up study with a matched uninjured control group; J Bone Joint Surg Br; 82(4):494-8; May 2000.
Small et al.; Avoiding Complications in Meniscal Repair; Techniques in Orthopaedics; 8(2):70-75; Summer Jun.-Aug. 1993.
Stärke et al.; Current Concepts: Meniscal Repair; Arthroscopy: The Journal of Arthroscopic and Related Surgery; vol. 25; Issue 9; pp. 1033-1044; Sep. 2009.
Duerig, T. et al., "An overview of nitinol medical applications" Materials Science and Engineering A273-275, May 1999.
Strobel; Manual of Arthroscopic Surgery (1st Edition); Springer Verlag, Hiedelberg © 2002; pp. 127-129; Dec. 15, 2001.
Hirotsuka et al.; U.S. Appl. No. 13/758,994 entitled "Pre-Tied Surgical Knots for Use With Suture Passers," filed Feb. 4, 2013.
McCutcheon et al.; U.S. Appl. No. 13/759,000 entitled "Methods and Devices for Preventing Tissue Bridging While Suturing," filed Feb. 4, 2013.
Saliman, J.; U.S. Appl. No. 13/759,006 entitled "Suture Passers," filed Feb. 4, 2013.
Hendricksen et al.; U.S. Appl. No. 13/844,252 entitled "Suture passers and methods of passing suture," filed Mar. 15, 2013.
Murillo et al.; U.S. Appl. No. 13/893,154 entitled "Suture passer devices and methods," filed May 13, 2013.
Murillo et al.; U.S. Appl. No. 14/572,485 entitled "Automatically reloading suture passer devices and methods," filed Dec. 16, 2014.
Hendricksen et al.; U.S. Appl. No. 14/659,471 entitled "Suture passer with radiused upper jaw," filed Mar. 16, 2015.
Hendricksen et al.; U.S. Appl. No. 14/681,528 entitled "Suture passers adapted for use in constrained regions," filed Apr. 8, 2015.
Hendricksen et al.; U.S. Appl. No. 14/697,494 entitled "Suture passers adapted for use in constrained regions," filed Apr. 27, 2015.

\* cited by examiner

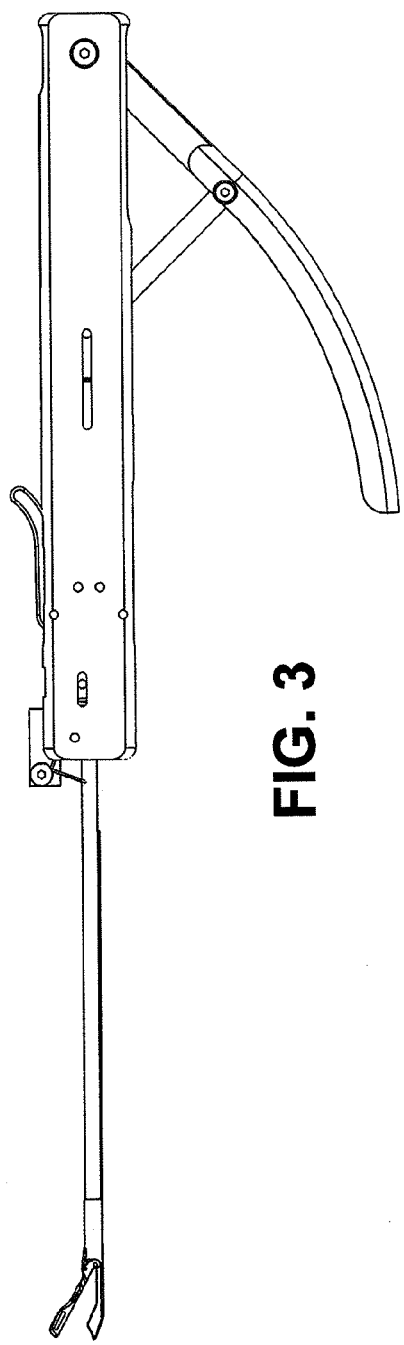
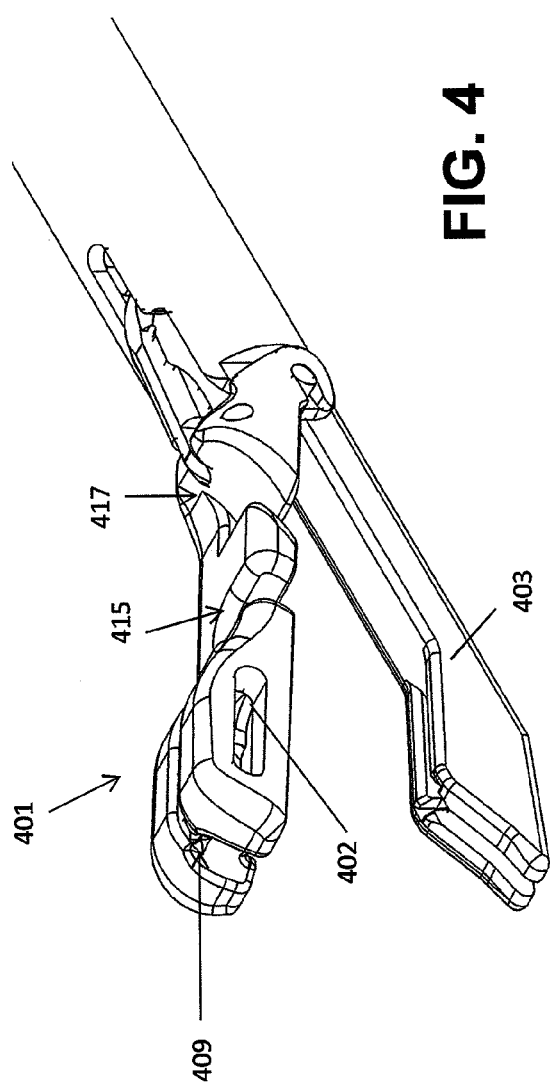
FIG. 3
FIG. 4

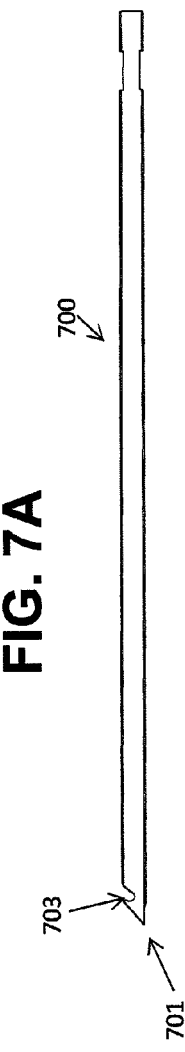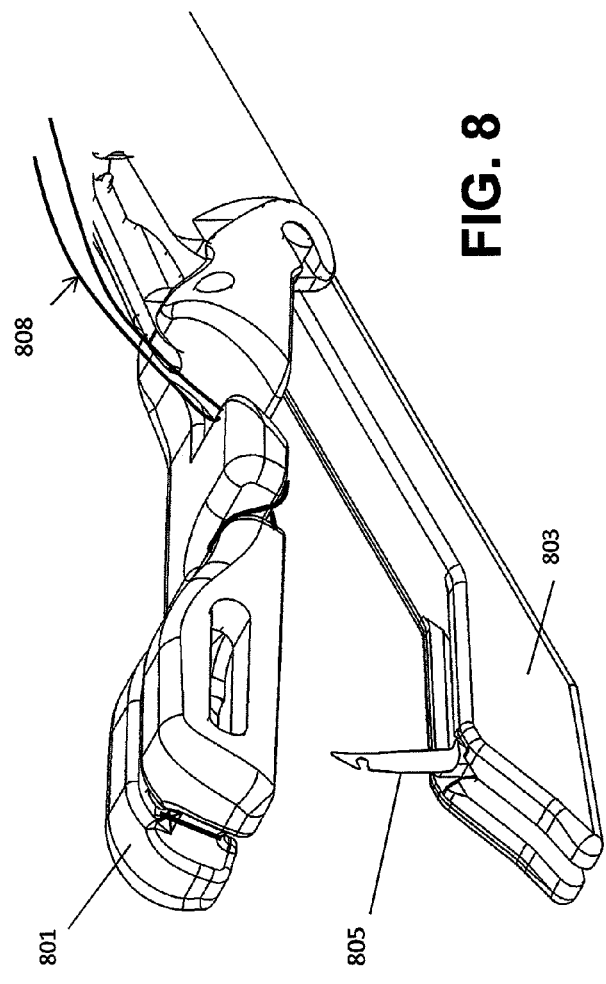

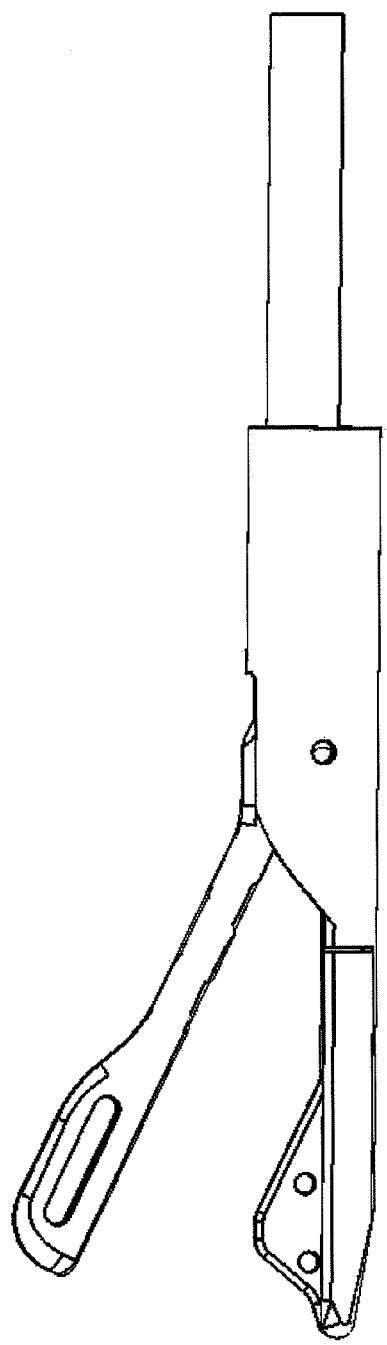
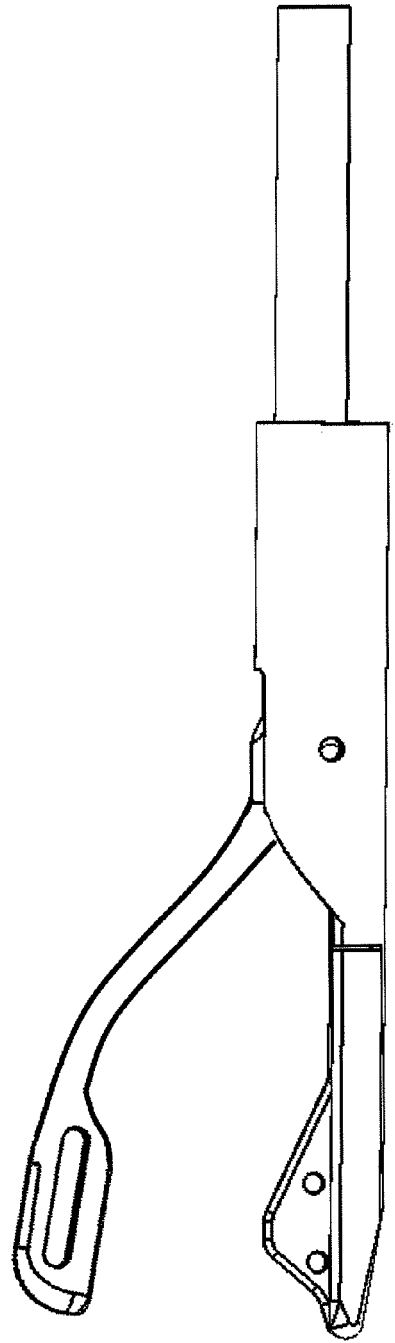
FIG. 10A
FIG. 10B

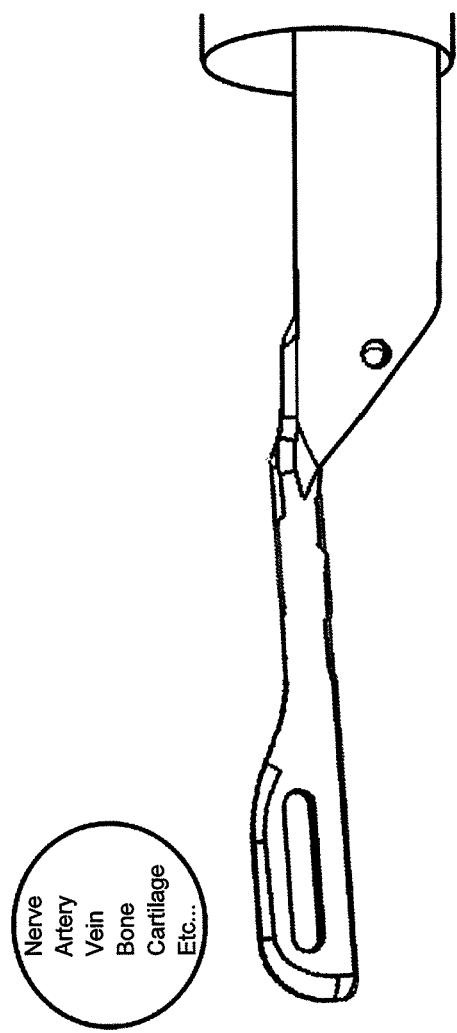
FIG. 12B

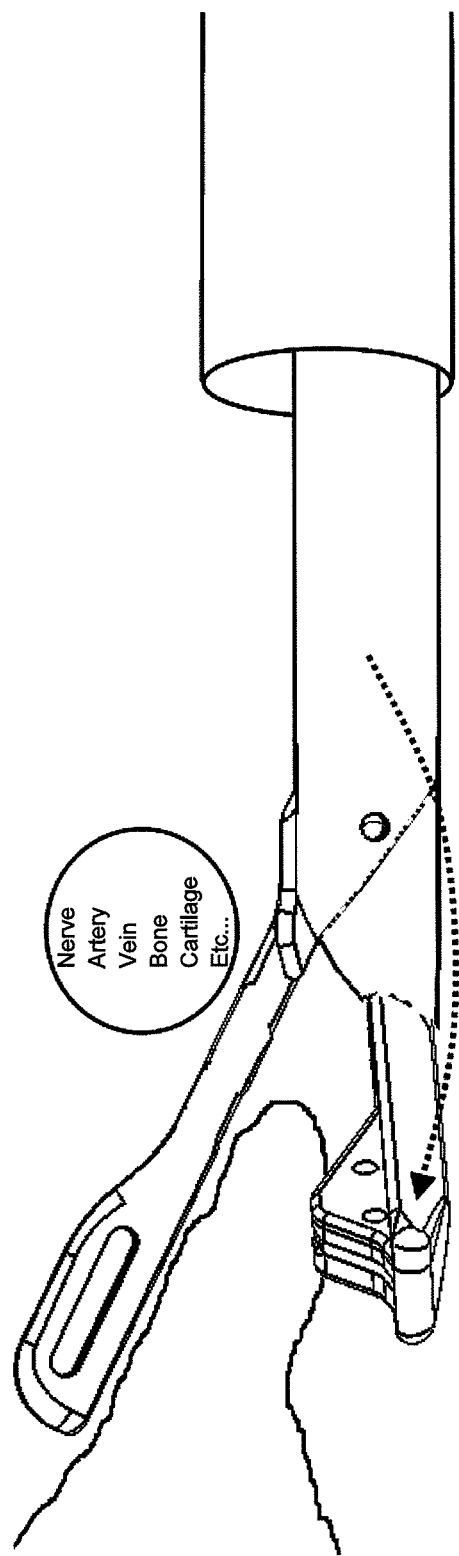

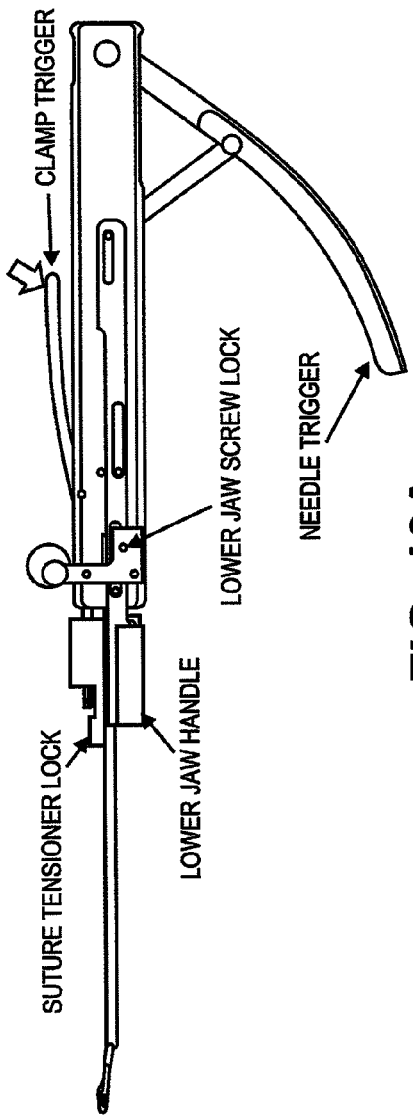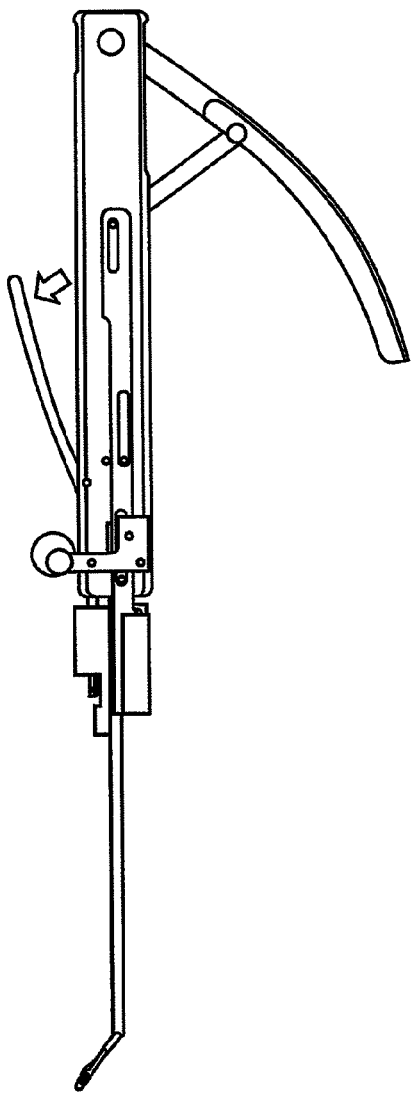
FIG. 19A
FIG. 19B

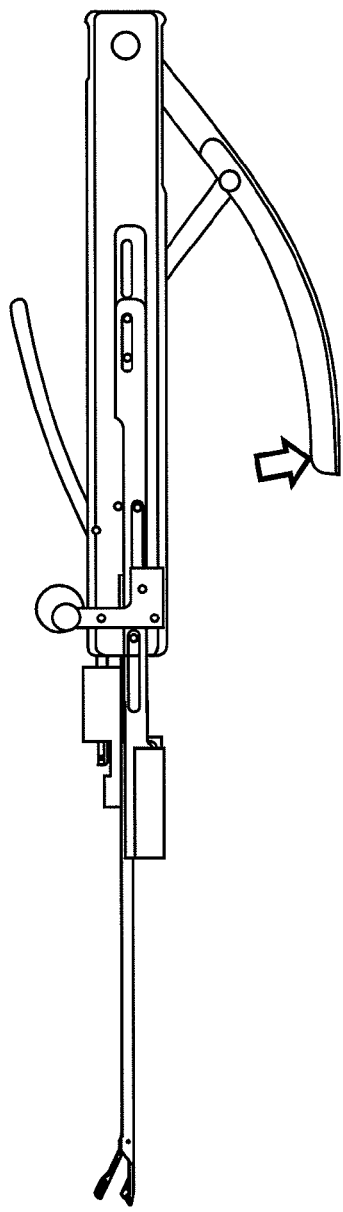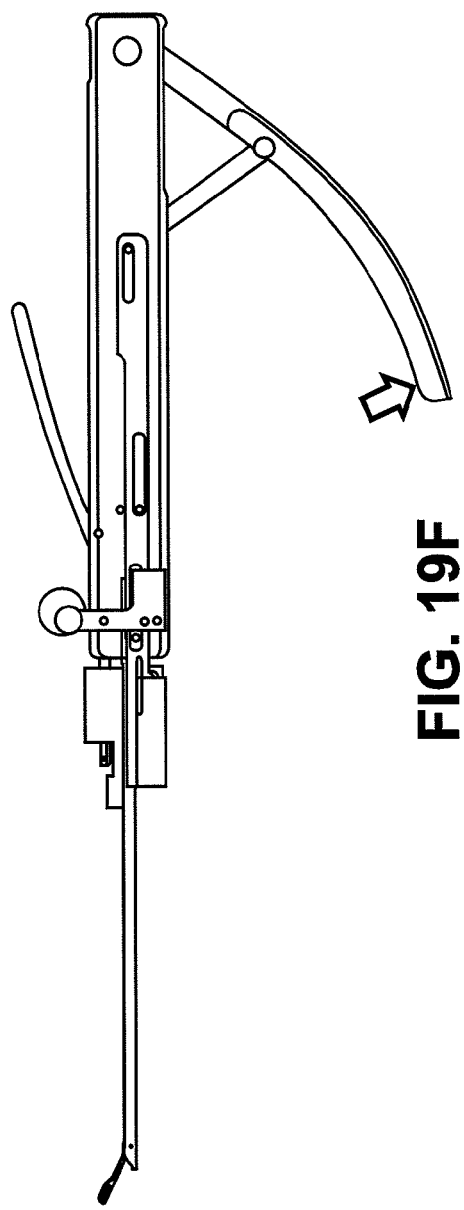

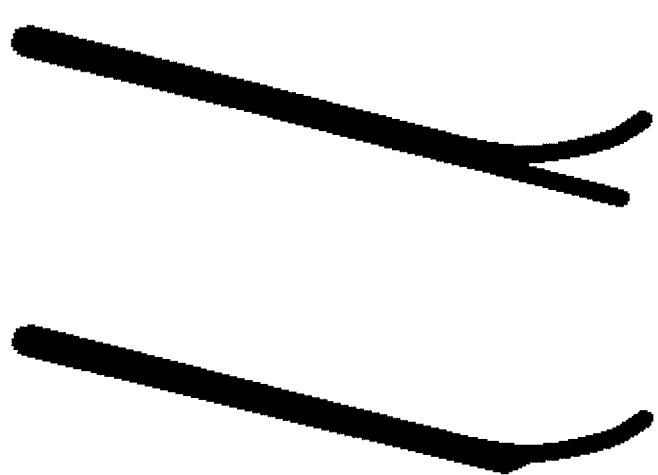

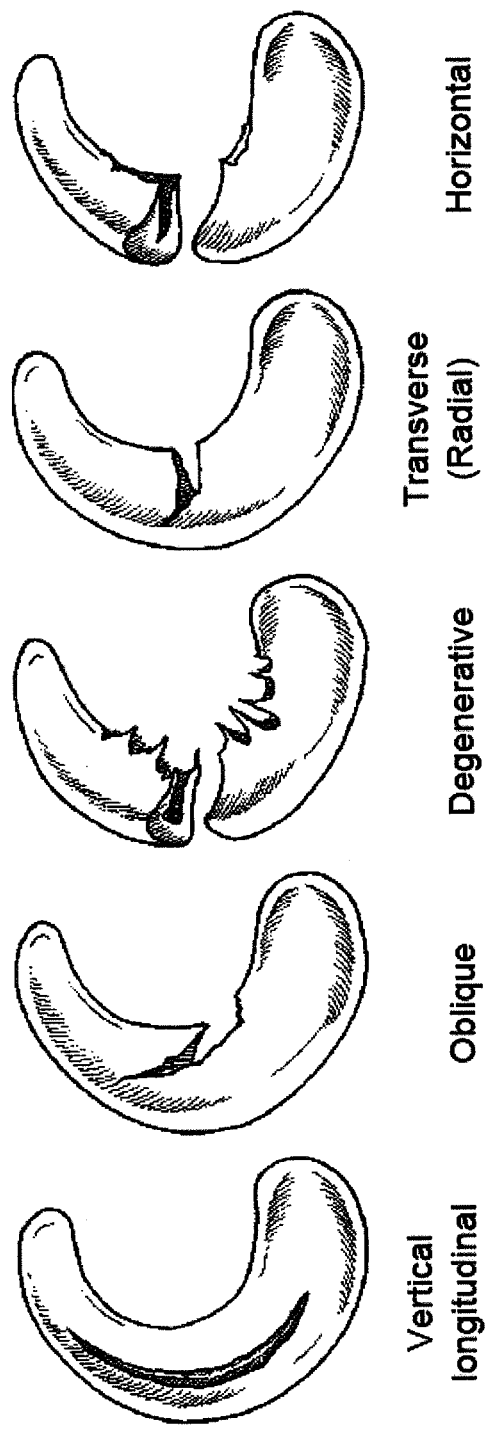

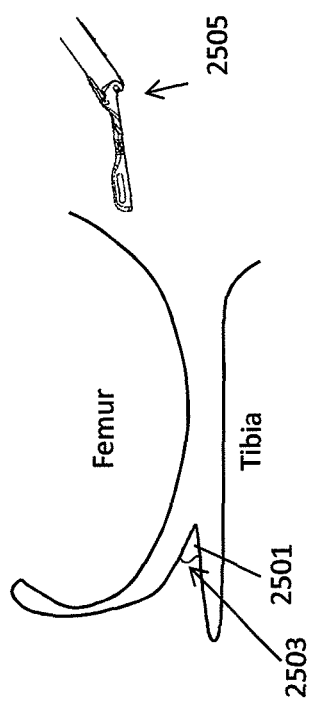
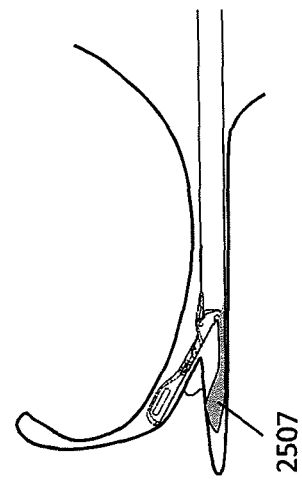
FIG. 25A  FIG. 25C
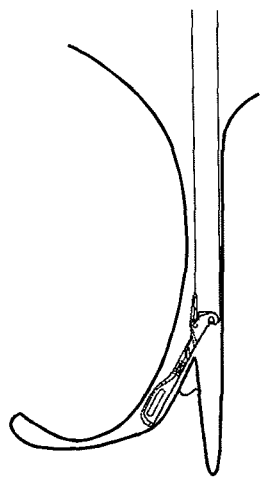
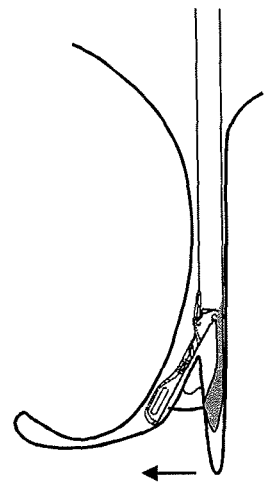
FIG. 25B  FIG. 25D

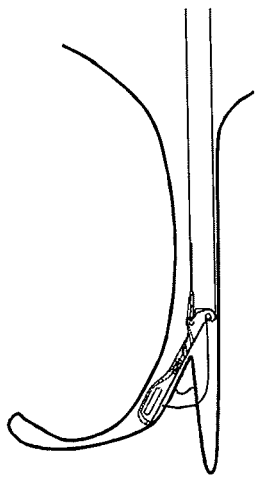
FIG. 25E
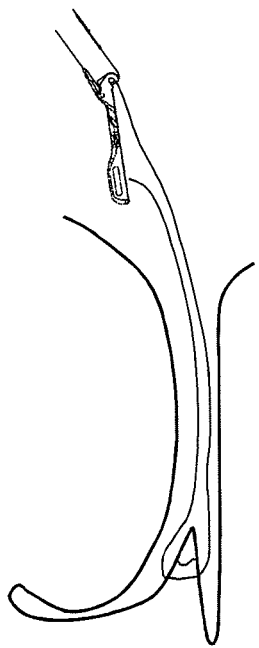
FIG. 25G
FIG. 25F
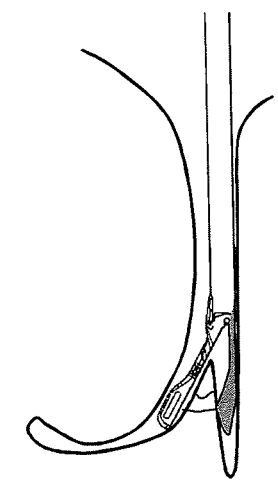
FIG. 25H

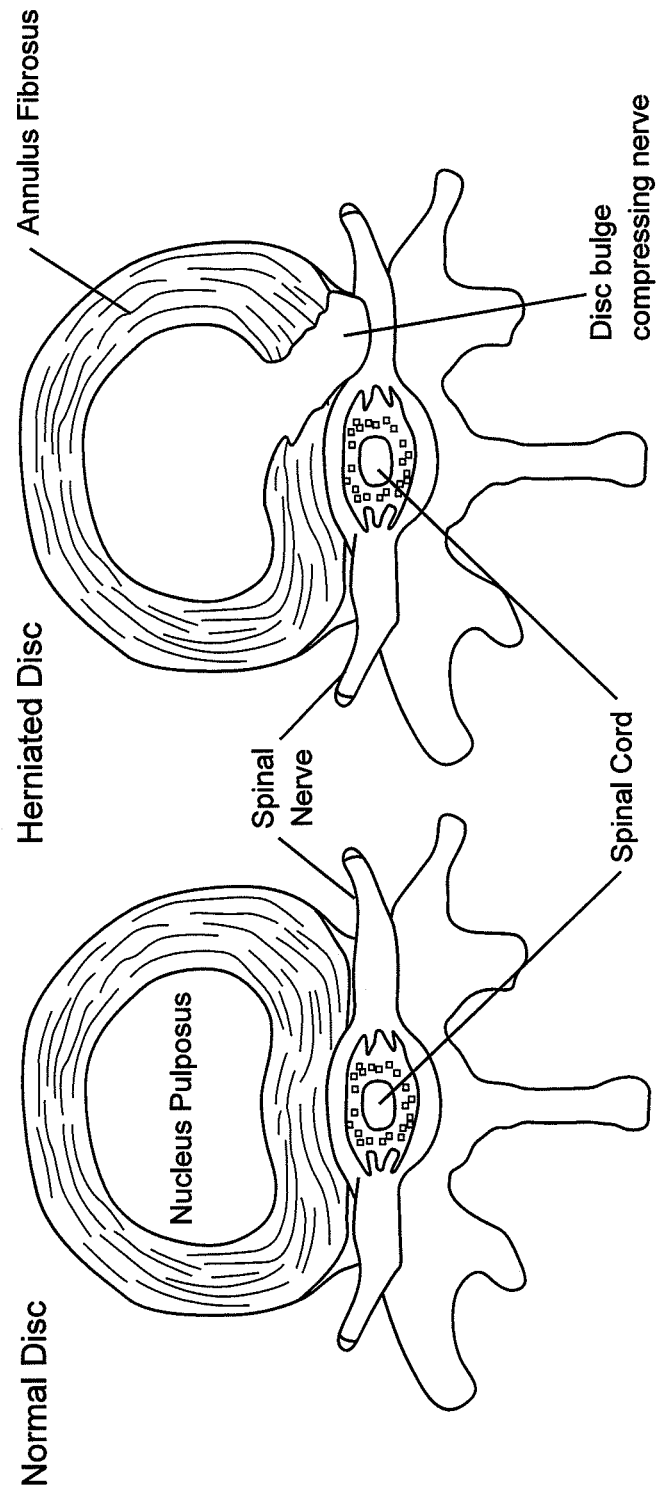

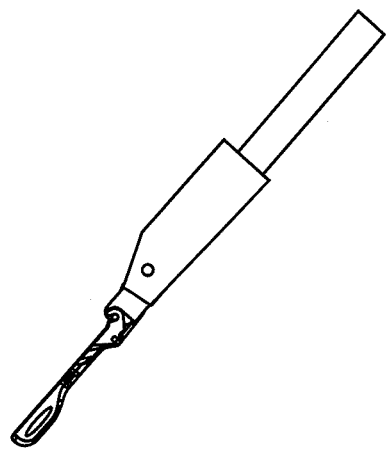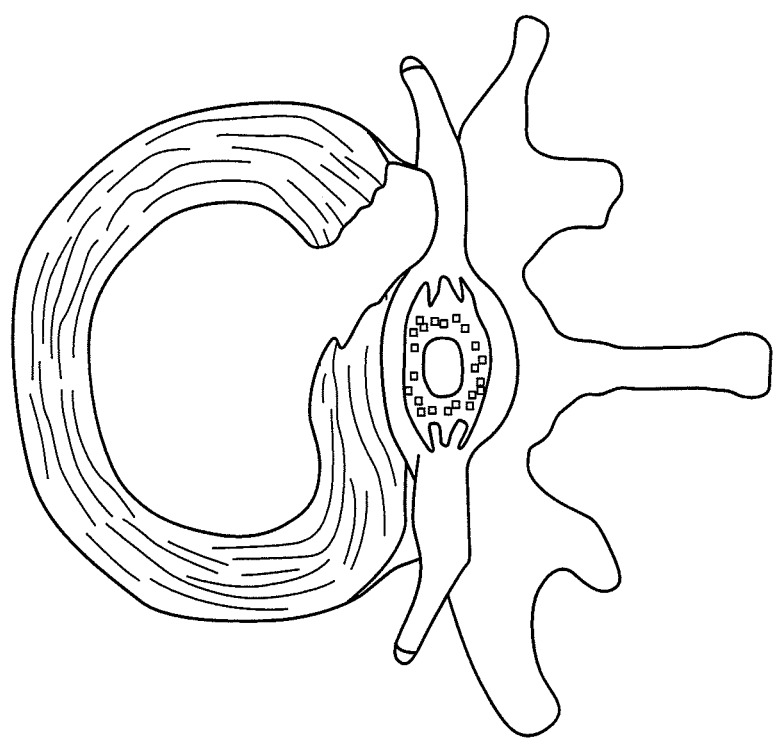
FIG. 30A

SUTURE PASSER DEVICES AND METHODS

CROSS REFERENCE TO RELATED APPLICATIONS

This patent application claims the benefit of priority to the following provisional patent applications: U.S. Provisional Patent Application No. 61/483,200, titled "MENISCUS REPAIR", filed on May 6, 2011, and U.S. Provisional Patent Application No. 61/511,922, titled "MENISCUS REPAIR", filed on Jul. 26, 2011.

This patent application may be related to U.S. patent application Ser. No. 12/942,803, titled "DEVICES, SYSTEMS AND METHODS FOR MENISCUS REPAIR", filed on Nov. 9, 2010, which claim priority to U.S. Provisional Patent Application Nos. 61/259,572, titled "DEVICES, SYSTEMS EMS AND METHODS FOR MENISCUS REPAIR", filed on Nov. 9, 2009; 61/295,354, titled "DEVICES, SYSTEMS AND METHODS FOR MENISCUS REPAIR", filed on Jan. 15, 2010; and 61/318,215, titled "CONTINUOUS SUTURE PASSERS HAVING TISSUE PENETRATING SUTURE SHUTTLES", filed on Mar. 26, 2010.

All of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods, devices and systems described herein may be used to suture tissue, particularly in difficult to access regions. In particular, described herein are highly maneuverable dual deployment suture passers configured to be deployed around a target tissue to be sutured.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and generally assisting a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

For example, some variations of suture passers, such as those described in U.S. Pat. No. 7,377,926 to Taylor, have opposing jaws that open and close over tissue. One, or in some variations, both, jaws open, scissor-like, so that tissue may be inserted between the open jaws. Unfortunately, such devices cannot be adequately positioned for use in hard to navigate body regions such as the joints of the body, including the knee (e.g., meniscus) and the shoulder.

The meniscus is a C-shaped piece of fibrocartilage which is located at the peripheral aspect of the joint (e.g., the knee) between the condyles of the femur and the tibia on the lateral and medial sides of the knee. The central $2/3^{rds}$ of the meniscus has a limited blood supply while the peripheral $1/3^{rd}$ typically has an excellent blood supply. Acute traumatic events commonly cause meniscus tears in younger patients while degenerative tears are common in older patients as the menisci become increasingly brittle with age. Typically, when the meniscus is damaged, a torn piece may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately 1/8 inch long. Fluid may then be inserted into the joint to distend the joint and to allow for visualization of the structures within that joint. Then, using miniature instruments which may be as small as 1/10 of an inch, the structures are examined and the surgery is performed.

FIGS. 21A, 21B and 22 illustrate the anatomy of the meniscus in the context of a knee joint. As shown in FIG. 22 the capsule region (the outer edge region of the meniscus) is vascularized. Blood enters the meniscus from the meniscu-locapsular region 211 lateral to the meniscus. A typical meniscus has a flattened ("bottom") and a concave top, and the outer cross-sectional shape is somewhat triangular. The outer edge of the meniscus transitions into the capsule. FIG. 23 illustrates the various fibers forming a meniscus. As illustrated in FIG. 23, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed.

For example, FIGS. 24A-24E illustrate various tear patterns or injuries to a meniscus. Tears may be vertical/ longitudinal (FIG. 24A), Oblique (FIG. 24B), Degenerative (FIG. 24C), including radially degenerative, Transverse or radial (FIG. 24D) and Horizontal (FIG. 24E). Most prior art devices for suturing or repairing the meniscus are only capable of reliably repairing vertical/longitudinal tears. Such devices are not typically useful for repairing radial or horizontal tears. Furthermore, prior art device mechanisms have a high inherent risk for iatrogenic injury to surrounding neurovascular structures and chondral surfaces.

Thus, there is a need for methods, devices and systems for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Finally, it is useful to provide a suturing device that allows the tissue to be sutured to be held within an adjustable jaw so that it can be predictably sutured, and done so in a manner that protects fragile surrounding tissues from iatrogenic injury. The methods, devices and systems described herein may address this need.

SUMMARY OF THE DISCLOSURE

The present invention relates to devices, systems and methods for suturing tissue, including a torn meniscus. In general, described herein are suturing devices, such as suture passers, as well as methods of accessing and repairing tissue using these suture passers, including methods of suturing tissue. The device and methods described herein allow methods of suturing and repairing tissue that were previously impossible or impractical to perform during a surgical procedure.

The suture passers described herein may also be referred to as dual deployment suture passers, because the tissue engaging region of the suture passer comprises a distal-facing opening formed between two jaws (a first jaw member and a second jaw member), and each jaw member moves (is deployed) independently with a different type (e.g., axis, plane, range, etc.) of motion. Many of the devices described herein may also be referred to as clamping/sliding suture passers, because the first jaw member acts to clamp onto the tissue, by changing the angle of the first jaw member relative to the more proximal elongate body region of the device, and the second jaw member slides, moving axially relative to the more proximal elongate body region of the device.

Thus, in many of the dual deployment suture passer described herein, the first jaw member generally extends distally from a proximal elongate body region; the angle of the first jaw member relative to the proximal elongate body region is adjustable. These dual deployment suture passers also have a second jaw member that may be moved from a position proximal to the first jaw member and/or proximal to the distal end of the elongate body region to a distal position to form a distal-facing jaw opening with the first jaw member.

Because of this novel jaw movement, a dual deployment suture passer may readily access and be positioned around tissue to be sutured in ways not possible with more traditional suture passers. Generally a dual deployment suture passer may be positioned within the tissue by adjusting the angle of the first jaw member to help avoid non-target tissue as the device is advanced so that the first jaw member is adjacent to the target tissue. The second jaw member may then be extended distally from the proximal position (e.g., by sliding axially, by swinging distally, etc.) so that the tissue is held between the first and second jaw members in a distal-facing jaw opening. The tissue to be sutured may then be clamped securely between the first and second jaw members (e.g., by adjusting the angle of the first jaw member), and a suture may be passed between the two by extending a tissue penetrator from within one of the first or second jaw members, across the opening and through the tissue, to either drop off or pick up a suture at the opposite jaw member. The tissue penetrator can then be retracted back into the jaw member that houses it.

For example, described herein are methods of arthroscopically placing a suture. The suture may be placed entirely arthroscopically. For example, two or fewer incisions may be made into the body (e.g., knee, shoulder, etc.), and a camera and suture passer may be placed within the knee. In any of these methods, the suture may be placed by independently or sequentially moving a first distal jaw member through a first range of motion before, during or after placing the distal end of the suture passer into the tissue region. A second jaw member is typically held proximally to the first jaw member either within or aligned with the more proximal elongate body region of the suture passer. After positioning the distal end of the suturing device, including the distally-extending first jaw member against the target tissue to be sutured, the second jaw member may be advanced distally until it is positioned opposite from the first jaw member. The tissue may be secured between the first and second jaw members. In general the second jaw member may be moved into position by moving the second jaw member in a path of motion that is different from that of the first jaw member. For example, the first jaw member may be hinged to move at an angle relative to the elongate body of the device, while the second jaw member extends distally (and retracts proximally) by sliding axially relative to the elongate body of the device.

For example, described herein are dual deployment suture passer devices. In some variations these devices include: an elongate body having a proximal end region and a distal end region; a first jaw member extending from the distal end region of the elongate body and configured for angular movement relative to the elongate body; a second jaw member configured to extend axially relative to the elongate body, the second jaw configured to form an opening with the first jaw member when the second jaw member is axially extended; and a tissue penetrator deployably held within either the first or second jaw member and configured to pass a suture between the first and second jaw members by extending and retracting between the first and second jaw members when the first and second jaw members form the opening.

In some variations, the second jaw member may be contained within the elongate body; in other variations, it is held outside of the elongate body (e.g., secured adjacent to the outside of the elongate body). The elongate body may be straight, curved, or bendable; in some configurations the elongate body is tubular and extends as an elongate tube. In general, the elongate body may have any appropriate cross-section, including round, oval, square, triangular, or the like. The cross-section of the elongate body may be uniform, or it may vary along the length. In some variations, the elongate body may be narrower towards the distal end, which may allow the device to be inserted into various regions of the body.

In general, the device may be configured so that the tissue penetrator extends between the first and second jaw members when they are fully deployed distally. In this configuration, they may be referred to as distal opening or having a distal-facing opening. In some variations the first jaw member and the second jaw member are deployed or deployable to form a distal facing opening into which the target tissue can be positioned or held. In some variations the distal opening formed between the jaws is formed around the target tissue by placing the first or the second jaw members adjacent the target tissue and moving the other jaw member (e.g., second or first jaw members) on the opposite side of the target tissue.

The tissue penetrator may be any appropriate tissue penetrating member. For example, the tissue penetrator may be a needle or tissue penetrating probe. The tissue penetrator may include a suture engagement region for releaseably engaging a suture. In some variations the suture engagement region is a hook, notch, clamp, grasper, eyelet, slot, or the like. The suture engagement region may be positioned at or near the distal end, or just proximal to the distal end of the tissue penetrator. The distal end of the tissue penetrator may be sharp (e.g., pointed, beveled, etc.) or it may be substantially dull. The tissue penetrator may be a metal, polymeric, alloy, ceramic, composite, or other material. Shape memory or superelastic materials, including superelastic alloys (such as Nitinol) may be used. Thus, as mentioned, the device may include a suture engagement region at or near a distal tip of the tissue penetrator configured to couple with a suture.

In general, the tissue penetrator may extend between the first and second jaw members only when the first and second jaw members are positioned to form an opening between which tissue may be held. In some variations the suture passer includes a lock or other element preventing or limiting (e.g., a limiter) the tissue penetrator motion from extending between or beyond the first and second jaw members.

During operation, the tissue penetrator generally extends from either the first or second jaw members, across the opening between the first and second jaw members (including through any tissue between the jaw members), to engage with a suture retainer on the opposite jaw. The suture retainer may hold a suture so that it can be engaged (grabbed) by the tissue penetrator. For example, in some variations the tissue penetrator extends across the opening between the first and second jaw members until it engages with a suture held by the opposite jaw member (e.g., in a suture retainer); thereafter the tissue penetrator can be retracted back across the opening and pull the suture with it. In some variations the suture is preloaded onto the tissue penetrator and the suture retainer grabs the suture from the tissue penetrator (or the tissue penetrator deposits the suture in the suture retainer) and holds on the opposite jaw as the tissue penetrator is retracted back across the opening and through any tissue there between.

The motion of the tissue penetrator may be regulated to prevent the tissue penetrator from extending beyond the opening formed between the first and second jaw members as it extends across this opening. In particular, a dual deployment suture passer may be configured to prevent the tip of the tissue penetrator from extending beyond the outside of a jaw member. Extending beyond the jaw member may result in damage to surrounding (non-target) tissues. For example, the suture passer may be configured so that the extent of travel of the tissue penetrator is limited based on how "open" the jaw members are; in variations in which the size of the opening can be modified by adjusting the angle of the first jaw member relative to the elongate body of the device, a limiter may prevent the tissue penetrator from extending further beyond the side of a jaw member opposite from the jaw member housing the tissue penetrator. For example, the tissue penetrator may be configured to extend and retract between the first and second jaw members without extending substantially beyond a lateral side of the first or second jaw members opposite the opening. Thus, the devices described herein may also include a movement limiter configured to limit the movement of the tissue penetrator based on a position of the first jaw member, the second jaw member or both the first and second jaw members, relative to the elongate body.

In some variations the limiter (e.g., a travel limiter) may be employed to keep the tissue penetrator from extending beyond the opening and opposite jaw member. For example, a limiter may include a barrier, block, cage, or the like on the opposite jaw member preventing the tip of the tissue penetrator from extending beyond the jaw member when the tissue penetrator is extended across the opening.

Thus, the suturing device may also include a travel limiter configured to prevent the tissue penetrator from extending substantially beyond a lateral side of the first or second jaw members opposite the opening (in FIG. 2D, the lateral side of the first jaw member 201 is shown by arrow 290, and the lateral side of the second jaw member is shown by arrow 293.

One of the jaw members (e.g., the second) jaw member may be configured to move axially by extending distally or retracting proximally from the distal end region of the elongate body. Thus, the second jaw member may extend parallel to the long axis of the elongate body; in curved variations of the elongate body, the second jaw member extends distally in the direction continuing the distally moving trajectory of the elongate body. The second jaw member may extend axially from within the elongate body, or from adjacent to the elongate body. In some variations the entire second jaw member may retract within the elongate body.

In some variations, the opening formed between the first and second jaw members by extending the second jaw member distally is a distal-facing opening, as described above. In some variations the device includes a holdfast to hold one or both jaw element in a fixed position; the holdfast may be released or engaged by user control. For example, the suturing device may include a first and/or second jaw holdfast configured to hold the first and/or second jaw members in a fixed position relative to the elongate body. In one variation, the device includes a first jaw holdfast configured to hold the first jaw member in an angular position relative to the elongate body (see, e.g., FIG. 17B, element 1790) and/or a second jaw holdfast (see, e.g., FIG. 17B, element 1795) to hold the second jaw element in a fixed axial position relative to the elongate body.

Any of the device variations described herein may include a handle at the proximal end of the device. The handle may be controlled by a user (e.g., surgeon) to actuate the various elements of the device, including the first jaw member, the second jaw member, and the tissue penetrator. The handle may therefore include one or more controls. For example, the device may include a first control for controlling the angular position of the first jaw member relative to the elongate body and a second control for controlling the axial position of the second jaw member relative to the elongate body. These controls may be on the proximal handle.

The device may also include an indicator for indicating when the second jaw is in a predetermined axially extended position relative to the elongate body (see, e.g., FIG. 17B, element 1797). The indictor may be visual, tactile, aural, or the like, including some combination of these. In some variations a separate indicator is not necessary; the full extension of the second (or first) jaw member may be the fully engaged position. Thus, when further actuation of the control (e.g., squeezing a trigger, moving a level, dial, or the like) does not result in any further actuation. In some variations the control may "stop" when the jaw member is fully extended.

Thus, in some variations, the device includes a proximal handle having controls for controlling at least one of the angular movement of the first jaw member, the axial movement of the second jaw member or the extension and retraction of the tissue penetrator.

Also described herein are suture passer devices (e.g., a dual deployment suture passers) comprising: an elongate body having a proximal end region and a distal end region; a first jaw member extending from the distal end region of the elongate body and configured for angular movement relative to the elongate body; a second jaw member configured to extend distally or retract proximally from the distal end region of the elongate body; and a tissue penetrator configured to pass a suture between the first and second jaws and further configured to extend and retract between the first and second jaw members when the second jaw member is extended distally to form a distal-facing opening with the first jaw member.

Any of the features described above may be included in these variations as well. For example, the device may also include a suture engagement region near a distal tip of the tissue penetrator, the suture engagement region configured to couple with a suture. In some variations the device also includes a movement limiter configured to limit the movement of the tissue penetrator based on a position of the first jaw member, the second jaw member or both the first and second jaw members.

Also described herein are suture passer devices including: a hinged first jaw member extending from a distal end of an elongate body and configured to controllably bend relative to a longitudinal axis of the elongate body; an axially sliding second jaw member configured to extend distally and retract proximally relative to the distal end of the elongate body to form a distal-facing opening with the first jaw member when the second jaw member is extended distally; a tissue penetrator housed within the second jaw member and configured to extend across the distal-facing opening to the first jaw member; a suture engagement region disposed near a distal end of the tissue penetrator and configured to engage a suture; and a travel limiter configured to engage the tissue penetrator and prevent the tissue penetrator from extending beyond a lateral side of the first or second jaw members opposite the distal-facing opening.

Although many of the device variations just described include a second jaw member that is axial movable, in some variations the second jaw member is movable in other dimensions in addition to, or alternatively to, the axial direction. Generally the second jaw member is movable in a direction that is different from the manner of movement of the first jaw member, and extends the second jaw member from a position in which the distal end (e.g., tip) region of the second jaw member is proximal to the distal end of the elongate body. Movement of the second jaw member may be independent of the movement of the first jaw member.

Also described herein are methods of suturing a tissue, the method comprising: moving a first jaw member of a dual deployment suture passer so that the first jaw member extends distally from a proximal elongate body region of the suture passer at an angle with respect to a longitudinal axis of the proximal elongate body region; positioning the first jaw member adjacent to a tissue to be sutured; extending a second jaw member of the suture passer distally relative to the elongate body region to form a distal-facing opening between the first and second jaw members, so that the tissue to be sutured is within the distal-facing opening; and passing a suture through the tissue within the distal-facing opening by moving a tissue penetrator coupled to a suture between the first and second jaw members.

The method may also include the step of preventing the tissue penetrator from extending beyond a lateral side of the first or second jaw members opposite the distal-facing opening when passing the suture. In some variations, the method also includes the step of retracting the second jaw member proximally relative to the elongate body and withdrawing the suture passer from the tissue.

This method may be used to treat (e.g., suture) as part of a variety of treatments, including, but not limited to, repair of a torn meniscus, repair of a torn ACL, labral tear repair, hip labrum repair, spinal disc repair, etc. In any of these variations, the method of treatment (method of suturing tissue) may include the step of positioning the first jaw adjacent to the tissue to be sutured, such as the meniscus, labrium, ACL, spinal disc/annulus, etc. For example, the step of positioning the first jaw member may comprise positioning the first jaw member adjacent to meniscus tissue.

These devices and methods may be used as part of a minimally invasive (e.g., percutaneous) or open procedure. For example, the method of suturing may also include the step of percutaneously inserting the suture passer near the tissue to be sutured.

The step of passing the suture through the tissue may comprise extending the tissue penetrator from the second jaw member through the tissue to the first jaw member, engaging the suture held in the first jaw member and retracting the tissue penetrator back to the second jaw member while holding the suture with the tissue penetrator. In some variations, the step of passing the suture through the tissue comprises extending the tissue penetrator coupled to a suture from the second jaw member through the tissue to the first jaw member, engaging the suture with a suture retainer in the first jaw member and retracting the tissue penetrator back to the second jaw member.

BRIEF DESCRIPTION OF THE DRAWINGS

FIG. 3 is a side view of the suture passer shown in FIG. 1.

FIG. 4 is a front perspective view of the suture passer shown in FIG. 3 in which the first jaw member is positioned at an angle relative to the longitudinal axis of the elongate body of the device, and the second jaw member is extended fully distally relative to the elongate body to form a distal-facing jaw opening.

FIG. 7A shows a side view of one variation of a tissue penetrator.

FIG. 7B shows a side perspective view of the tissue penetrator of FIG. 7A.

FIG. 8 shows the perspective view of FIG. 4 with a tissue penetrator partially extended between the first and second jaw members, and with a suture loaded in the first jaw member.

FIG. 10A shows a side view of one variation of the distal end region of a suture passer, showing a first and second jaw member extended in to form a distal facing opening.

FIG. 10B shows another variation of the distal end region of a suture passer with the first and second jaw member extended in to form a distal facing opening.

FIGS. 12A-12E illustrate operation of one variation of a dual deployment suture passer configured as a clamping/sliding suture passer.

FIGS. 13A-13C illustrate operation of one variation of a dual deployment suture passer configured as a clamping/side-swinging suture passer.

FIGS. 19A-19F illustrate operation of one variation of dual deployment suture passer.

FIGS. 20A and 20B show a generic form of a dual deployment suture passer.

FIGS. 24A-24E illustrate various tear patterns that may be repaired using the invention described herein.

FIGS. 25A-25H illustrate the use of a dual deployment suture passer to suture a torn meniscus.

FIG. 28 shows an exemplary section through a spine showing a normal disc;

FIG. 29 shows a similar section through a spine having a herniated disc.

FIGS. 30A-F illustrate the use of a dual deployment suture passer to repair a herniated disc.

DETAILED DESCRIPTION

Described herein are suture passers. In general, these devices may be referred to herein as suture passers, suturing devices. The devices described herein may also be referred to as dual deployment suture passers, or in some variations, clamping/sliding suture passers.

Figure 1:
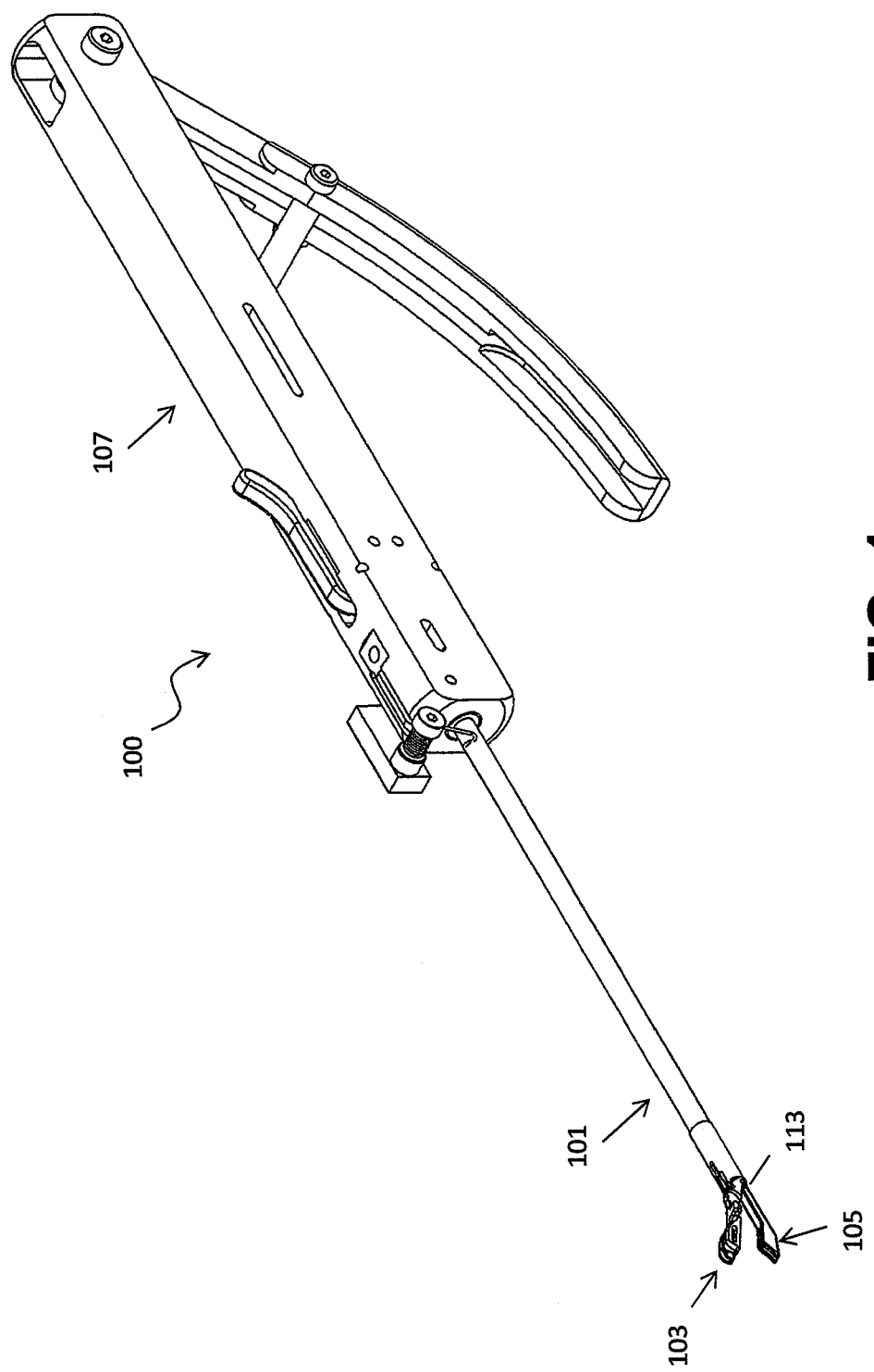
FIG. 1 shows one variation of a dual deployment suture passer as described herein.

In general, the suture passers described herein include a first jaw member and second jaw member that are configured to extend from the end of an elongate body region. FIG. 1 illustrates one variation of a dual deployment suture passer 100. In this example, the device has a first (upper) jaw member 103 extending distally from the distal end of a more proximal elongate member 101. A second jaw member 105 is shown extended distally beneath the first jaw member 105. A handle 107 is located at the proximal end of the device and includes multiple controls for independently controlling the movements of the first jaw member, second jaw member, and tissue penetrator. The handle in this example also includes a second jaw member lock for locking/unlocking the movement of the second jaw member.

The suture passer shown in FIG. 1 is positioned with the first jaw member held at an angle relative to the long axis of the proximal elongate member. The first jaw member in this example is shown having a hinge region 113 about which the first jaw member may be angled relative to the elongate member. In some variations this hinge region is a pinned hinge; non-pinned (e.g., living hinges) regions may be used. Any appropriate articulating region that allows the first jaw member to move at an angle relative to the proximal portion of the device (e.g., the elongate member) may be used. In some variations this first jaw member is referred to as an upper jaw member, but alternative variations (in which the first jaw member is a lower jaw member) are also possible.

The first jaw member may be actuated by any appropriate mechanism, including a tendon member (e.g., push rod, pull rod, or the like), and may be held (locked) at any angle (e.g., between 0° and 180° relative to a line extending from the distal end of the elongate body, between about 0° and 90°, between about 0° and 60°, etc.). In some variations the device has a neutral position during which no force is applied to the controller to move the first jaw member, so that the first jaw member is angled "open" (e.g., at 30°, 45°, 50°, 90° or at any angle between about 15° and about 90° relative to the elongate body; actuating the control on the handle results in the first jaw member moving towards the "closed" position (e.g., reducing the angle with respect to a line extending from the distal end of the elongate body).

The first jaw member shown in FIG. 1 also includes a suture retainer region near the distal end (described in greater detail below). This suture retainer region may hold the suture or be configured to hold a suture. In some variations the suture retainer includes a channel or guide for holding the suture in a preferred position. In some variations the suture retainer includes a pair of graspers, or deflectable members into which the suture may be pushed and held (e.g., handed off from the tissue penetrator). A suture retainer generally holds the suture so that it can be either removed by the tissue penetrator, or so that a suture can be passed into the suture retainer from the tissue penetrator. In FIG. 1, the suture retainer is a channel across which the suture extends so that it can be reliably engaged and pulled down by the tissue penetrator as described in more detail below. In some variations the second jaw member includes a suture retainer, rather than the first jaw member.

The second jaw member is shown in FIG. 1 as a lower jaw member. In this variation, the lower jaw member is configured to slide proximally towards and into the proximal elongate body of the device. The second jaw member typically moves axially, in the direction of the proximal-distal axis of the suture passer. In some variations the second jaw member moves axially completely past the distal end of the elongate body; alternatively, the second jaw member slide axially in the proximal direction only partially (e.g. to align with the hinge region of the first jaw member). The second jaw member shown in FIG. 1 retracts completely into, and extends out of, the lower portion of the elongate body. In some variations the second jaw member moves axially in parallel with the lower jaw member, or only a portion of the lower jaw member extends into the elongate body.

A tissue penetrator (not shown in FIG. 1) may be housed within either the first or second jaw member. As described in more detail below, the tissue penetrator may be configured as a needle, wire, knife, blade, or other element that is configured to extend from within either the first or second jaw members and across the opening between the jaw members to engage a suture retainer and either drop off or pick up a suture therefrom. In general, the tissue penetrator may be configured to completely retract into the jaw member housing it. It may be extended across the opening between the jaws by actuating a member in the handle to push or otherwise drive it across the opening, and though any tissue held between the jaws.

The second jaw member 105 shown in FIG. 1 completely houses the tissue penetrator and includes a deflection region that drives the tissue penetrator up and out of the second jaw member by deflecting it across the opening between the two.

The elongate body 101 shown in FIG. 1 is illustrated as a relatively straight cylindrical body, though other shapes may be used. For example, the elongate body may be curved, bent, or angled. In some variations the elongate body is configured to be bent, curved or angled dynamically (e.g. by changing the bend or curve).

The elongate body may be any appropriate length. For example, the elongate body may be between about 6 and about 24 inches long, e.g., 6 inches long, 8 inches long, 10 inches long, 12 inches long, etc. The suture passers described herein may be used for arthroscopic surgeries and therefore may be dimensioned for use as such. Thus the diameter of the device may be configured to be small enough for insertion into a cannula, tube or the like for insertion into the body.

FIGS. 2A-2D illustrate one variation of the distal end region of a dual deployment suture passer forming a distal-facing opening and extending a tissue penetrator across the distal opening. For example, in FIG. 2A the distal end of the device is shown with the first jaw member 201 (shown here as an upper jaw member) extended distally at 0° relative to a line extending from the distal end of the elongate body 203. This "straight" configuration may be helpful for inserting and/or removing the distal end of the device into the tissue (e.g., through a cannula). The first jaw member can then be bent, or allowed to bend in some variations, at an angle relative to a line extending from the distal end of the elongate body.

Figure 2A:
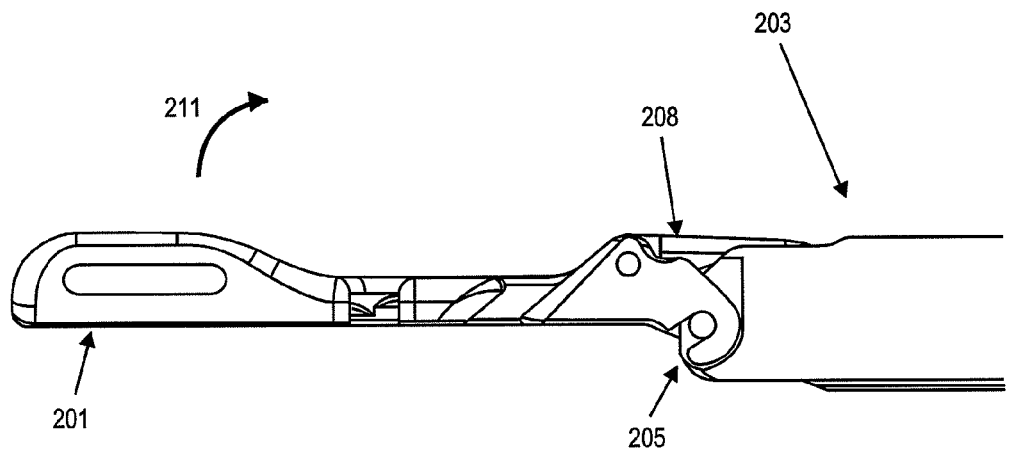
FIGS. 2A through 2D illustrate actuation of the first jaw member, second jaw member and tissue penetrator for one variation of a suture passer.

In this example, the first jaw member pivots around an hinge point 205, and is controlled by a pulling member 208 that pushes and/or pulls proximally and/or distally to control the bend of the first jaw member. The pulling member may include a shaft, wire, tendon, tube, cannula, or the like, and may extend to the proximal end of the device where it can be controlled. The arrow 211 in FIG. 2A illustrates the plane and direction of motion of the first jaw member.

Figure 2B:
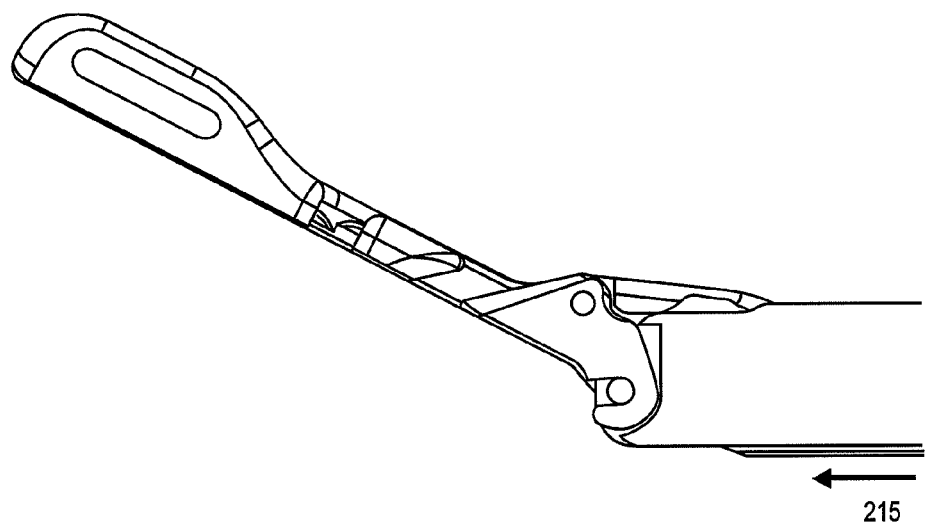
Figure 2C:
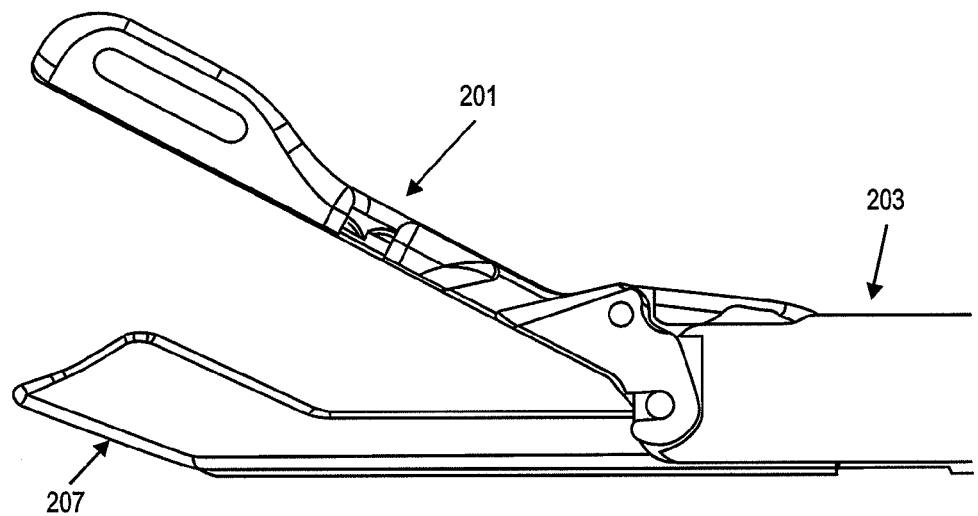

In FIG. 2B the first jaw member has been moved (or allowed to move) so that it forms an angle of approximately 30° with a line extending from the distal end of the elongate body. The arrow 214 in FIG. 2B illustrates the direction of axial motion that the lower jaw (not yet visible in FIG. 2B) will be moved. This is illustrated in FIG. 2C, in which the lower jaw member 207 has been extended distally from the proximal region of the device. In this example the second jaw member 207 is shown fully extended distally relative to the elongate body region 203. Although this example shows the second jaw member extending from completely within the elongate body region (as in FIG. 2B), in some variation the lower jaw member is held outside of the elongate body region, or only partially within the elongate body region. In some variations the second jaw member is completely retracted proximally so that much (or all) of the second jaw member is held proximal to the distal end of the elongate body region 203.

Figure 2D:
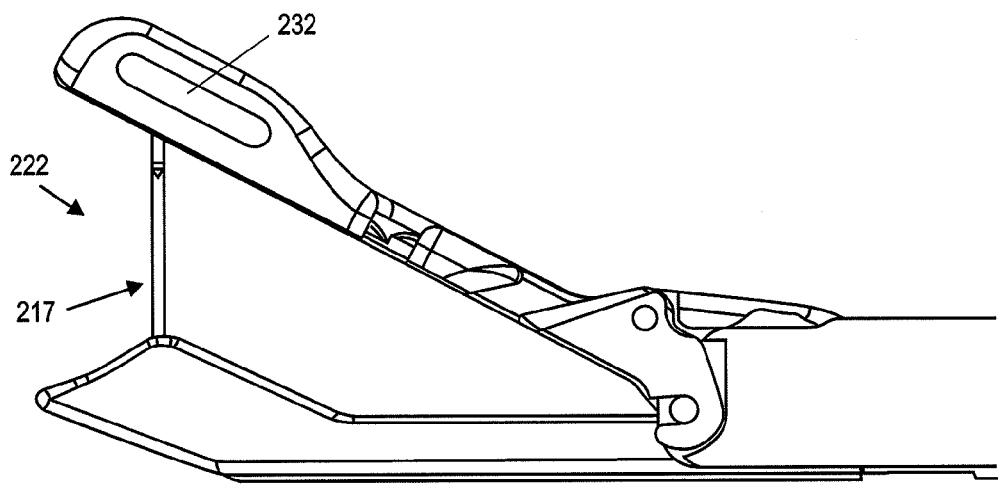

Once the first and second jaw members are completely extended distally (as shown in FIGS. 2C and 2D, the tissue penetrator may be sent across the distal-facing opening 222 as shown in FIG. 2D. In general, the tissue penetrator may be prevented from exiting the opposite side of the jaw member by a limiter (e.g. a travel limiter and/or a movement limiter). In FIG. 2A-2D the first jaw member includes a cage or shield region 232 that prevents the tip of the tissue penetrator from extending out of the first jaw member where it may cut or damage the non-target tissue. In some variations the device may also include a movement limiter, which limits the movement of the tissue penetrator so that it can only extend to just couple with the opposite jaw member (and pass or grab a suture held therein). Since the jaws may be open to varying positions, a movement limiter may help prevent the tissue penetrator from overextending even when the first jaw member is only slightly angled with respect to a line extending from the distal end of the elongate body.

In some variations the tissue penetrator may be prevented from extending across the opening between the first and second jaw members unless the second (axial moving) jaw member is extended distally relative to the elongate body. This may allow the tissue penetrator to mate properly with the suture engagement region on the first jaw member. For example, a lock or other mechanism may be used to prevent the tissue penetrator from engaging with a control at the proximal end of the device until the second jaw member is fully extended.

A side view of the device shown in FIGS. 1-2D is provided in FIG. 3.

FIG. 4 shows a front perspective view of the distal end region of the device of FIGS. 1-3 with the second jaw member extended fully distally and the first jaw member angled slightly (e.g., approximately 30° relative to a line extending distally from the longitudinal axis of the elongate body). In this variation the lower jaw member 403 may be configured to fit within the upper jaw member 401 when the two jaw member s are closed down on one another (not shown). Thus the upper (first) jaw member 401 is wider than the lower (second) jaw member 403. The first jaw member in this example also includes optional side windows 402. The first jaw member may also include a suture engagement region; in FIG. 4, this suture engagement region includes a channel 409 through the midline (extending proximally to distally) and a first 415 and second 417 notch or protrusion 405 cut into the first jaw member. A suture may be wrapped around the first jaw member by passing from the proximal end of the device, under the proximal notch 417 and along the bottom (e.g., the side of the first jaw facing the extended second jaw) around the distal end of the first jaw member and along the top (e.g., the side of the first jaw facing away from the second jaw) and, under the distal notch 415 and back up out of the proximal notch 417 so that the suture may extend distally. This loop of suture held by the suture engagement region of the jaw member may be held under sufficient tension so that the suture may be engaged by the suture engagement region of the tissue penetrator (e.g., hook, grasper, etc.). In some variation a tensioning member may be included in the suture engagement region.

In some variations (not shown here) the suture may be contained within the elongate body of the device. Alternatively, the suture may be kept outside of the device. In some variations the suture may be loaded by the user. For example, a user may load a suture on the device by placing a loop of suture over the first jaw member. In some variation suture holder may be placed along the length of the device to hold or manage the suture so that it doesn't interfere with the operation of the device or get tangled.

Figure 5A:
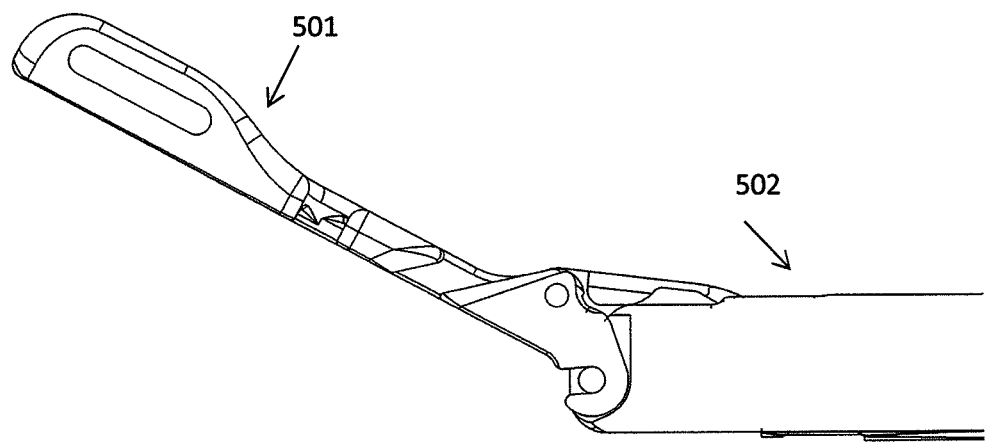
FIG. 5A is a side perspective view of the suture passer variation shown in FIG. 4 with the second jaw member retracted proximally.
Figure 5B:
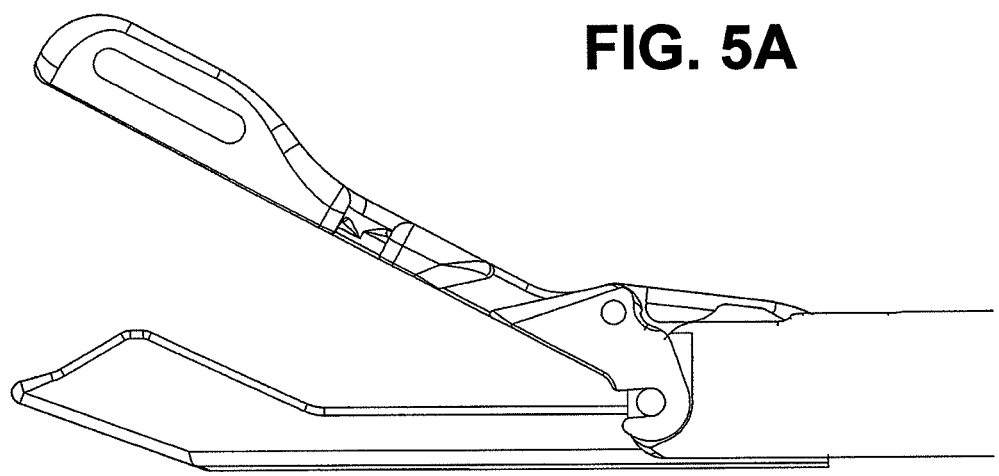
FIG. 5B shows the suture passer of FIG. 5A with the second jaw extended distally.
Figure 5C:
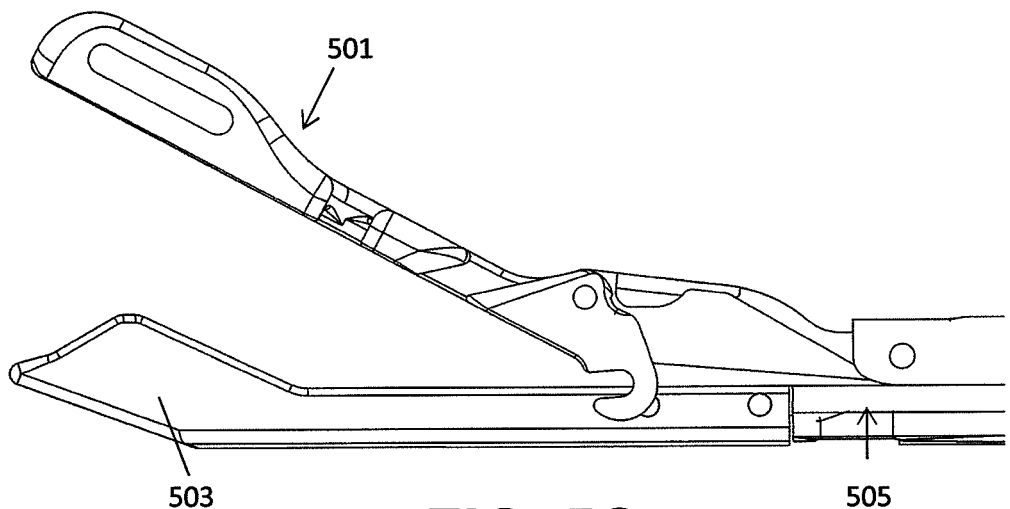
FIG. 5C shows FIG. 5B with the outer region of the elongate body removed.
Figure 6A:
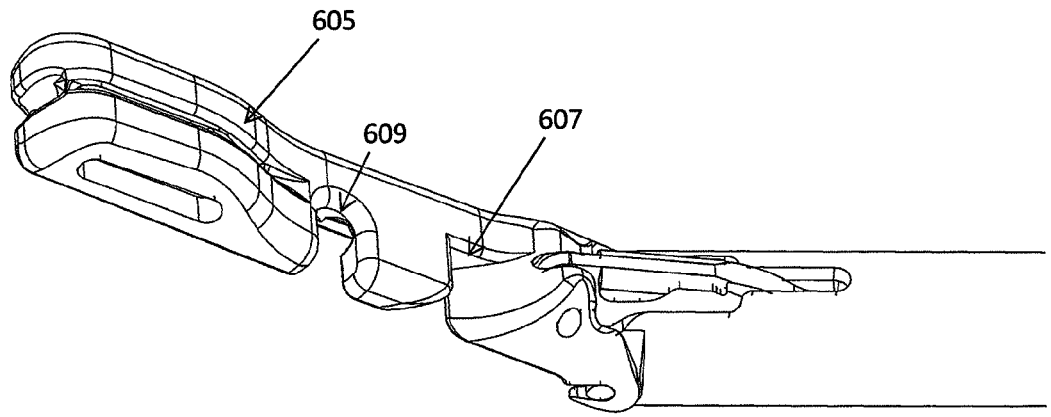
FIG. 6A shows a top perspective view of the suture passer shown in FIG. 5A.

FIGS. 5A-5C and 6A-6C illustrate different views of the first and second jaw members in one variation. For example, in FIG. 5A the first jaw member is shown with the second jaw member retracted proximally. FIG. 6A shows a top perspective view of the same first jaw member shown in FIG. 5A. In FIG. 6A, the first jaw member includes a channel 605 extending along the longitudinal length of the first jaw member; this channel may form part of the suture engagement region. The channel may hold the suture so that it extends along the midline of the first jaw member on the underside of the first jaw member. The notches 607, 609 in the first jaw member near the proximal end extend toward the midline of the first jaw member and allow the suture to pass from the top of the first jaw member to the bottom and back out, as discussed above. Thus, the suture may be held close to the elongate body of the device even when the first jaw is open to various angles.

Figure 6B:
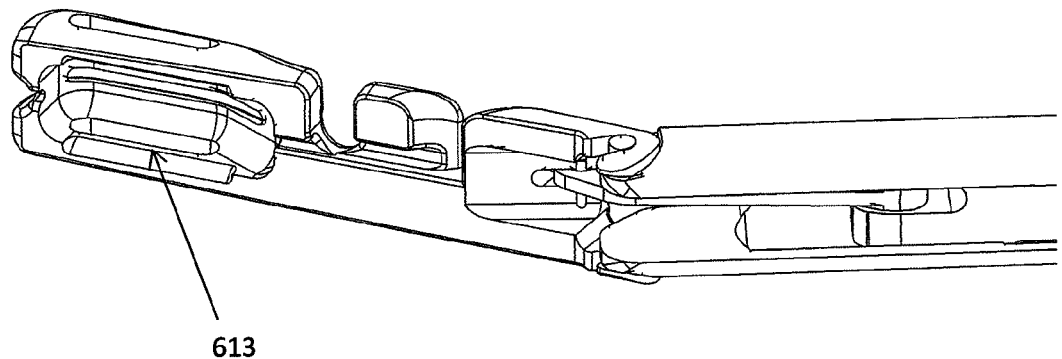
FIG. 6B shows a bottom perspective view of the suture passer of FIG. 5B.
Figure 6C:
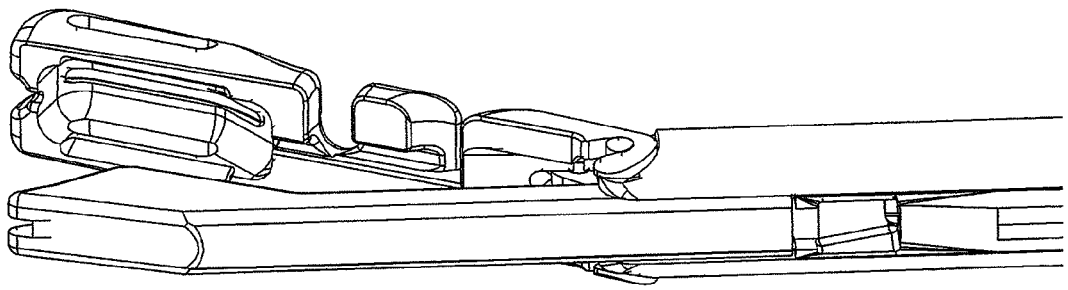
FIG. 6C shows a bottom perspective view of the suture passer of FIG. 5C.

FIG. 6B illustrates the underside or bottom of the first jaw member shown in FIG. 6A. The suture management region is the entire opening formed at the distal end. This cavity 613 is surrounded by the inside of the first jaw member, and (as mentioned above) may act as a limiter to limit the tip of the tissue penetrator from extending outside of the first jaw member. FIG. 6C shows the same view as in FIG. 6B, but with the second jaw member axially extended distally.

Returning now to FIG. 5B, a side view of the distal end of one variation of a suture passer is shown with the second jaw member 503 extended distally. FIG. 5C shows the same view as in FIG. 5B but with the outer cannula 502 covering for the elongate member removed, showing the connection between the second jaw member and the pushing/pulling element (rod 505). The pushing/pulling element may be a wire, shaft, tendon, or the like, allowing the second jaw member 503 to be controllably slid distally and proximally. Not visible in FIGS. 5A-6C is the tissue penetrator, which is fully retracted into the second jaw member in this exemplary embodiment.

FIG. 7A shows one variation of a tissue penetrator 700 as described herein. In this example, the tissue penetrator includes a sharp, pointed distal tip 701 and just proximal to the distal tip is a suture engagement region configured as a hooked cut-out region 703. The proximal end of the tissue penetrator includes a coupling region for coupling the tissue penetrator with a pusher/puller mechanism, such as a shaft, rod, wire, tendon, or the like.

FIG. 8 shows the same perspective view of FIG. 4, but with the tissue penetrator 803 partially extended across the distal-facing opening formed between the first jaw member 801 and the second jaw member 803. A suture 808 is looped around the first jaw member 801. Both ends of the suture pass into the notched region and are held close to the elongate body, allowing the loop of suture to be held in tension within the suture engagement region.

Figure 9A:
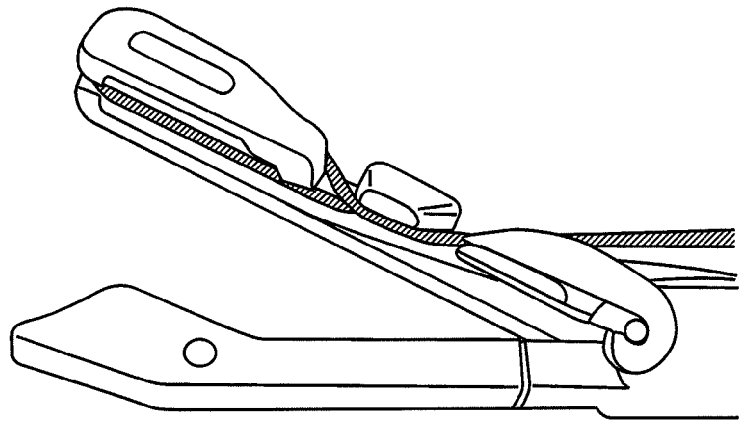
FIGS. 9A-9C illustrate actuation of a suture passer such as the one shown in FIG. 8 to pass a suture from the upper jaw to the lower jaw.
Figure 9B:
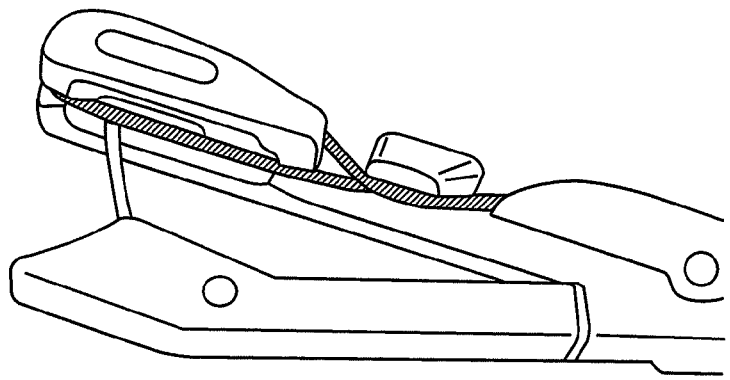
Figure 9C:
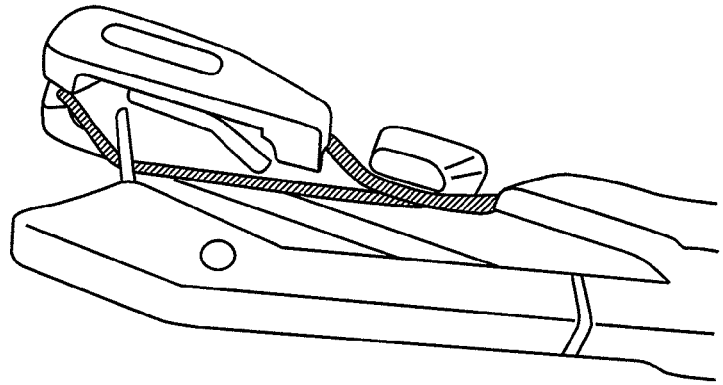

FIG. 9A-9C illustrate the variation of the device described above passing a suture from the first jaw member to the second jaw member. In FIG. 9A, the distal end of the second jaw member for the dual deployment suture passer has been extended fully. The upper jaw is held at an angle relative to the elongate body region of the device proximal to the joint (e.g., hinge, bend region, etc.) of the first jaw member. A suture has been loaded into the suture engagement region, and extends along the length of the midline of the first jaw member. In FIG. 9B, the first jaw member has been moved slightly (decreasing the angle between the first jaw and the fully extended lower jaw member. This may be typically of situations in which tissue is held between the first and second jaw members. Clamping the tissue to be sutured in this manner allows the tissue to be secured within the jaws, preventing it from moving undesirably, and helping the tissue penetrator to penetrate through the tissue. Further, in FIG. 9B the tissue penetrator has been extended from the lower second jaw member across the distal-facing opening, towards the first jaw member and the suture retained therein. Once the tissue penetrator contacts the suture, it may be grabbed or otherwise engaged by the suture engagement member of the tissue penetrator. Thereafter, the suture can be pulled back down with the tissue penetrator as it retracts back into the second jaw member. In this variation, the loop of suture is pulled back through the tissue.

Although the variation of the suture passer shown and discussed above includes relatively straight first and second jaw members, other configuration of jaw members is possible. For example, FIGS. 10A and 10B illustrate two variations of the upper jaw member. In particular, FIG. 10B shows a variation in which the straight jaw member of the first jaw member is instead a curved jaw member; the curve may allow a greater thickness of tissue to be placed between the jaws and may also be useful for navigating certain tissue regions, such as the labrum and ACL.

Figure 11:
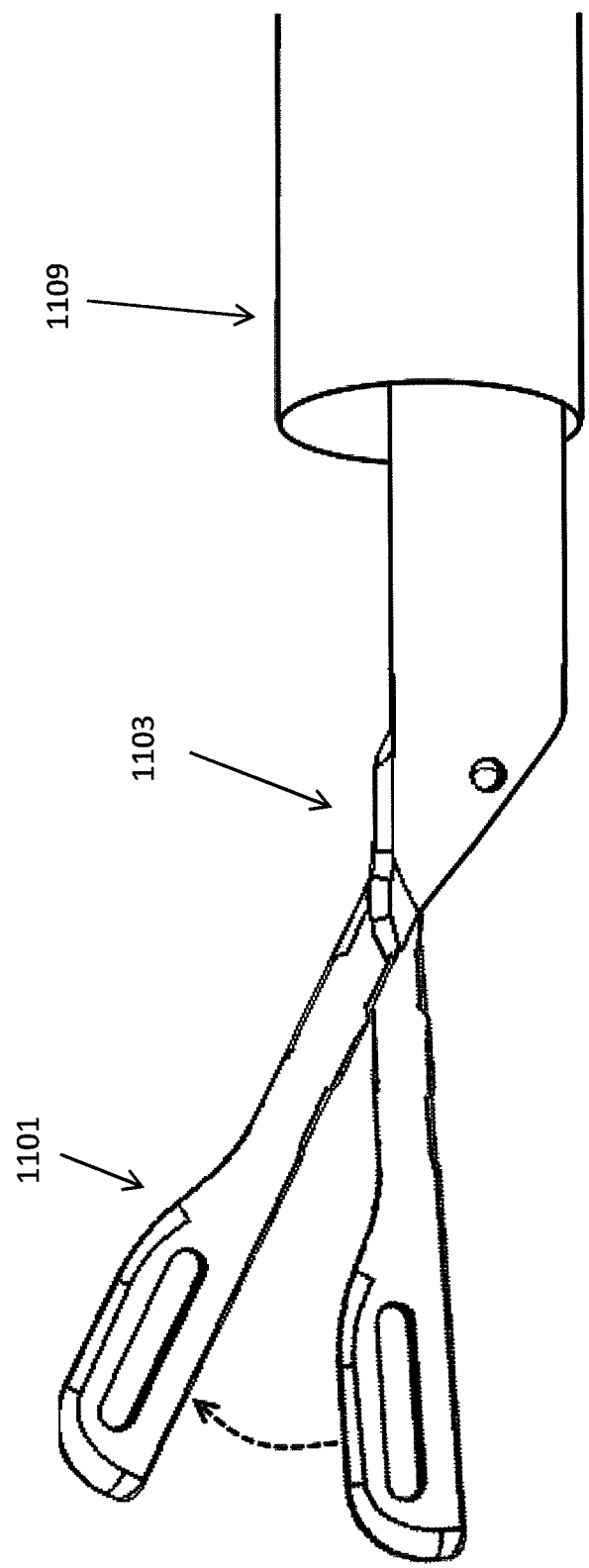
FIG. 11 illustrates one variation of a first jaw member having a hinge allowing angular motion relative to the long axis of the elongate member region of the suture passer.

In general, the first jaw member in many of the variations described herein may be dynamically angled with respect to the elongate body of the device. The first jaw member may be connected to and extend from the distal end of the elongate body, or may be connected to an intermediate region between the elongate body and the first jaw member. For example, in FIG. 11, a first jaw member is hinged to the elongate body, so that it can be controllable moved to change the angle between with the elongate body long axis. The first jaw member hinge 1103 thus allows the position of the first jaw member 1101 to be adjusted (e.g., more opened or closed) as device is positioned within the body towards a desired tissue to be sutured. This adjustability may allow the suturing device to be inserted further into the space, hence farther from any insertion cannula 1109. This scissoring jaw mechanism, in combination with the absence of a second (lower) jaw member, which may be retracted proximally, enables the device to surround a target tissue without being trapped within the cannula 1109 opening (the jaws don't have to be opened as traditional jaws would be) as it is being positioned.

Figure 12A:
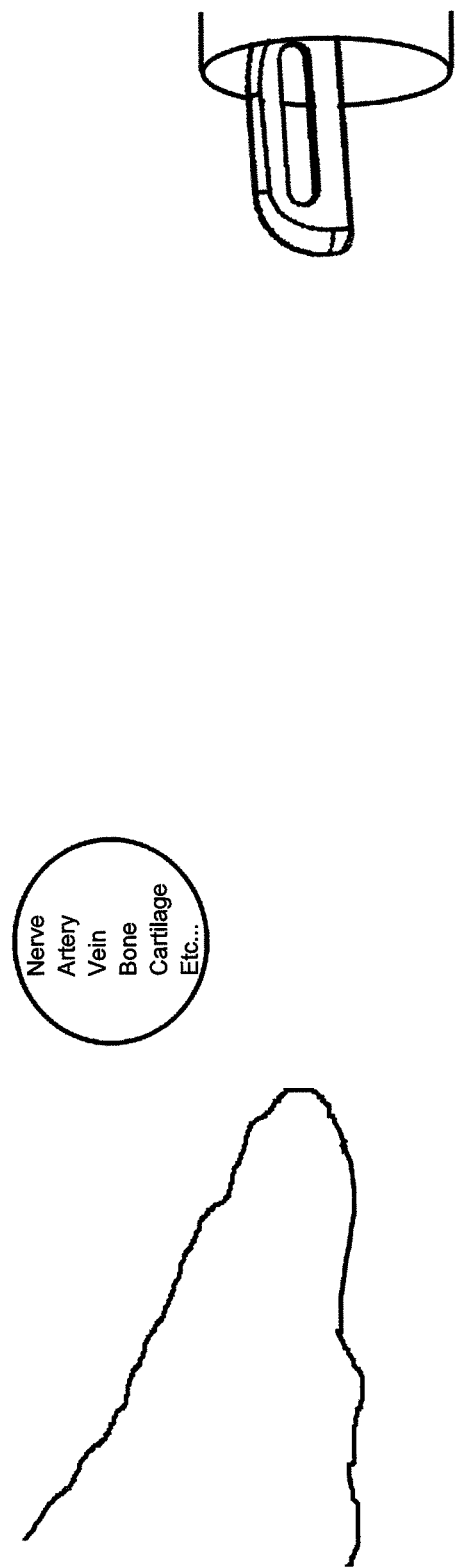
Figure 12C:
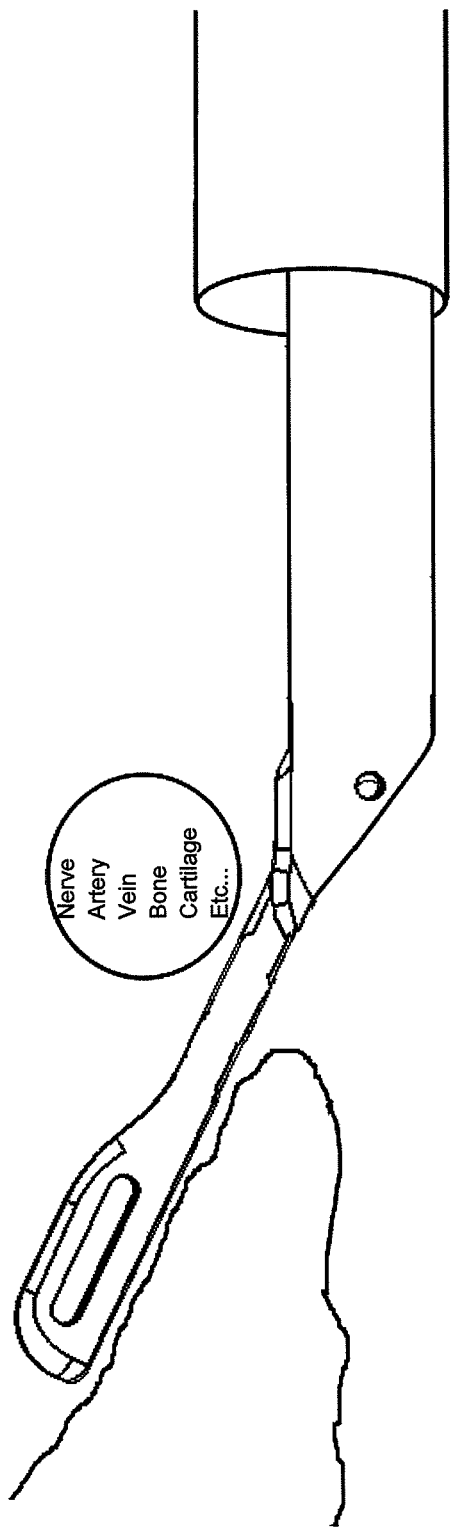
Figure 12D:
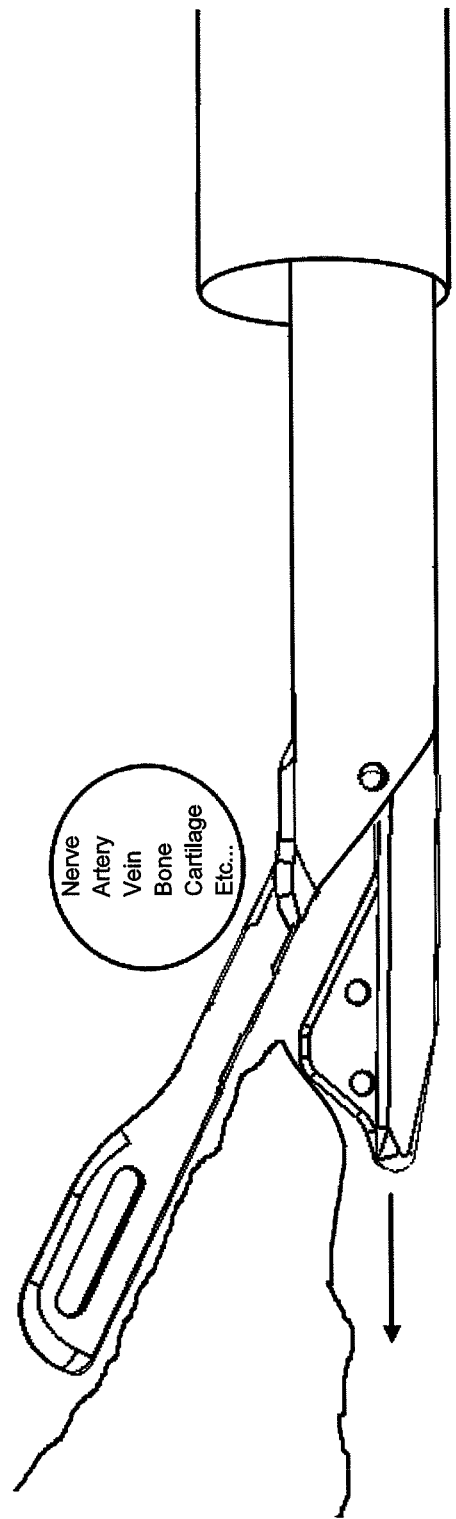
Figure 12E:
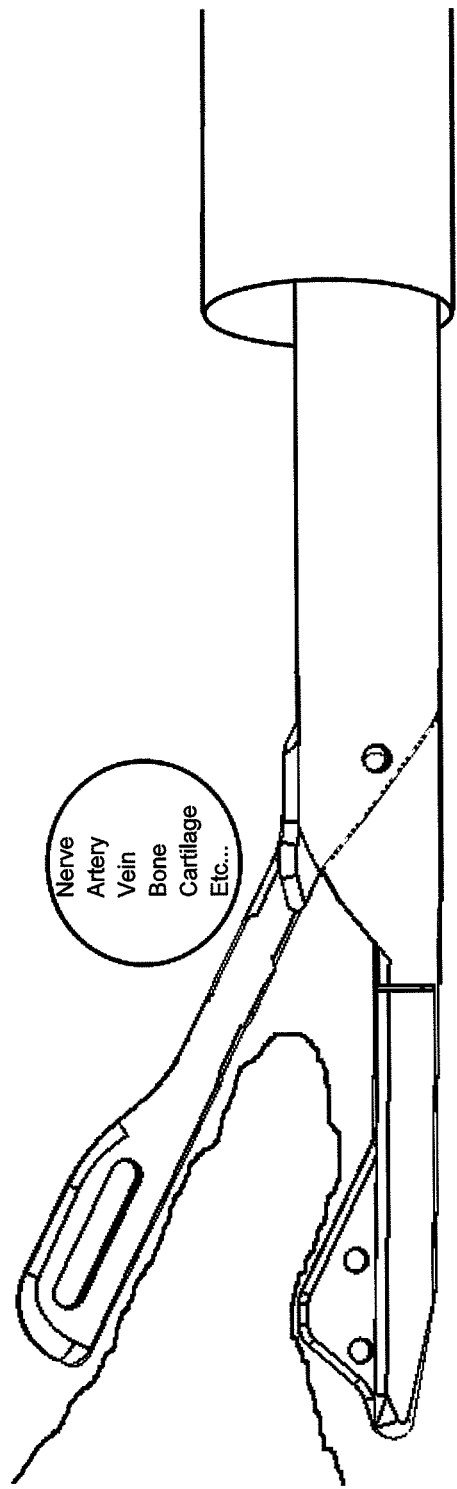

For example, FIGS. 12A-12E illustrate one variation of the operation of a dual deployment suturing device in which the first (upper) jaw member is hinged and the second (lower) jaw member slides axially relative to the elongate body region proximal to the first jaw member. This design allows the device to surround tissue in difficult to reach areas, while at the same time protecting nearby tissue from iatrogenic damage. In FIG. 12A a cannula has been placed within the body near the target tissue. Non-target tissue to be avoided is also nearby. For example the non-target tissue region may be a nerve, an artery, a vein, bone, cartilage, etc. In FIG. 12B, the suturing device is extended from the cannula with the distal end of the first jaw member leading. The first jaw member may be held in a horizontal position (at an angle of 0° relative to the long axis of the elongate body). In this example, the second jaw member is retracted proximally and is therefore kept out of the way of the distal end region of the device as it is positioned near the target tissue. In FIG. 12C the first jaw member is angled "up" (at an angle of about 30° with respect to the long axis of the elongate body) allowing the device to maneuver around the potentially sensitive non-target tissue so that it can be positioned adjacent to the target tissue. All of these maneuvers may be performed with the help of visualization, such as arthroscopic visualization. In FIG. 12D, once the first jaw member is adjacent to the tissue, the second jaw member may be distally extended by moving axially from the distal end of the elongate body, as shown. This motion of the second jaw member may also be referred to as a telescoping motion, as it is extending out of the proximal region toward the distal end by axially sliding. As the second jaw member extends distally it surrounds the tissue between the first and second jaw members, forming a distal-facing opening in which the target tissue resides, as shown in FIG. 12E. Thereafter, the tissue penetrator may be extended between the first and second jaw members, allowing the tissue penetrator to pass the suture from the first to the second jaw member. When the suture has been passed and the tissue penetrator retracted back into the second jaw member, the second jaw member may be retracted back towards the elongate member, proximally, and the entire device withdrawn from the tissue or away from the target tissue. The suture passing through the tissue may then be knotted or otherwise anchored.

Figure 13A:
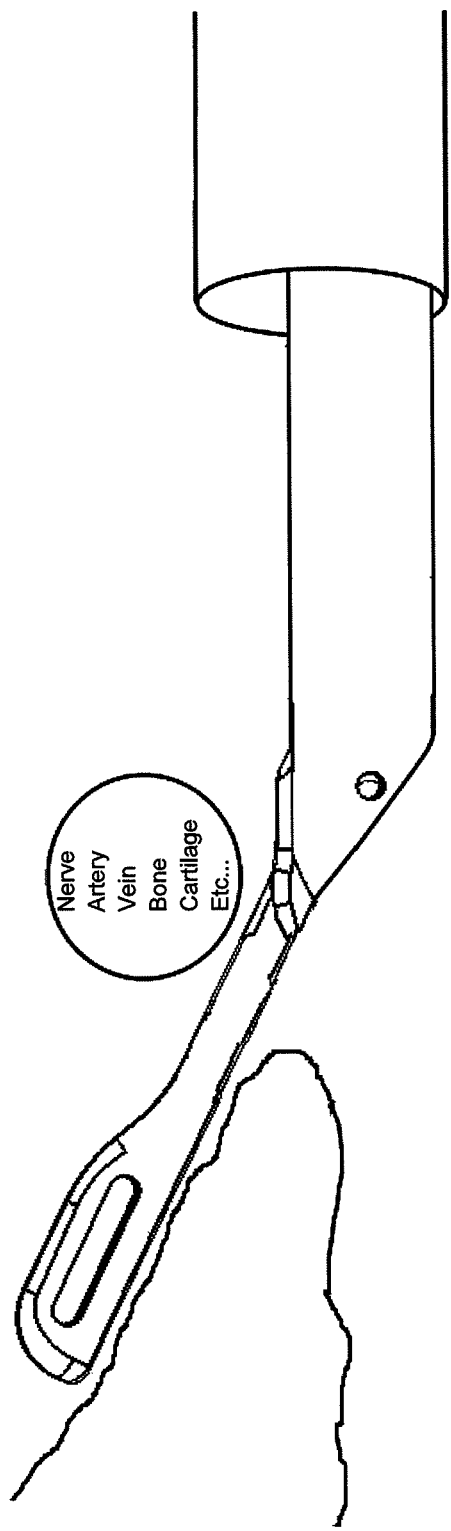
Figure 13C:
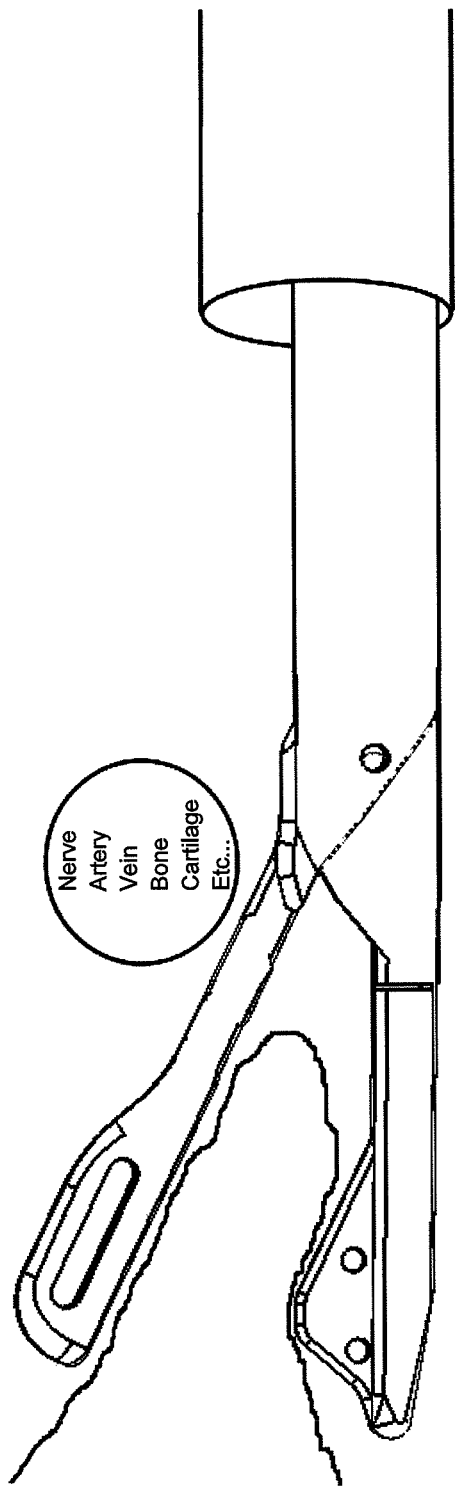

FIGS. 13A to 13C illustrate operation of another variation of a suture passer in which the second jaw member is a side swinging member. In this variation the second jaw member extends from the proximal portion (e.g., behind the first jaw member or the hinge of the first jaw member) to distal position by a side swinging motion. Although this motion would not be permitted everywhere in the body, there may be some variations in which this side swinging motion may be desired.

Figure 14A:
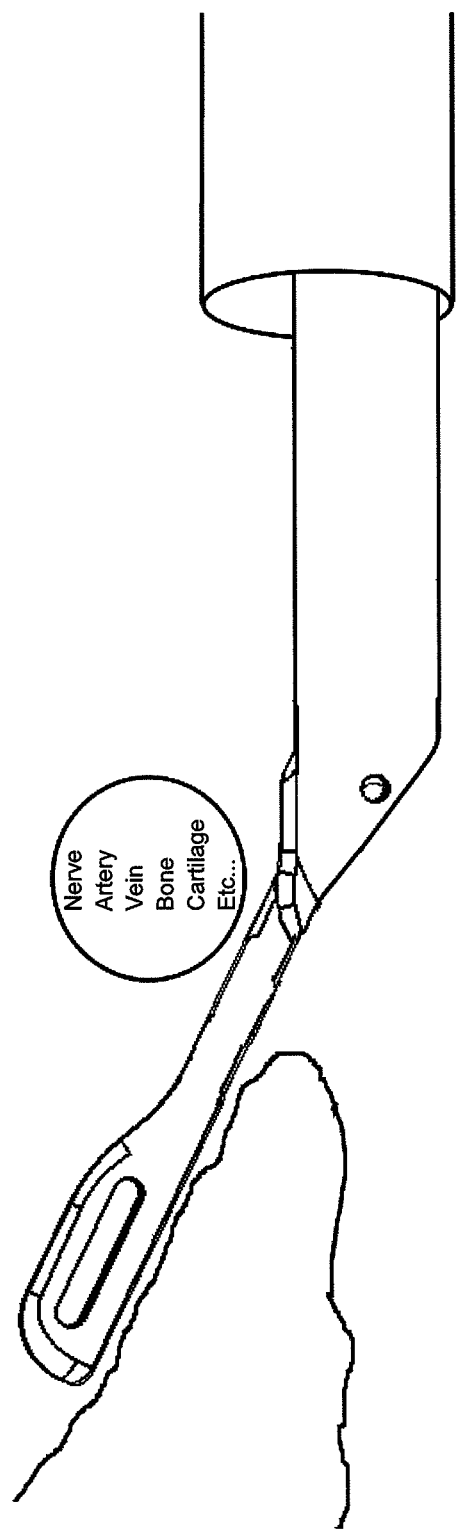
FIGS. 14A-14C illustrate operation of one variation of a dual deployment suture passer configured as a clamping/down-swinging suture passer.
Figure 14B:
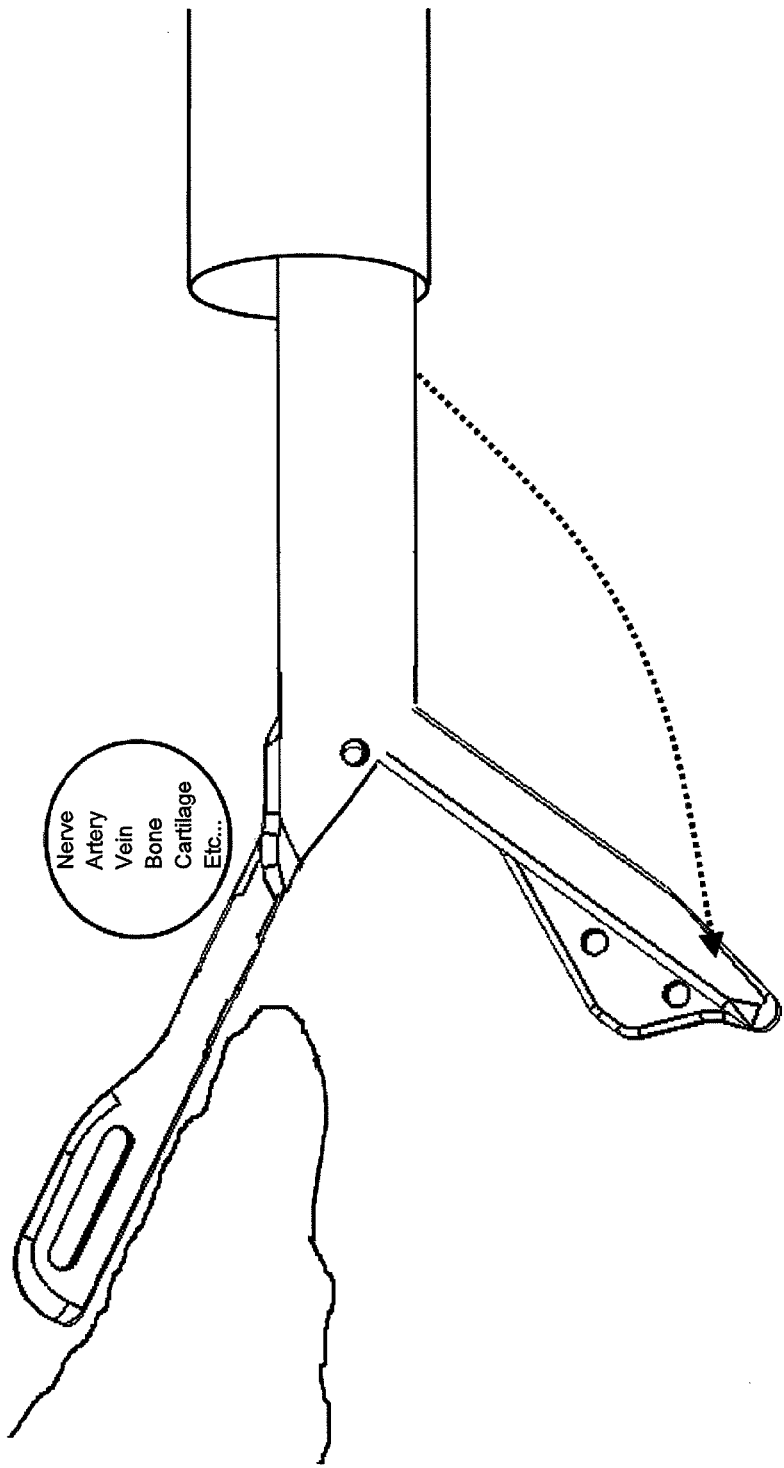
Figure 14C:
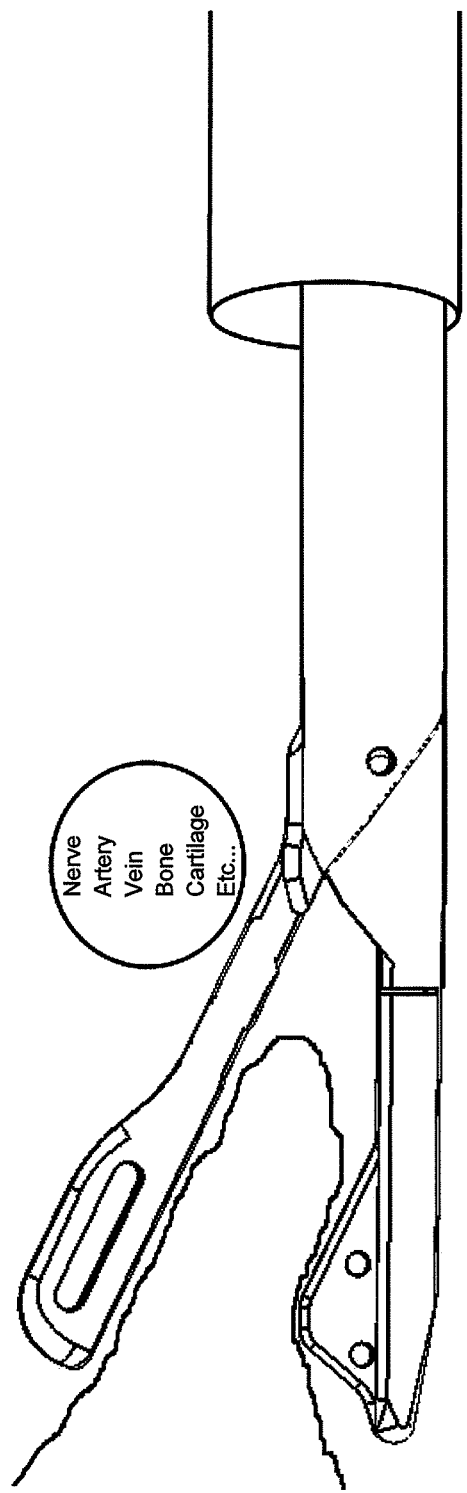

FIGS. 14A-14C illustrate operation of another variation of a suture passer having a first jaw member that swings from a proximally located position (e.g., proximal to the upper jaw) to a distal position able to form a distal-facing jaw opening with the first jaw member. In this variation the second jaw member swings down (away from the long axis of the device) and back up to be positioned distally and opposite the first jaw member as shown in FIGS. 14B and 14C.

Figure 15A:
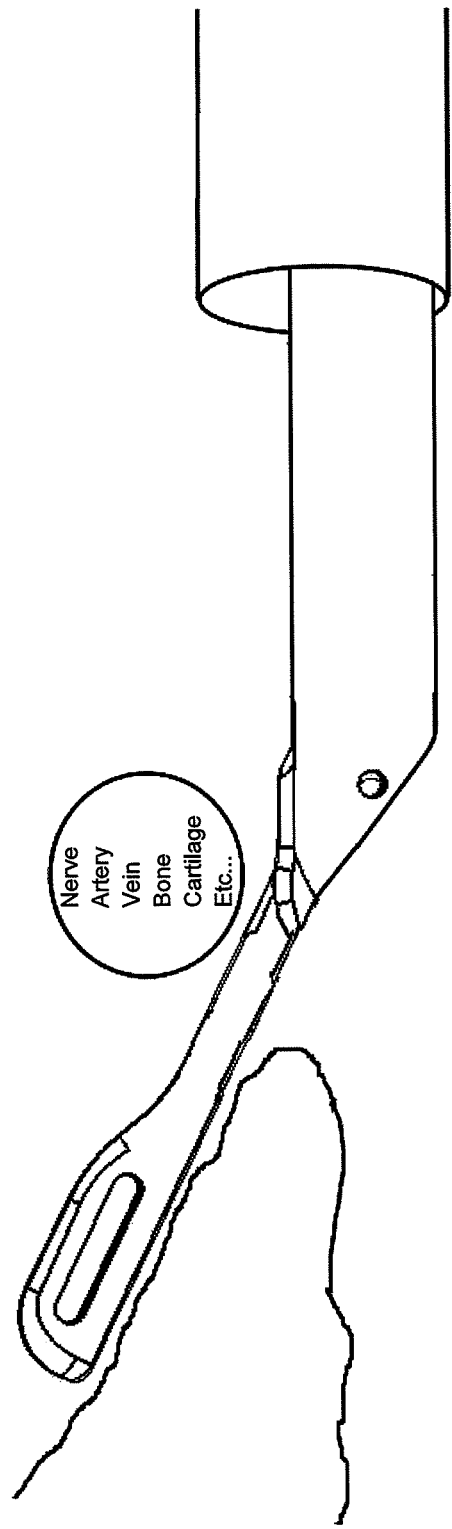
FIGS. 15A-15C illustrate operation of one variation of a dual deployment suture passer configured as a clamping/complex motion suture passer.
Figure 15B:
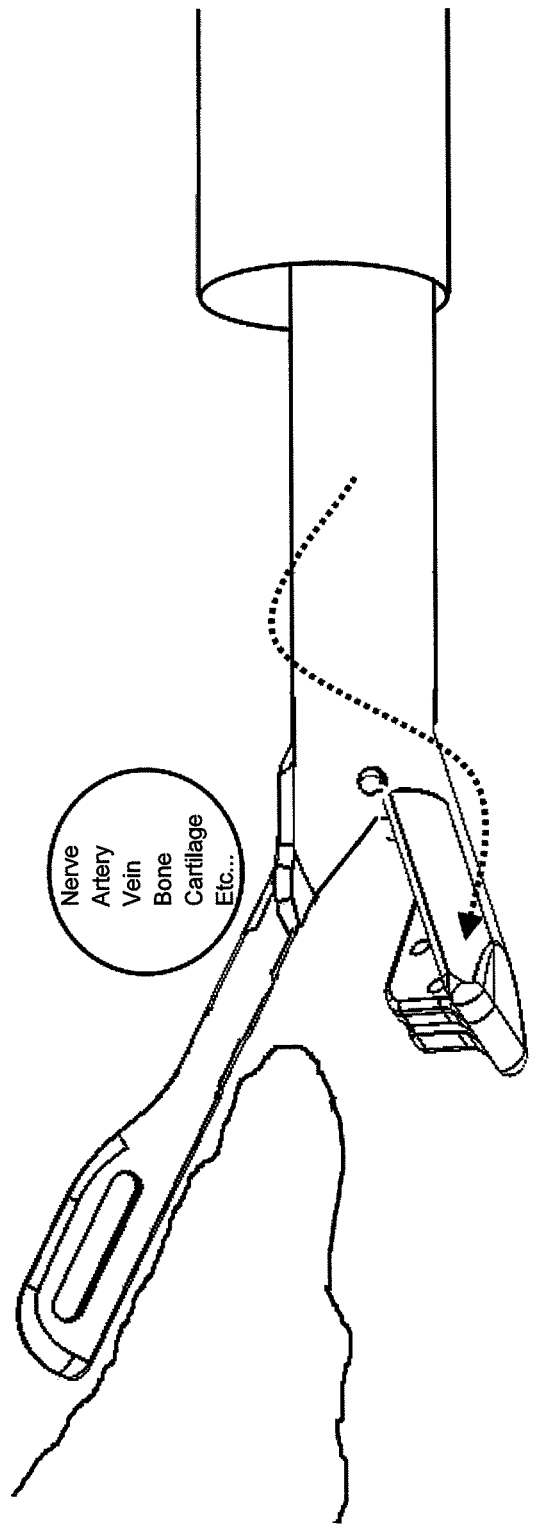
Figure 15C:
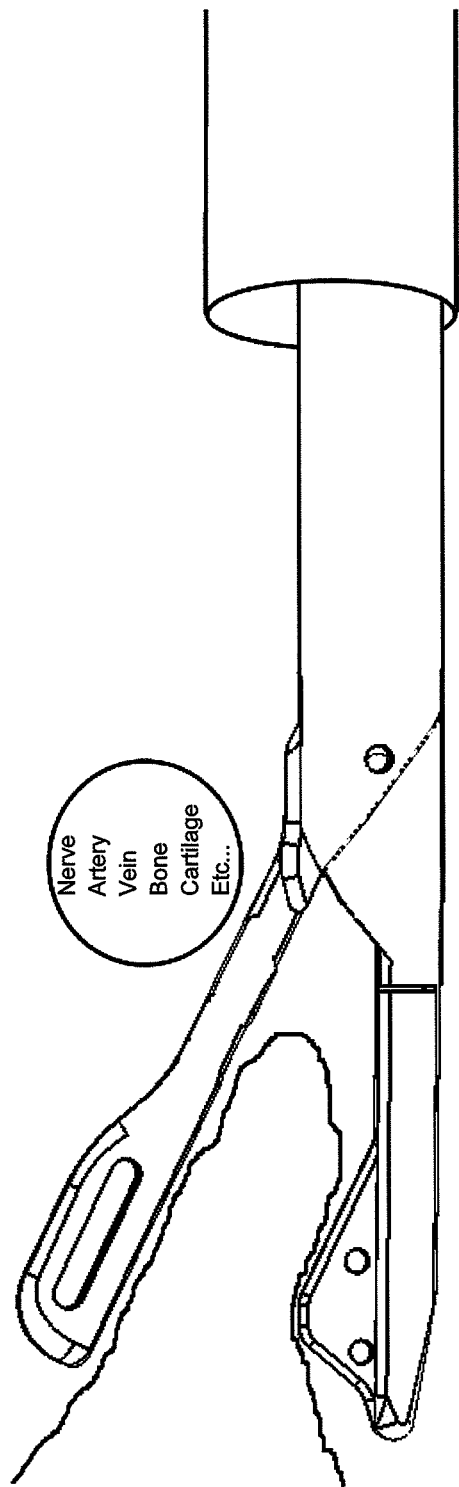

Other variations of motion of the second jaw member are possible, including compound motions that combine more than one of the axial motion, side-swinging motion and down-swinging motion. For example, FIGS. 15A-15C illustrate a second jaw member having a compound or composite motion. In any of these variations, the second jaw member typically goes from a retracted position in which it is held proximal to first jaw member and/or proximal to the distal end of the elongate body, to an extended distal direction.

Figure 17A:
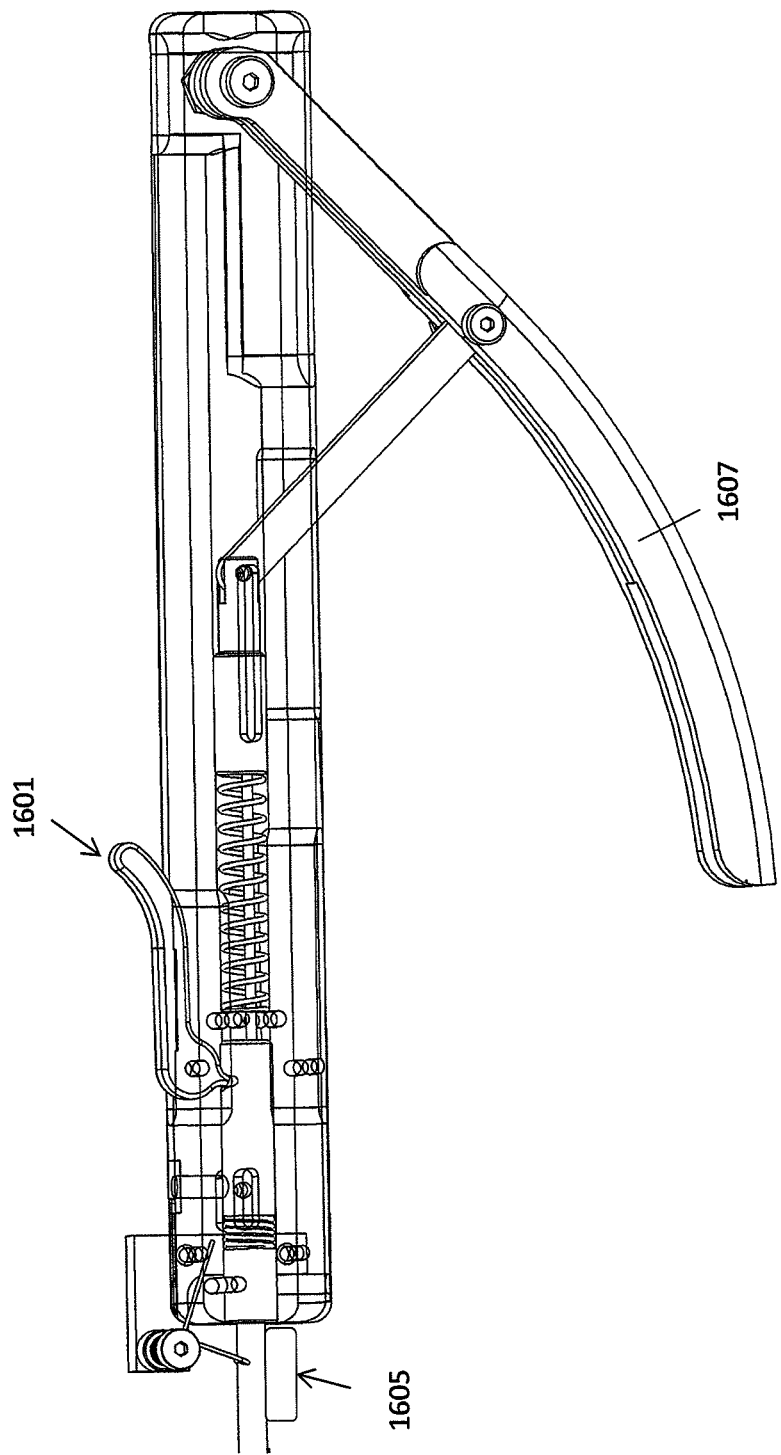
FIG. 17A shows one variation of a proximal handle with controls for controlling action of a dual deployment suture passer.

The position of the first jaw member and the second jaw member may be separately and/or independently controlled. For example, any of the variations described herein may include a proximal handle having controls for controlling the activation of the first jaw member, the second jaw member, and the tissue penetrator. For example, FIG. 17A is an enlarged view of the handle region of the suture device discussed above in FIGS. 1-3. In this example, the handle includes a control to control the motion of the first jaw member (which may also be referred to herein as a clamp trigger) 1603, a second jaw member control 1605 (or lower jaw handle), and a tissue penetrator control 1607 (or needle trigger). Additional controls may include a lower jaw screw lock to lock the position of the law jaw member. The operation of this handle variation in controlling a dual deployment suture passer is described below with respect to FIGS. 19A-19F.

Figure 17B:
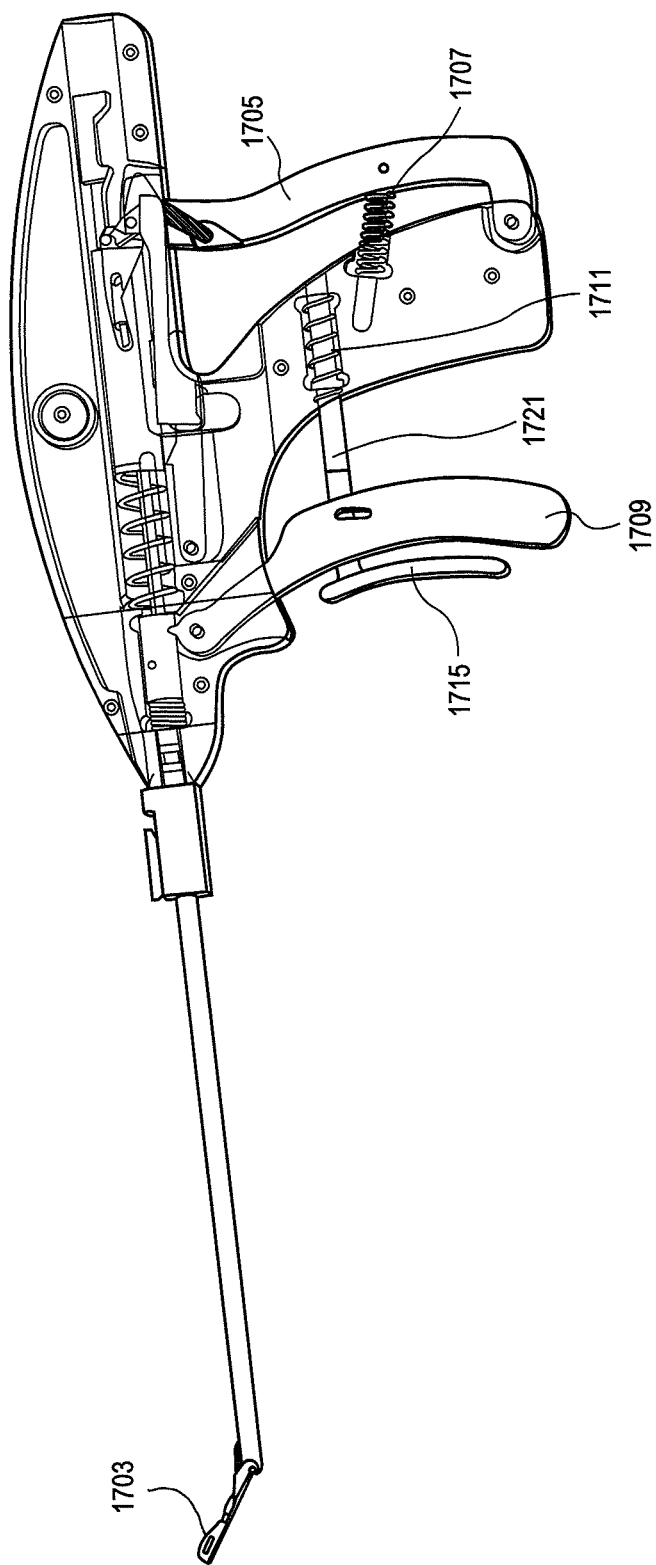
FIG. 17B shows another variation of a proximal handle with controls for controlling action of a dual deployment suture passer.

FIG. 17B illustrates another variation of a handle for a dual deployment suture passer. In this variation the handle controls are triggers/handles. The proximal trigger 1705 is a squeeze handle that controls the angle of the first jaw member 1703 relative to the elongate body. The control and handle are configured with a bias element (spring 1707) that tends to keep the first jaw member at an angle with respect to the elongate member; in this example, the angle is about 30° relative to a line extending distally from the long axis of the elongate body region of the device. A second grip control 1709 controls the extension of the second (lower) jaw member (not visible in FIG. 17B). In this variation a second biasing element (spring) 1711 tends to hold the control so that the second jaw element is retracted proximally and, in this example, into the elongate member. A third trigger control 1715 controls the extension of the tissue penetrator. This control is arranged to include a lock that prevents the control from engaging with the tissue penetrator until the second jaw member is completely extended. Further, the control also includes a travel limiter 1721 that limits how far the tissue penetrator may be extended from within the second jaw element based on how angled the first jaw member is, preventing the tissue penetrator from trying to extend beyond the first jaw element.

In any of the devices described herein, the controls may be handles or triggers (as illustrated in FIGS. 17A and 17B) or other controls, such as dials, buttons, sliders, switches, or the like.

Figure 16A:
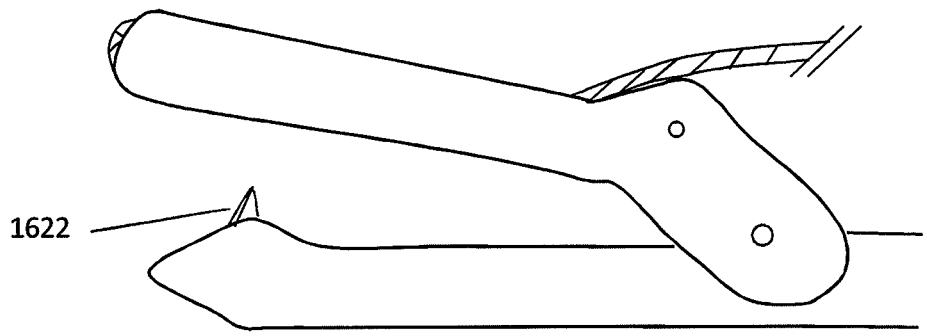
FIGS. 16A-16C illustrate another variation of a dual deployment suture passer configured so that the distal end of the tissue penetrator extends distally from the first jaw.
Figure 16B:
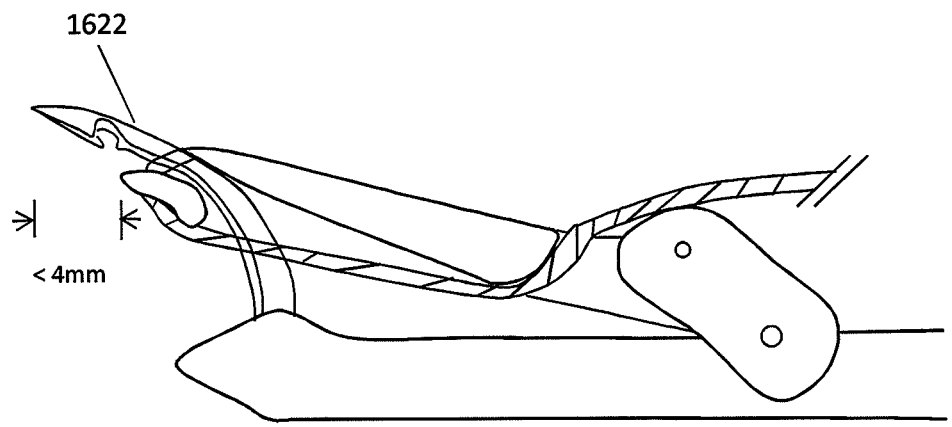
Figure 16C:
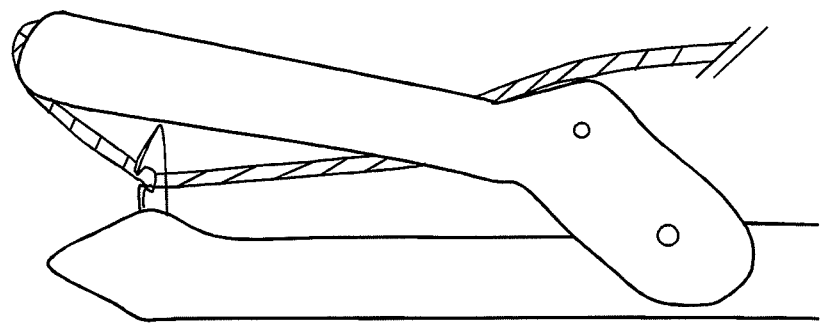

Although many of the suture passer devices (including the dual deployment suture passers described above) limit the travel of the tissue penetrator to prevent it from extending beyond the opposite jaw member from where it is housed when not extended, in some variations it may be beneficial to allow the tissue penetrator to extend distally out of the opposite jaw member, as illustrated in FIGS. 16A-16C. In this example the tissue penetrator is deflected within the opposite jaw member and allowed to extend distally out of the opposite jaw member some amount (e.g., less than 5 mm, less than 4 mm, less than 3 mm, etc.). For example, as shown in FIG. 16A, the tissue penetrator may be housed in the second jaw member and may be deployed across the distal-facing opening formed when the first and second jaw members are extended fully distally. The tissue penetrator is shown partially extended from the second jaw member in FIG. 16A, however it should be understood that the tissue penetrator (including the tip of the tissue penetrator) may be fully retraced or retractable into the second jaw member. Also, for convenience in FIGS. 16A-16C, the jaw members are shown close together, e.g., with only a little space between the first and second jaw members; the jaws may be more opened, for example, by moving the first (upper) jaw member at an angle with respect to the more proximal region of the device.

In FIG. 16B the tissue penetrator 1622 extends from within the second jaw and across the distal-facing opening to pass into an opening on the opposite (first or upper) jaw member. The tip of the needle is pointed in this example, and a side region of the needle proximal to the pointed distal tip is recessed to form a suture engagement region that is hook-shaped. Extending the needle into and partially out of the first jaw member as shown in FIG. 16B allows the suture engagement region on the tissue penetrator to engage the suture held by the first jaw member, as shown. The tissue penetrator in this example extends out of the distal end of the first jaw member distally (not laterally) and is limited to extending just a finite amount (e.g., less than 4 mm) from the distal tip of the first jaw member. In FIG. 16C, the tissue penetrator is retracted back to the second jaw member, pulling the suture with it in the suture engagement region.

The variation of the suture passer illustrated in FIGS. 16A-16C in which the tip of the tissue penetrator extends distally, has various features or advantages including simplifying the coordination between the various parts. For example, less coordination is required to limit the needle motion (e.g., stopping it before it crashes into the first or upper jaw). This may allow greater tolerances, and the parts may require less precision. Also, extending the tissue penetrator distally may allow for "over travel" of the tissue penetrator and provide for more reliable engagement (hooking) of the suture by the suture engagement region. The distal end of the first jaw member may include sufficient space for the tissue penetrator to over-travel the suture so that the hook (suture engagement feature) on the tissue penetrator can grab the suture on its way back to the lower (second) jaw member. With this variation, the height of the first jaw member can be compressed sizably, and the over-travel necessary to pick up the suture is directed in a manner that doesn't require additional height. Further, the additional over-travel opportunity offered by this configuration may allow use of a symmetric distal tip region for the suture penetrator, e.g., having a point is in the middle of the tissue penetrator distal tip region. Asymmetric tissue penetrators may also be used (e.g., having a point is on one side of the tissue penetrator). However, the asymmetric tissue penetrators may have a greater propensity to deviate from the desired needle trajectory towards the direction of the needle point.

Figure 18A:
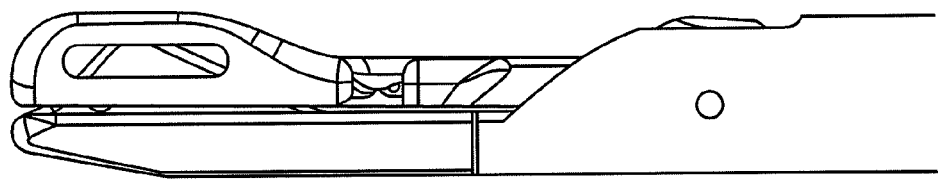
FIGS. 18A-18C show another variation of a suture passer as described.
Figure 18B:
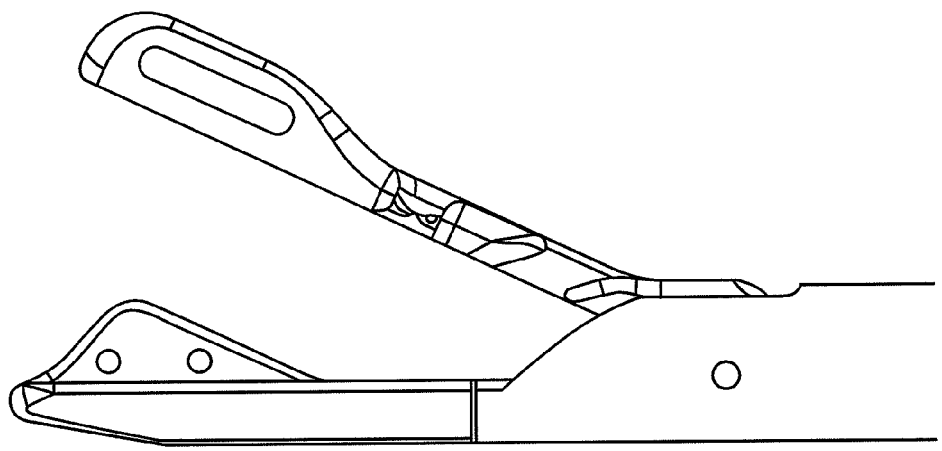
Figure 18C:
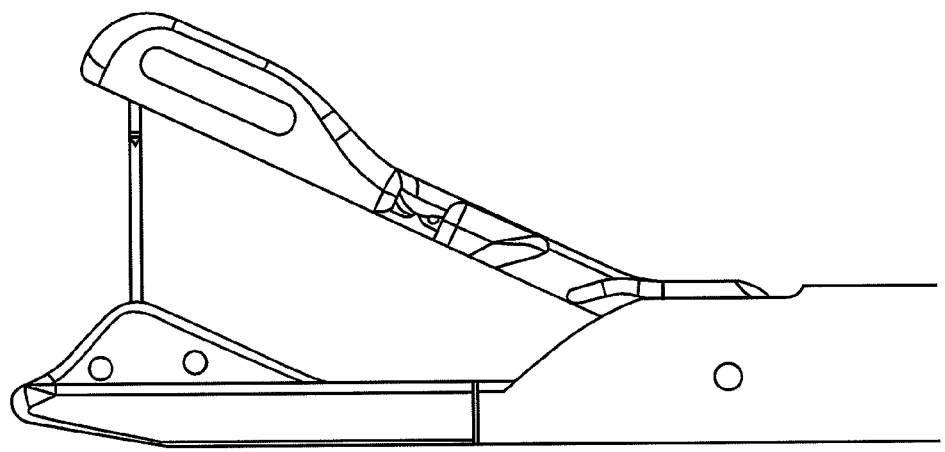

FIGS. 18A-18C illustrate another variation of a suture passer. In FIG. 18A, the second jaw member is not retracted proximally, and the first and second jaw members are clamped together. The first jaw member may be opened as shown in FIG. 18B, and the tissue penetrator may be extended across the distal-facing opening, as shown in FIG. 18C.

Methods of Use

In general, the devices described herein may be used to suture any appropriate tissue. These devices are particularly well suited for passing a suture in a minimally invasive procedure to reach difficult to access regions. Examples of the use of these devices are provided below, and illustrated in FIGS. 19A to 31F.

Figure 19C:
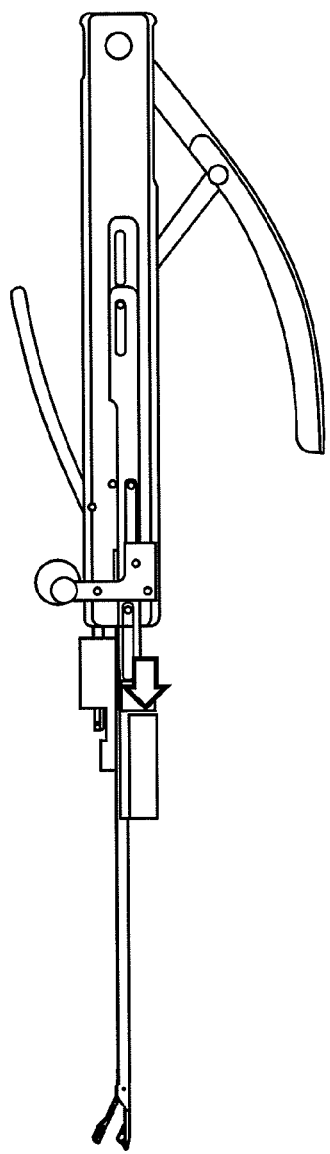

The general operation of one variation of a dual deployment suture passer is illustrated in FIGS. 19A-19F. The clamping/sliding suture passer illustrated in FIG. 19A includes a handle such as the one shown in FIG. 17A, above. Before use, a suture may be loaded on the first jaw member of the device. For example, a loop of suture may be loaded onto the first jaw member. The free ends of the suture may be coupled to a suture control element such as a tensioning screw, as shown in FIG. 19A. For example, the two free ends may be cinched onto a tensioner screw. The suture passer may be loaded outside of the body by the user, or it may be pre-loaded. Once loaded, the suture passer may be inserted into the body near the target tissue. For example, the device may be inserted into the body through a cannula. As shown in FIG. 19A, the second (lower) jaw member may be fully retracted proximally, and the upper jaw may be clamped down fully so that it is in-line with (straight) relative to the elongate member; the first jaw member may be locked in this position for insertion, or it may be moved or dynamically adjusted as it is inserted.

Thereafter, the device may be positioned relative to the target tissue. For example, the first jaw member may be positioned adjacent to the target tissue. As shown in FIG. 19B, the device may then be positioned and the clamp trigger adjusted or released.

Once the tissue is adjacent to the first jaw member, the second jaw member may be extended to surround a target tissue, as shown in FIG. 19C. In this example, the control for the second jaw member (the lower jaw lock) may be actuated to slide the lower jaw member distally, forming the distal-facing opening, and surrounding (at least partially) the target tissue to be sutured. As shown in FIG. 19C, this may be achieved by sliding in and locking the lower jaw with the lower jaw handle by releasing the lower jaw screw lock and sliding the lower jaw into position. The lower (second) jaw may then be locked in a fully extended position.

Figure 19D:
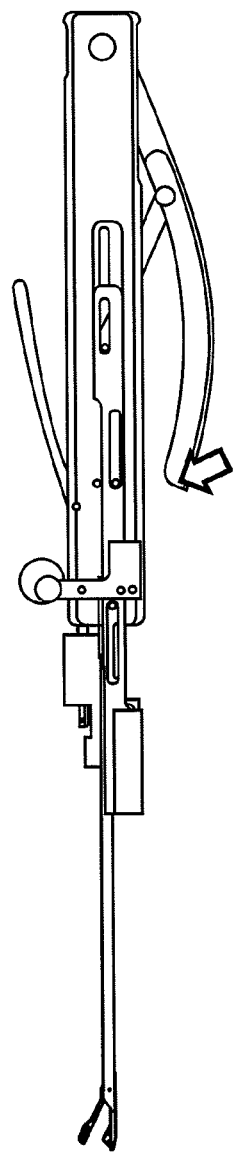
Figure 21B:
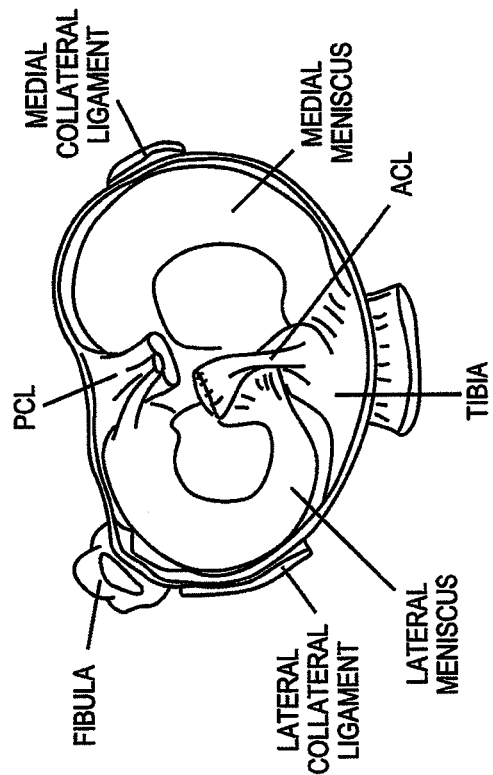
FIGS. 21A and 21B illustrate the anatomy of the meniscus.
Figure 21A:
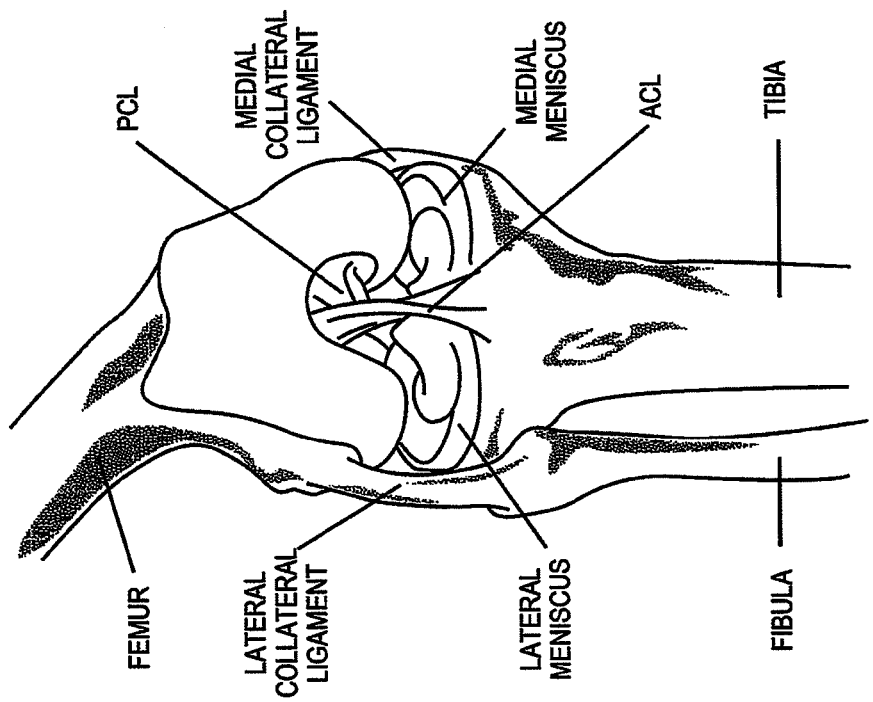
Figure 22:
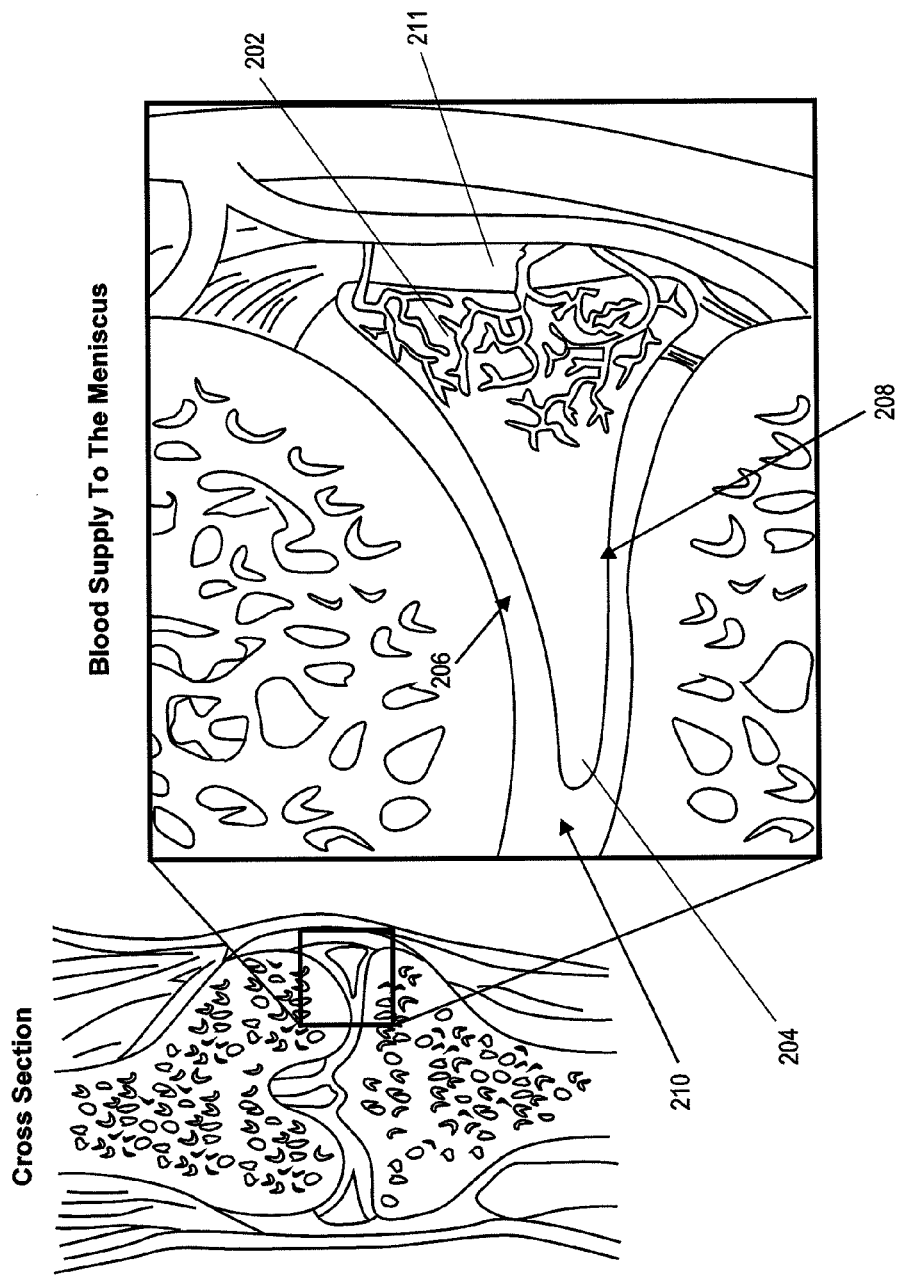
FIG. 22 illustrates the anatomy of the meniscus, including the capsule and associated vascular tissue.
Figure 23:
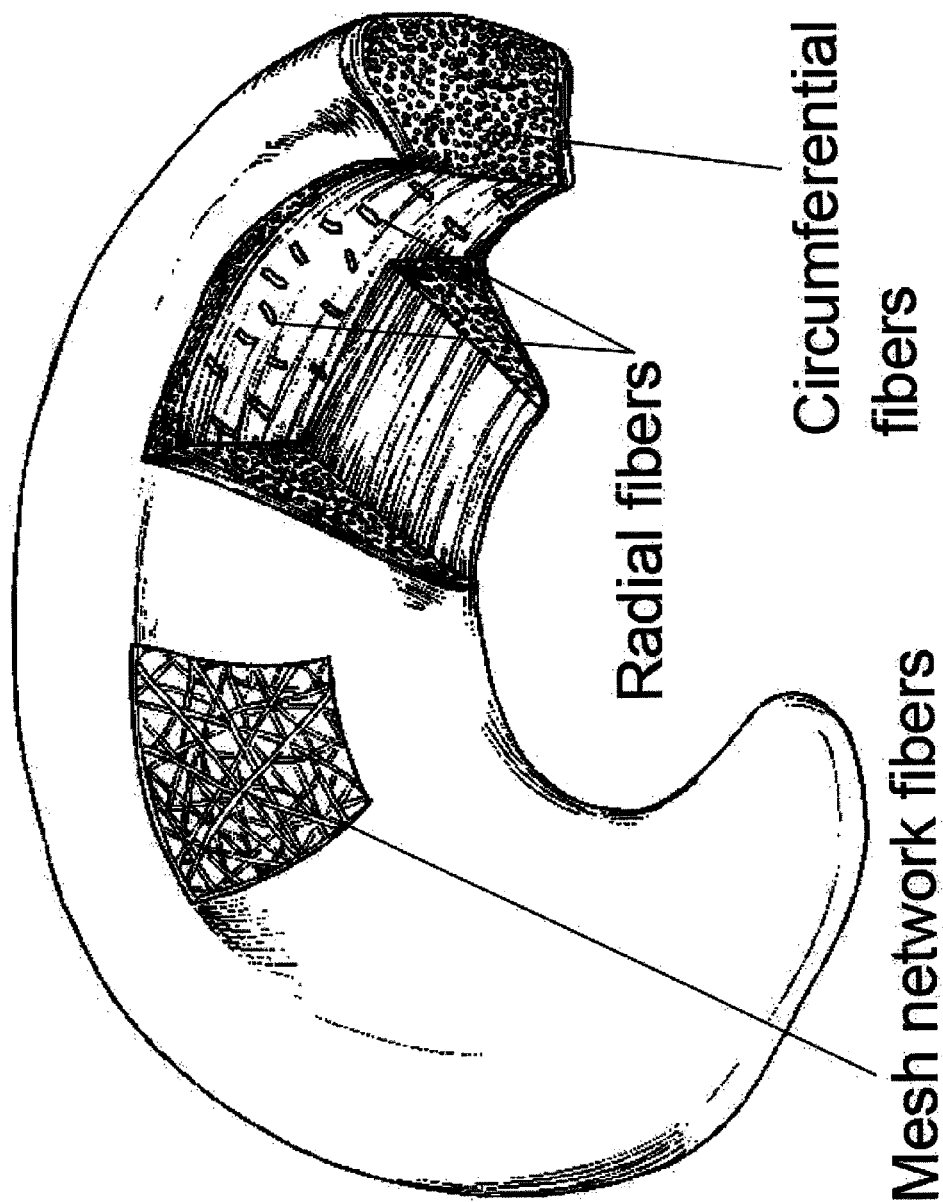
FIG. 23 illustrates the structure of a meniscus.

The upper (first) jaw member may be adjusted to clamp or hold the target tissue securely between the upper and lower (first and second) jaw members, as illustrated in FIG. 19D. Thereafter, the tissue penetrator may be actuated (e.g., by squeezing the needle trigger) to extend from within the lower jaw member, through the tissue between the first and second lower jaw members, and across to the upper jaw. To engage a suture held within the suture engagement region in the upper jaw. The tissue penetrator may then pick up the suture from the upper jaw and pull it back down through the tissue, as shown in FIGS. 19D and 19E.

Once the suture has been hooked, the tissue penetrator may be retraced back into the second jaw member (in this example), as shown in FIG. 19F, and the lower jaw member may be retraced proximally, in the reverse to the process described above, so that the suture passer, which having passed the suture successfully, may be withdrawn from the patient.

FIGS. 20A-20B show a generic version of a dual deployment suture passer. FIG. 20A shows a suture passer having a second jaw member in a retracted state; FIG. 20B shows the same suture passer with the lower jaw in an extended state. This generic schematic of a dual deployment (e.g., clamping/sliding) suture passer may be used to illustrate operation of the device in different tissues.

Any of the devices described herein may be used to suture and treat a torn meniscus of the knee. For example, in FIGS. 25A-25H a torn meniscus 2503 is repaired using the device as discussed above. In FIG. 25A the suture passer 2505 is inserted into the knee with just the first jaw member extended. The jaw member can easily fit between the femur and tibia of the knee to approach the meniscus 2501. The first jaw member can then be slid between the superior surface of the meniscus and the femur (as shown in FIG. 25B). The angle of the first jaw member may be dynamically adjusted as the suture passer is inserted to best match the tissue. This procedure may be observed arthroscopically. Thereafter, the second jaw member 2507 may be advanced under the meniscus between the inferior surface of the meniscus and the tibia, until the second jaw member is fully extend and the target tissue, including the meniscal tear 2503 is surrounded within the jaws of the device as shown in FIG. 25C.

The meniscus tissue may then be clamped between the first and second jaw members, and the tissue penetrator may be extended across the tissue, as shown in FIG. 25D. The arrow indicates the direction of the tissue penetrator from the lower (second) jaw member, through the meniscus and into the upper (first) jaw member. The tissue penetrator may then engage the suture held in the first jaw member. The tissue penetrator is prevented (e.g., by a limiter) from extending beyond the upper jaw member, and may then be retracted, as shown in FIG. 25E, by withdrawing the tissue penetrator back down through the meniscus and into the lower (second) jaw member, pulling the suture loop with it. In FIG. 25F, the suture has been completely drawn through the meniscus and the tissue penetrator completely retracted. Thereafter the lower jaw member may also be withdrawn by axially retracting it proximally, as shown in FIG. 25G. The suture passer may then be withdrawn from the meniscus, as shown in FIG. 25H. The looped suture may be pulled so that one free end of the suture is pulled through the meniscus (leaving a single suture length, rather than a loop of suture passing though the meniscus). The suture may then be knotted.

Figure 26B:
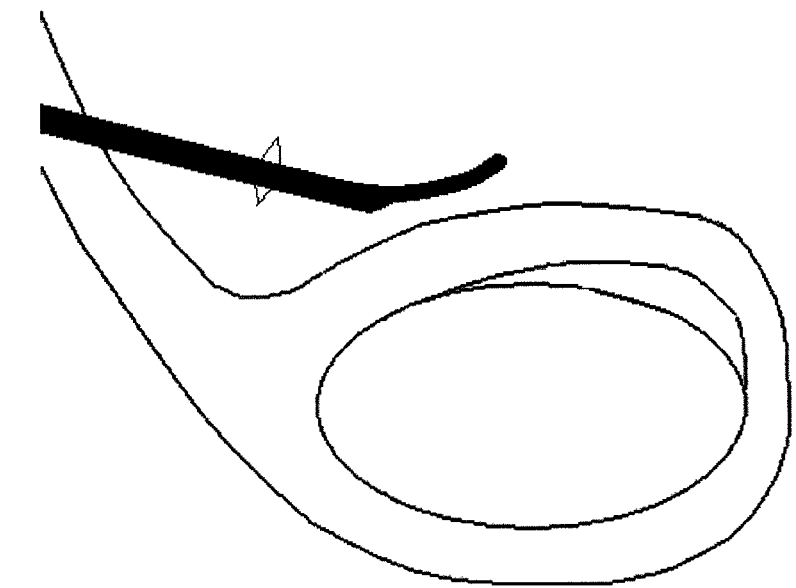
FIGS. 26A-26H illustrate the use of a dual deployment suture passer to suture a labral tear.
Figure 26A:
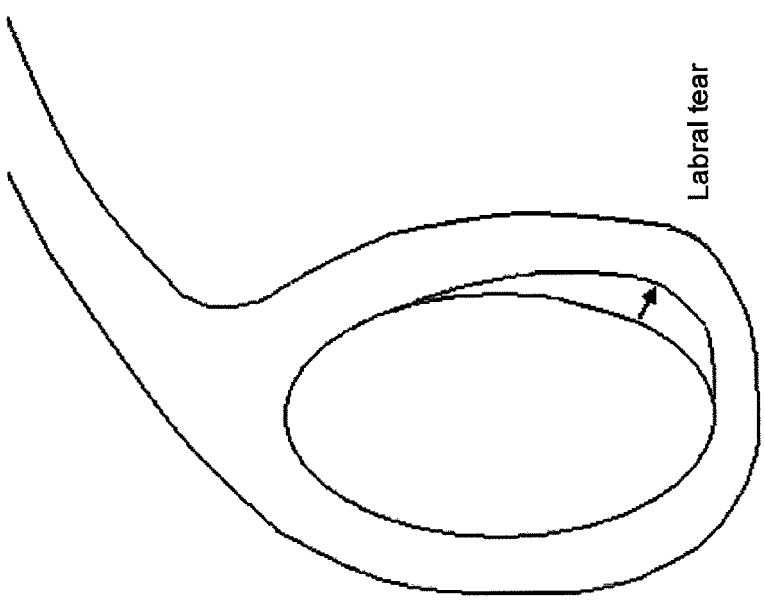
Figure 26D:
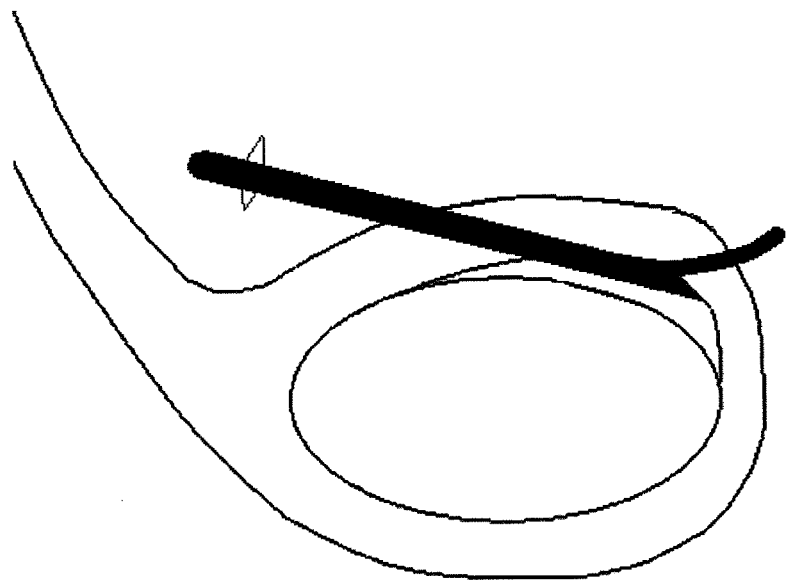
Figure 26C:
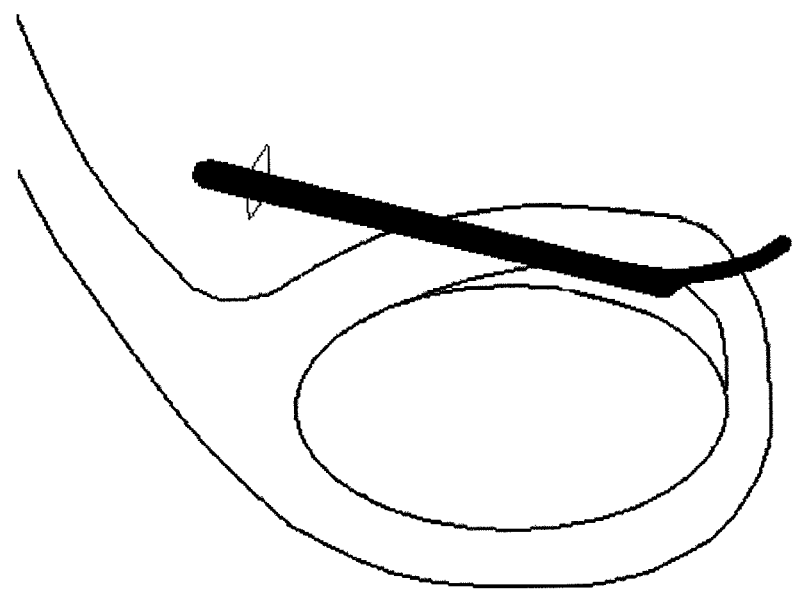
Figure 26F:
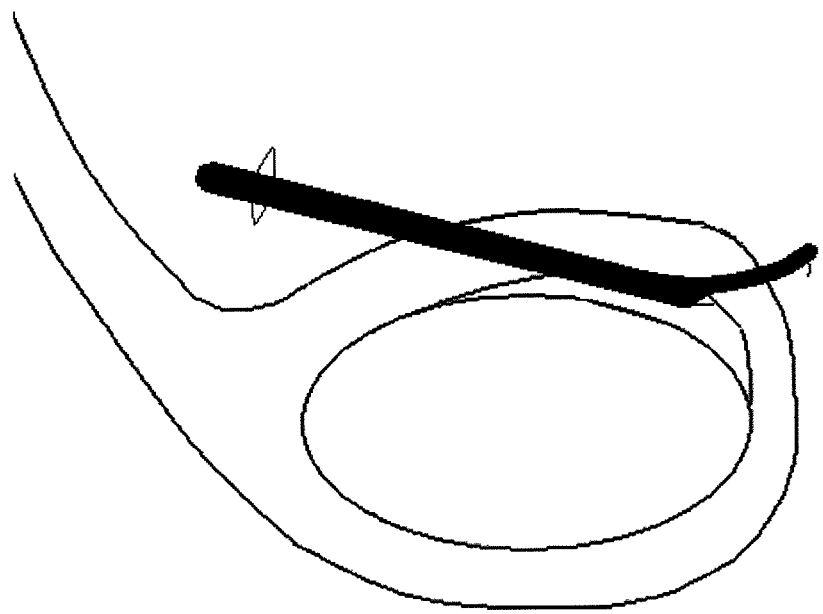
Figure 26E:
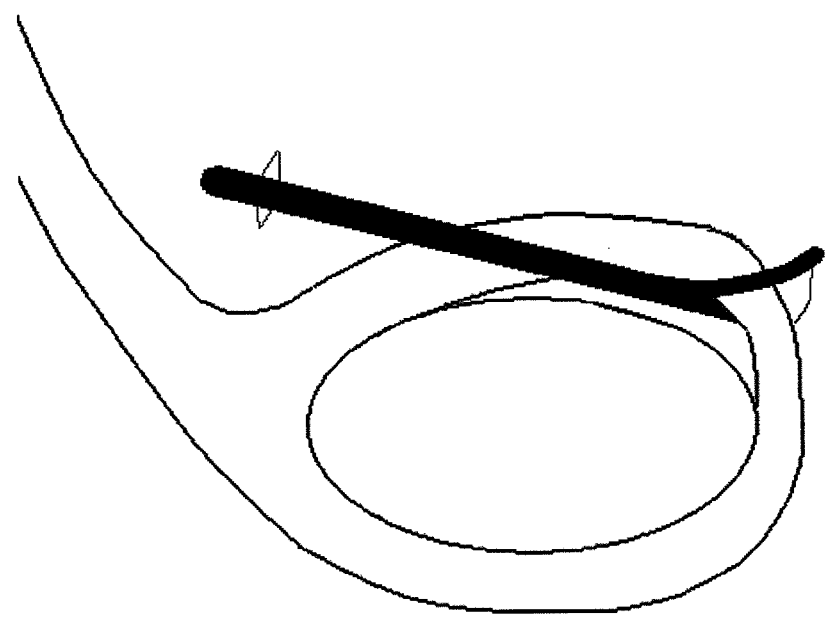
Figure 26H:
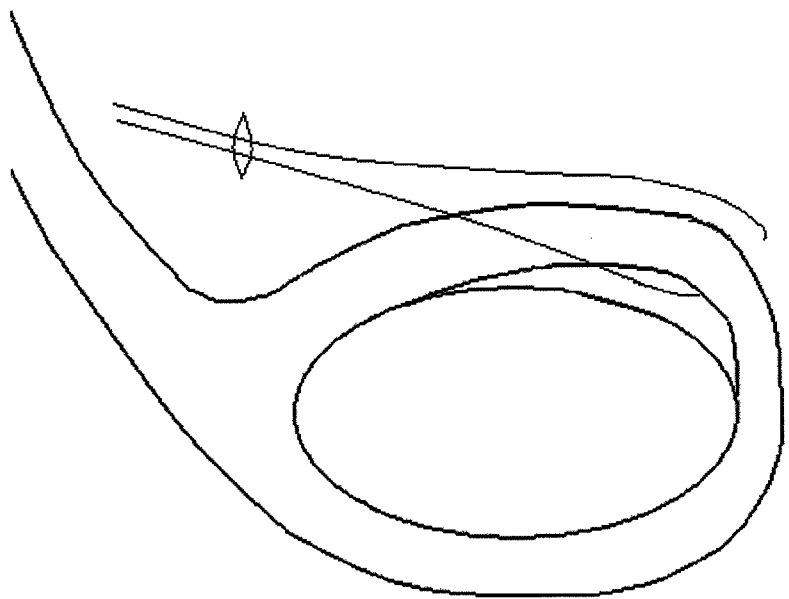
Figure 26G:
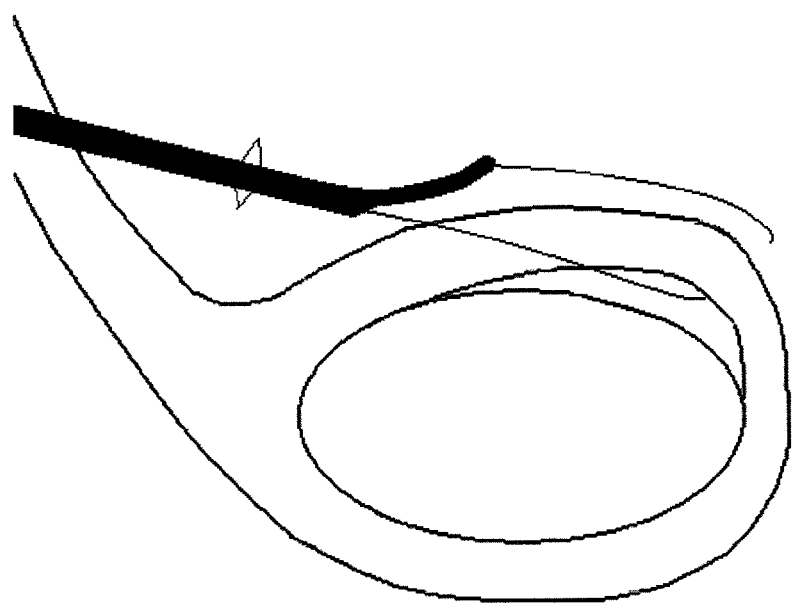

FIGS. 26A-26H illustrate another variation of a method of using the suture passer devices described herein to treat a patient. In this example, the method is used to treat a Bankart tear, an anterior inferior (or posterior inferior) labral tear. FIG. 26A illustrates the labral tear. In FIG. 26B the suture passer is inserted into the shoulder and the first jaw member is positioned (by dynamically adjusting the angle of the first jaw member) adjacent to the torn tissue, as shown in FIG. 26C. In FIG. 26C, the first jaw member is placed over the labrum and the anterior-inferior capsule. The lower (second) jaw member may then be axially extended so that the jaws now encompass the labro-capsular region, as shown in FIG. 26D. The first jaw may be adjusted to clamp the target tissue securely between the jaws and the tissue penetrator may be extended to pass a suture between the jaws, as shown in FIG. 26E. The lower (second) jaw member may then be retracted, and the device may be removed, as shown in FIG. 26G. A knot or tie may then be slid over the suture ends to tide off the suture as shown in FIG. 26H.

Figure 27A:
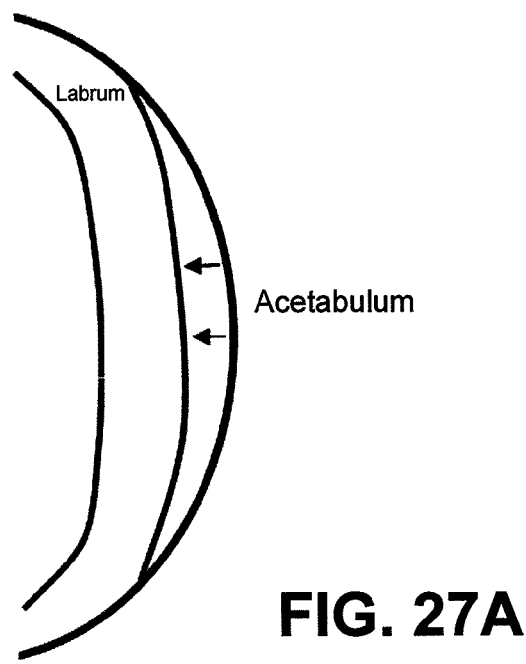
FIGS. 27A-27G illustrate the use of a dual deployment suture passer to repair a hip labrum.
Figure 27B:
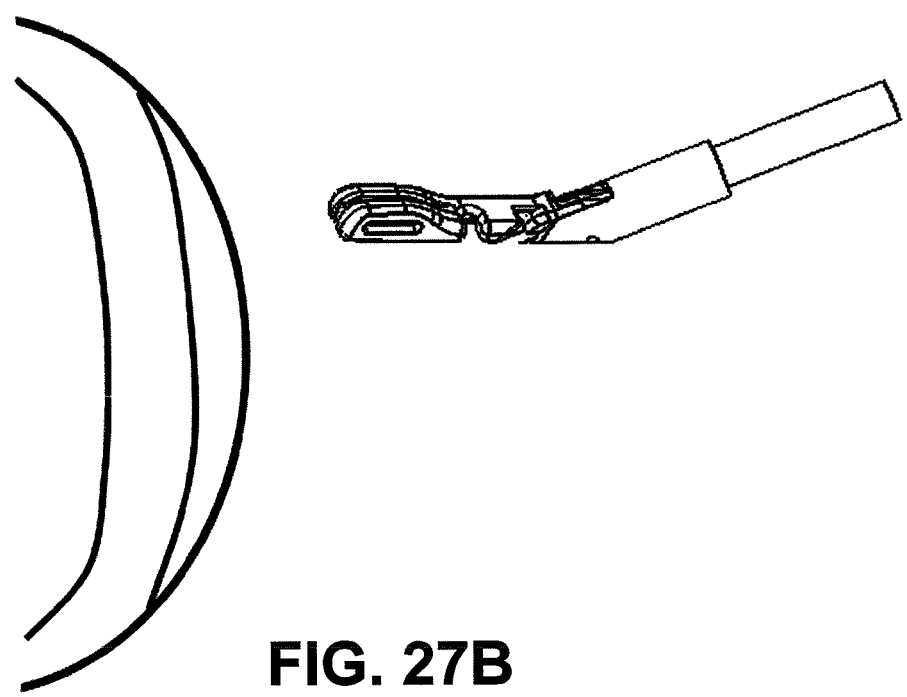
Figure 27C:
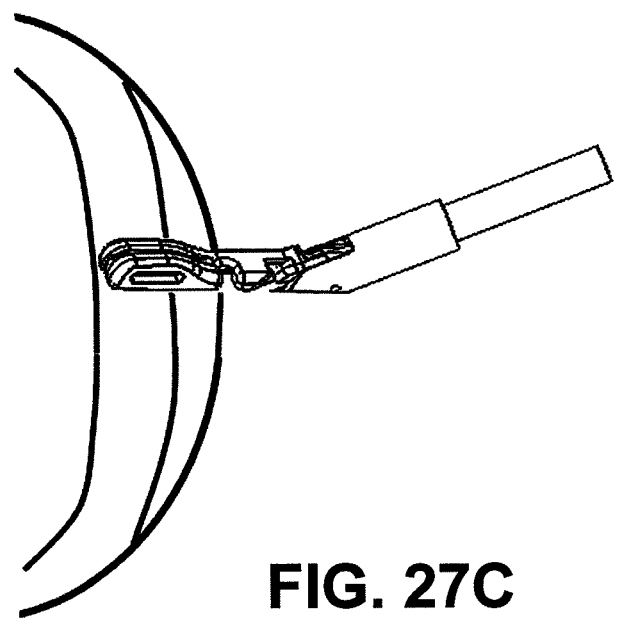
Figure 27D:
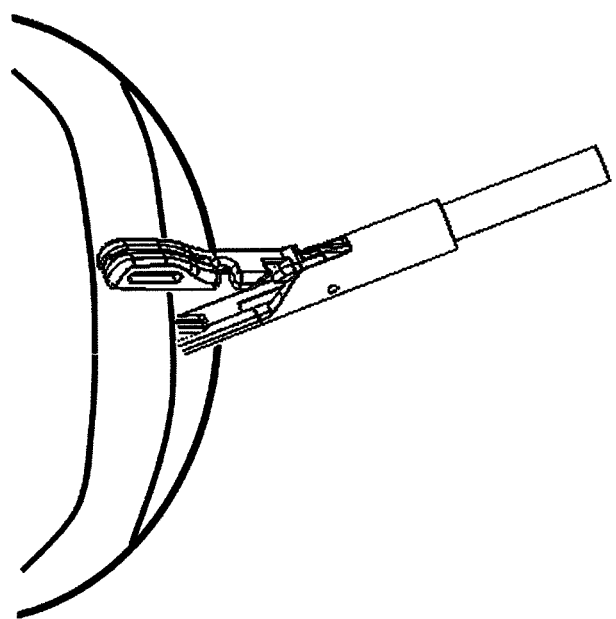
Figure 27E:
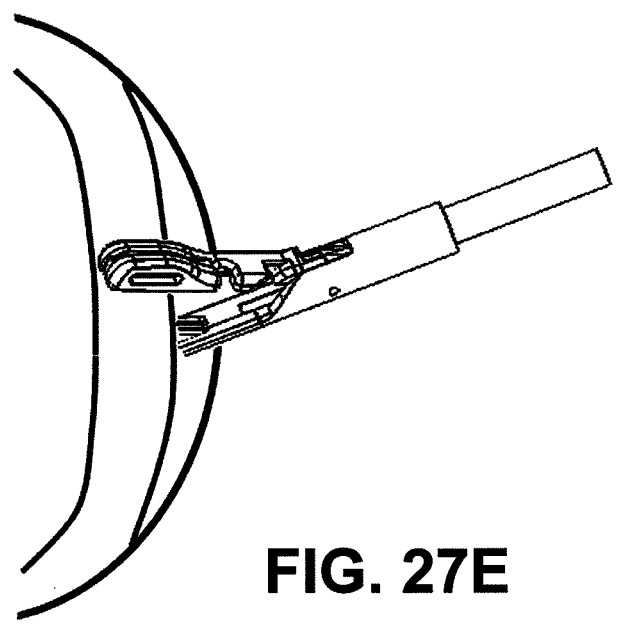
Figure 27F:
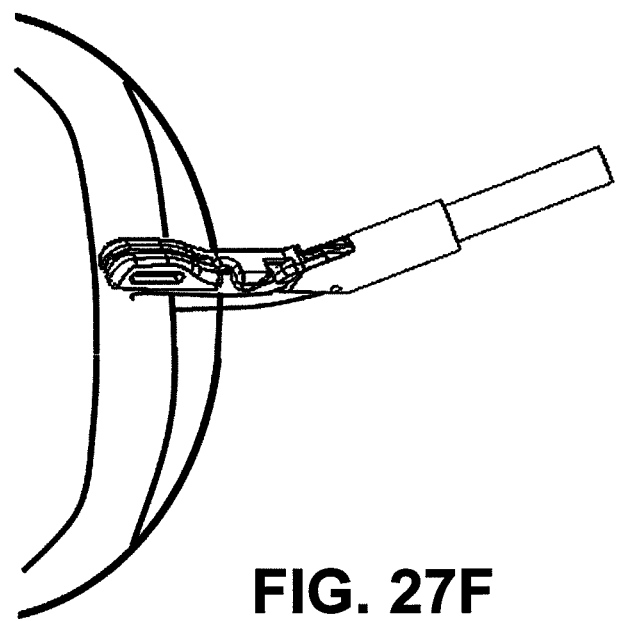
Figure 27G:
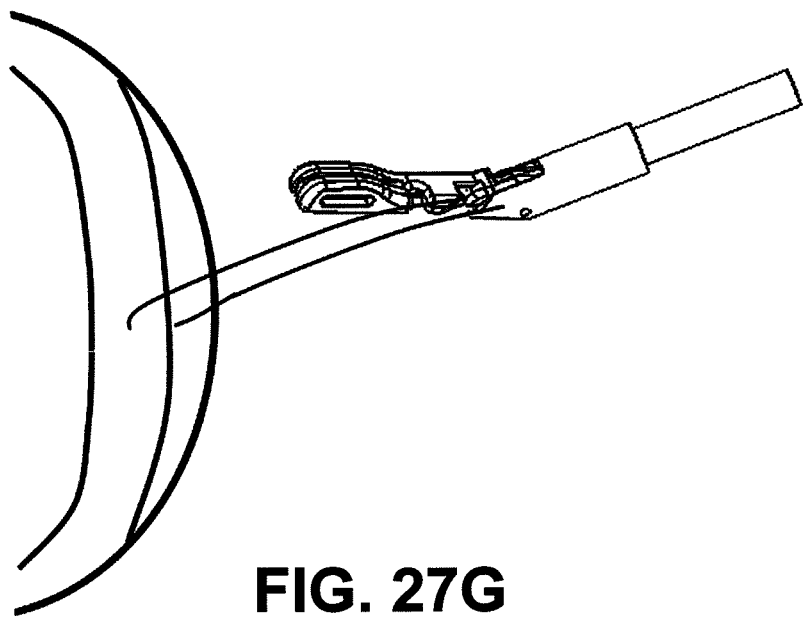

The suture passer devices and methods describe herein may also be used to repair a hip labrum, as illustrated in FIGS. 27A-27G. In FIG. 27A-27B, the hip labrum may be approached by the suture passer having the second jaw member retracted and the first jaw member extended distally. The angle of the first jaw member may be dynamically adjusted to help pace the suture passer near the labrum to be sutured, as shown in FIG. 27C. In FIG. 27D, the second jaw member may be axially extended from a proximal position to slide beneath the labrum and form a distal-facing opening so that the first and second jaw members surround the labrum tissue as shown in FIG. 27D. In FIG. 27E the tissue penetrator may then be extended across the distal-facing opening and through the tissue to grab (or in some variations drop off) a suture in the suture engagement region of the opposite jaw member. The tissue penetrator can then be retracted, and the second jaw member can also be retracted proximally, as shown in FIG. 27F. Finally, the device can be withdrawn from the tissue, as shown in FIG. 27G.

In any of the methods described herein the device may be controlled from the proximal end by a handle such as those illustrated above (e.g., FIGS. 17A and 17B). The device may be controlled using a single hand.

Figure 30C:
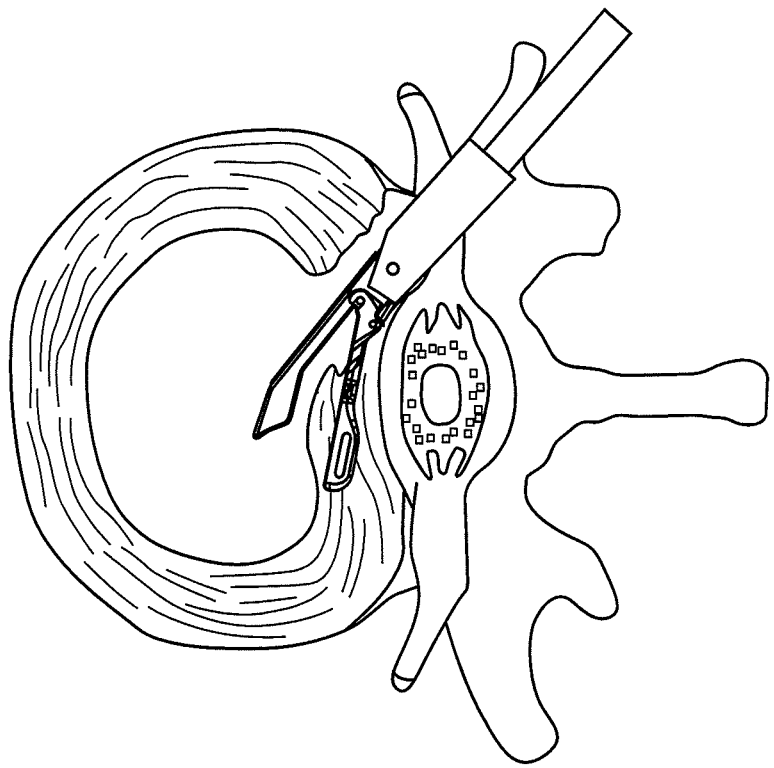
Figure 30B:
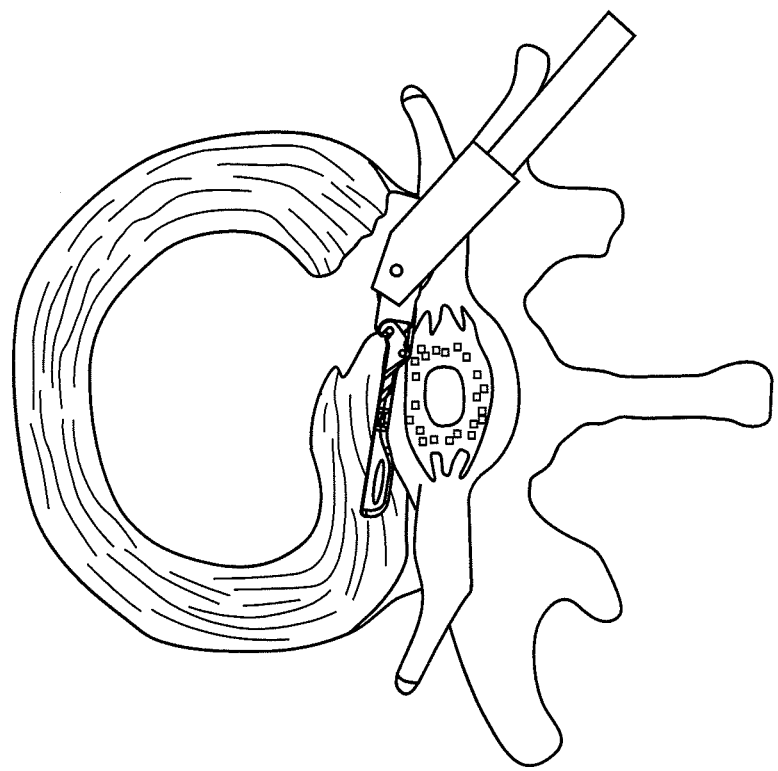
Figure 30D:
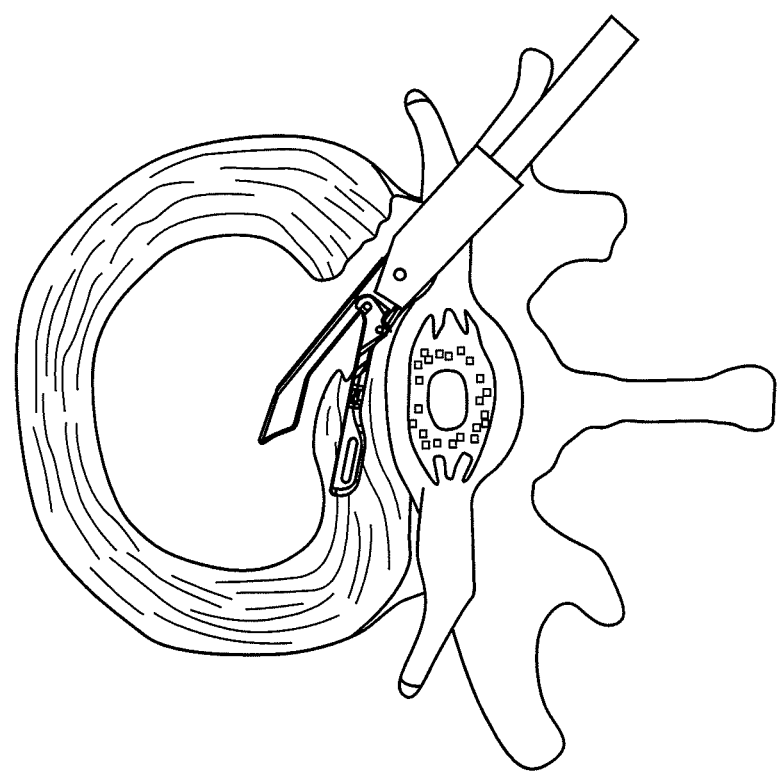
Figure 30E:
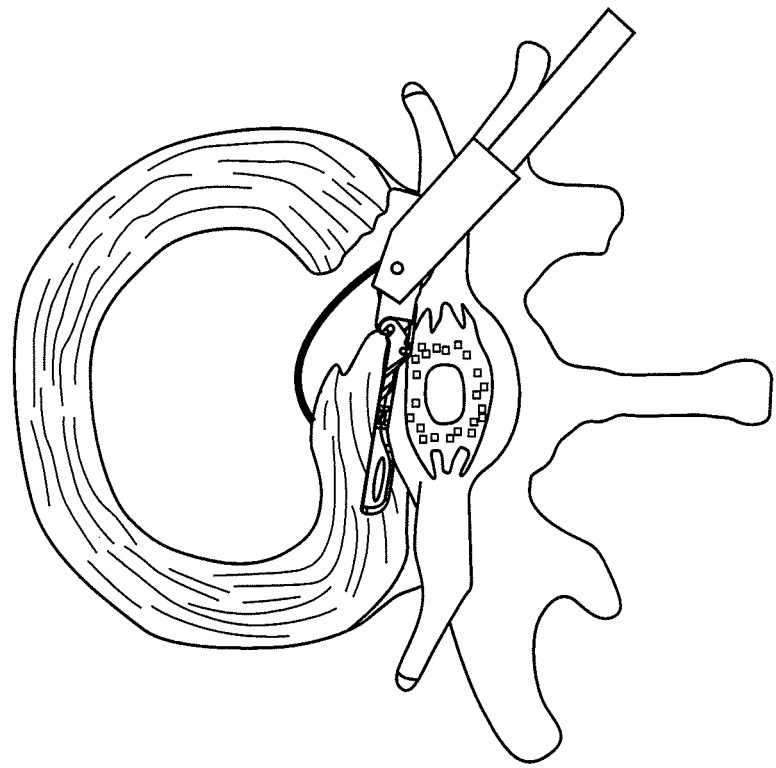
Figure 30F:
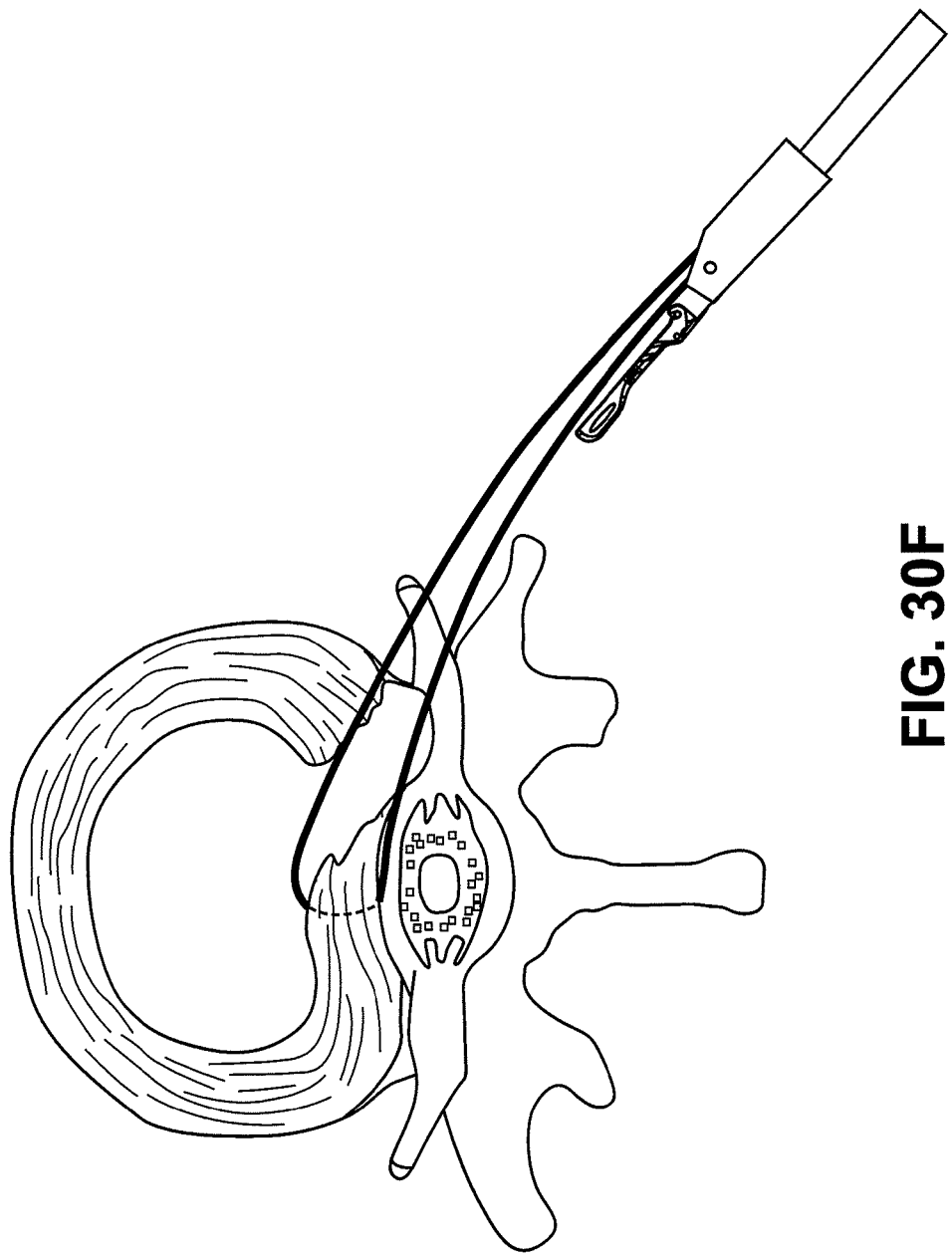

FIGS. 28, 29, 30A-30F and 31A-31F illustrate the use of a suture passer device such as the one illustrate herein to repair spinal tissue. For example, FIG. 28 shows a normal disc of a spine (a schematic illustration of a section through the spine is shown). In contrast, FIG. 29 shows a herniated disc. Traditionally this region has been difficult to access and thus difficult to suture. One variation of a device as described herein may be used to suture the disk annulus. For example, in FIG. 29A shows a suture passer as descried herein approaching the herniated disc. The angle of the first jaw member may be dynamically adjusted to help position the first jaw member adjacent to the tissue (e.g., the annuls) to be sutured. Once in position, as shown in FIG. 30B, the second jaw member may be extended so that the tissue to be treated is between the jaws, as shown in FIG. 30C. Thereafter the tissue penetrator may be extended across the jaws and through the tissue either to push a suture to the opposite side, or in some variations, to pull the suture from the opposite side back through the tissue. The second jaw member may then be retracted and the entire device withdrawn from the disc region, as shown in FIG. 30F, leaving the suture behind.

In general, a suture may be passed from the first jaw member to the second jaw member or vice versa. Further, the tissue penetrator may be configured to push the suture through the tissue or it may be configured to pull the suture through the tissue; the suture engagement region on the opposite side of the jaw from that housing the tissue penetrator may be adapted for either receiving a suture (e.g., having a clamping region or gripping region, a hook, or the like) or for passing on a suture (e.g., holding the suture in position where it may be grabbed by the tissue penetrator). In addition, the tissue penetrator may be in either the second jaw member (as primarily illustrated above) or it may be in the first jaw member; the appropriate engagement region may be present on the opposite jaw as well.

Figure 31A:
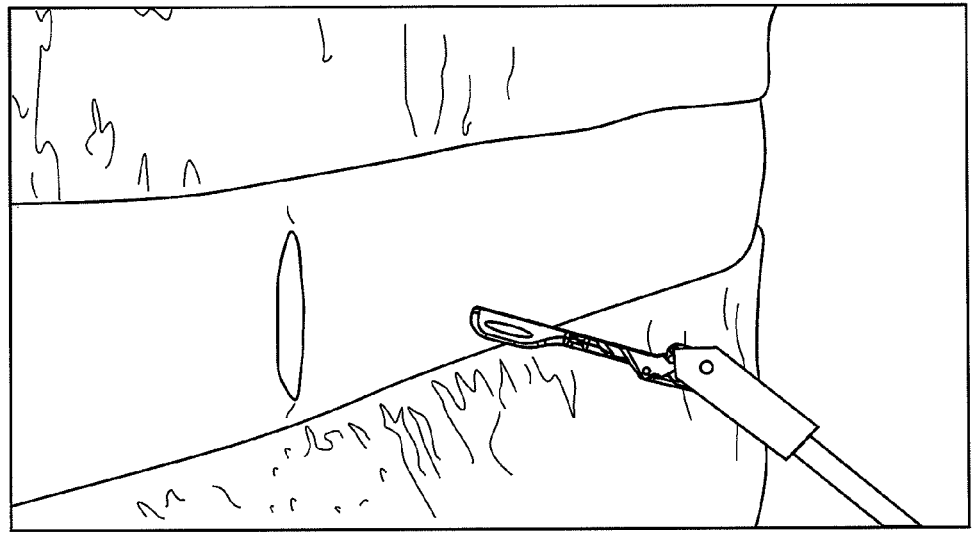
FIGS. 31A-31F illustrate another example of using a dual deployment suture passer to repair a spinal region.
Figure 31B:
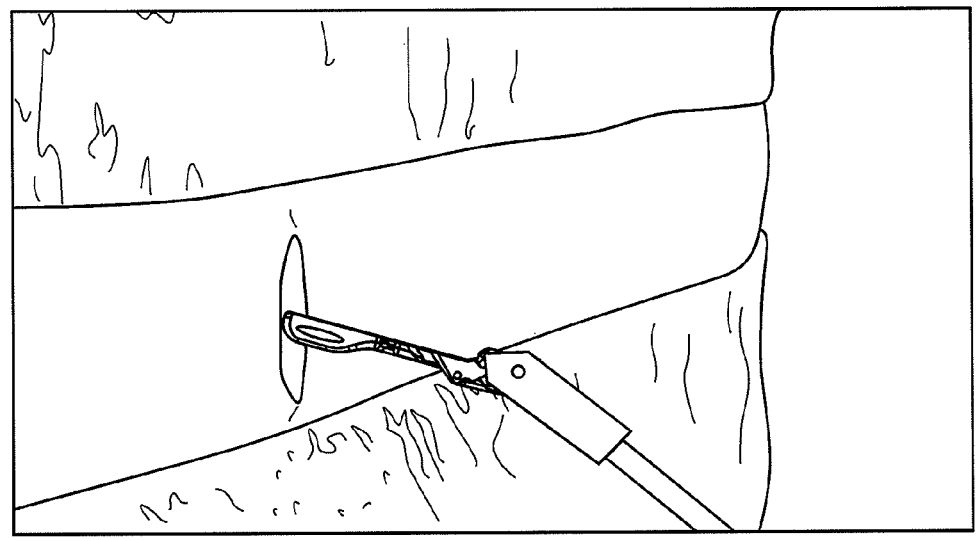
Figure 31C:
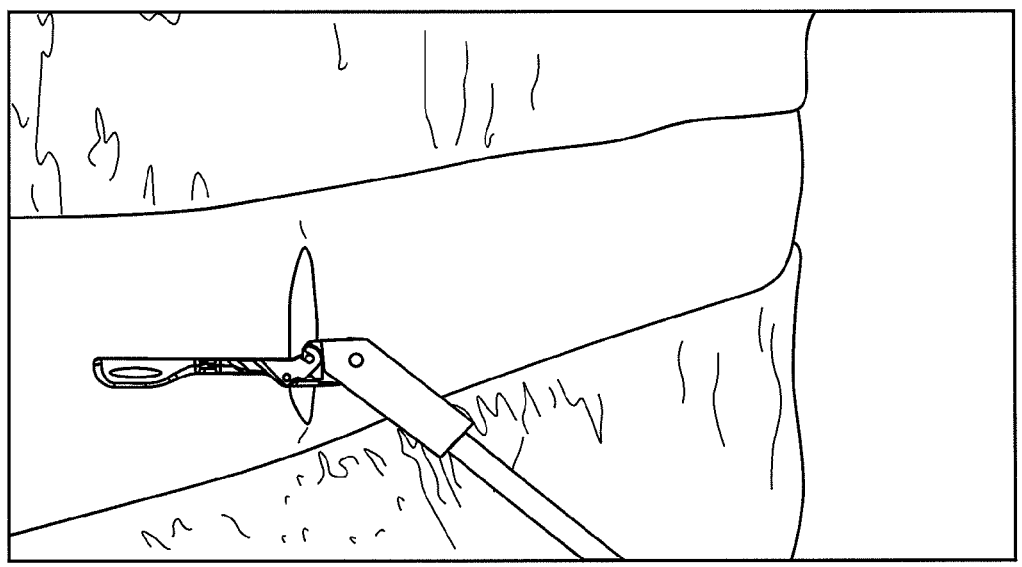
Figure 31D:
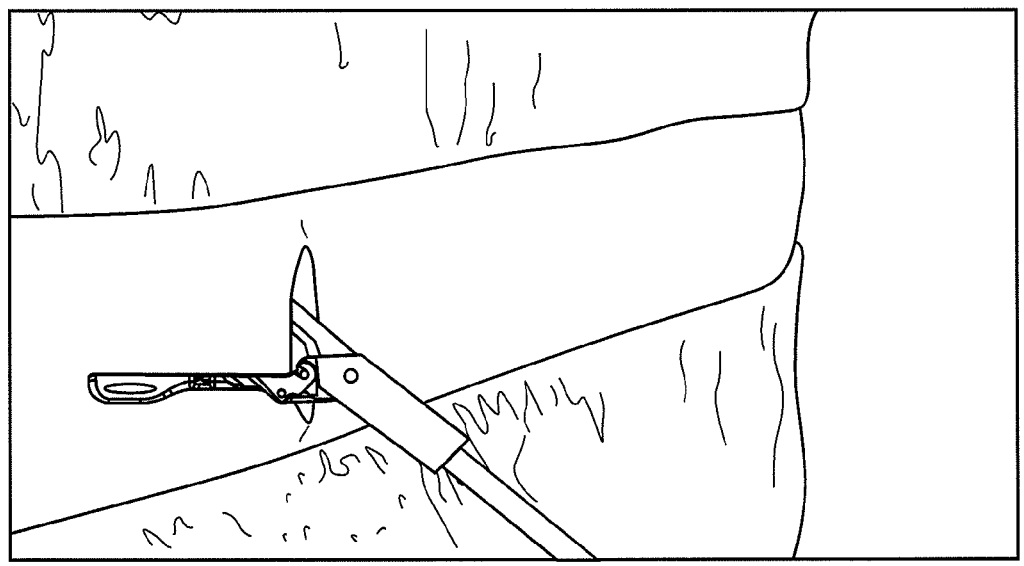
Figure 31E:
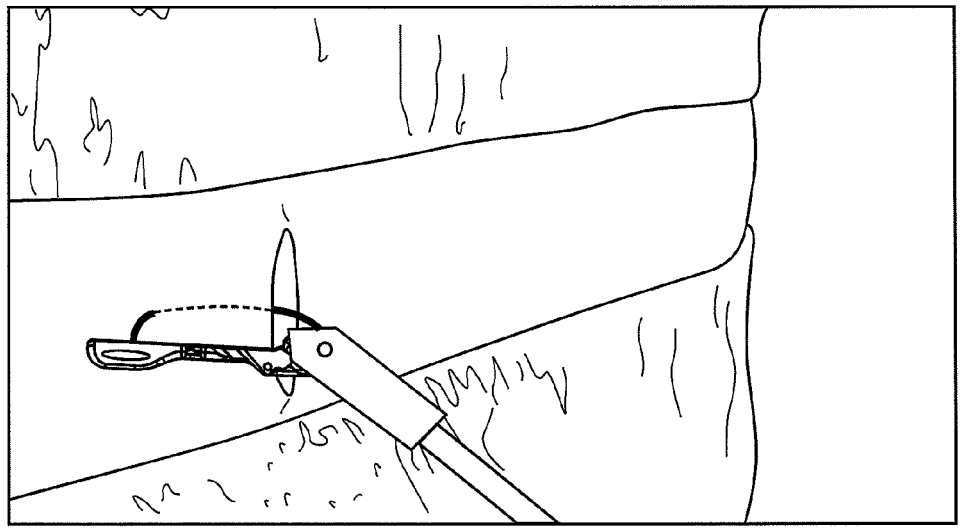
Figure 31F:
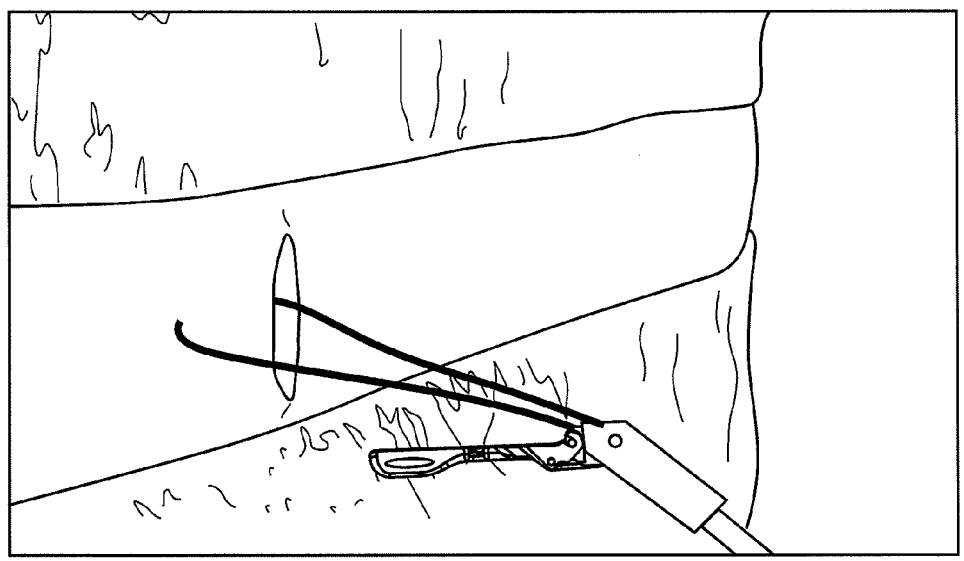

FIGS. 31A-31F show another view of the method for suturing an annulus of a disc of a spine. For example, in FIGS. 31A to 31C, the suture passer including an extended first jaw member approaches the torn tissue to be sutured. In FIG. 31D the second jaw member is axially extended on the opposite side of the tissue to be sutured, and the tissue penetrator is extended to pass the suture through the tissue. In FIG. 31 the tissue penetrator has been retracted and the second jaw member has also been retracted, so that the suturing device may be withdrawn while pulling the suture through the tissue, as shown in FIG. 31F.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the invention.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A suture passer device comprising:
   an elongate body having a proximal end region and a distal end region;
   a first jaw member extending from the distal end region of the elongate body and configured for angular movement relative to the elongate body;
   a second jaw member configured to extend axially relative to the elongate body, the second jaw configured to form an opening with the first jaw member when the second jaw member is axially extended, wherein the second jaw member is configured to move independently of the first jaw member;
   a tissue penetrator deployably held with a distal tip retracted entirely within either the first or second jaw member and configured to pass a suture between the first and second jaw members, wherein the tissue penetrator is deflected as it extends from within either the first or second jaw member to extend between the first and second jaw members when the first and second jaw members form the opening, and
   a lock configured to prevent the tissue penetrator from extending between or beyond the first and second jaw members until the second jaw member is extended.

2. The device of claim 1, wherein the tissue penetrator is configured to extend and retract between the first and second jaw members without extending substantially beyond a lateral side of the first or second jaw members opposite the opening.

3. The device of claim 1, wherein the second jaw member is configured to move axially by extending distally or retracting proximally from within the distal end region of the elongate body.

4. The device of claim 1, wherein the opening formed by extending the second jaw member comprises a distal-facing opening.

5. The device of claim 1, further comprising a suture engagement region near the distal tip of the tissue penetrator, the suture engagement region configured to couple with a suture.

6. The device of claim 1, further comprising a travel limiter configured to prevent the tissue penetrator from extending substantially beyond a lateral side of the first or second jaw members opposite the opening.

7. The device of claim 1, further comprising a movement limiter configured to limit the movement of the tissue penetrator based on a position of the first jaw member, the second jaw member or both the first and second jaw members, relative to the elongate body.

8. The device of claim 1, further comprising a second jaw holdfast configured to hold the second jaw member in an axial position relative to the elongate body.

9. The device of claim 1, further comprising a first jaw holdfast configured to hold the first jaw member in an angular position relative to the elongate body.

10. The device of claim 1, further comprising a first control for controlling the angular position of the first jaw member relative to the elongate body and a second control for controlling the axial position of the second jaw member relative to the elongate body.

11. The device of claim 1, further comprising an indicator for indicating when the second jaw is in a predetermined axially extended position relative to the elongate body.

12. The device of claim 1, further comprising a proximal handle having controls for controlling at least one of the angular movement of the first jaw member, the axial movement of the second jaw member or the extension and retraction of the tissue penetrator.

13. The device of claim 1, wherein the tissue penetrator is housed and extends from within the second jaw member.

14. The device of claim 1, wherein the opening between the first and second jaws is an angular opening.

15. The device of claim 1, wherein the second jaw member is configured to retract into the distal end region of the elongate body.

16. The device of claim 1, wherein the second jaw member is configured to retract into the distal end region of the elongate body so that most or all of the second jaw member is held proximal to the distal end of the elongate body.

17. The device of claim 1, wherein the lock is configured to prevent the tissue penetrator from extending between or beyond the first and second jaw members until the second jaw member is fully extended.

18. The device of claim 1, wherein the lock is configured to prevent the tissue penetrator from extending between or beyond the first and second jaw members until the second jaw member is extended in a predetermined axial position.

19. The device of claim 1, further comprising a tactile or aural indicator that indicates when the second jaw is fully extended.

20. A suture passer device comprising:
    an elongate body having a proximal end region and a distal end region;
    a first jaw member extending from the distal end region of the elongate body and configured for angular movement relative to the elongate body;
    a second jaw member configured to extend distally or retract proximally from within the distal end region of the elongate body;
    a tissue penetrator configured to pass a suture between the first and second jaws and further configured to extend and retract between the first and second jaw members and to deflect against a deflection region as it extends from within either the first or second jaw member when the second jaw member is extended distally to form a distal-facing opening with the first jaw member, and
    a lock configured to prevent the tissue penetrator from extending between or beyond the first and second jaw members until the second jaw member is extended.

21. The device of claim 20, further comprising a suture engagement region near a distal tip of the tissue penetrator, the suture engagement region configured to couple with a suture.

22. The device of claim 20, further comprising a movement limiter configured to limit the movement of the tissue penetrator based on a position of the first jaw member, the second jaw member or both the first and second jaw members.

23. The device of claim 20, further comprising a second jaw holdfast configured to hold the second jaw member in an axial position relative to the elongate body.

24. The device of claim 20, further comprising a first jaw holdfast configured to hold the first jaw member in an angular position relative to the elongate body.

25. The device of claim 20, further comprising a first control for controlling the angular position of the first jaw member relative to the elongate body and a second control for controlling the axial position of the second jaw member relative to the elongate body.

26. The device of claim 20, further comprising a travel limiter preventing the tissue penetrator from extending beyond a lateral side of the first or second jaw members opposite the distal-facing opening.

27. The device of claim 20, further comprising a proximal handle having controls for controlling at least one of the angular movement of the first jaw member, the axial movement of the second jaw member and the extension and retraction of the tissue penetrator.

28. The device of claim 20, wherein the tissue penetrator is housed and extends from within the second jaw member.

29. The device of claim 20, wherein the second jaw member is configured to retract into the distal end region of the elongate body so that most or all of the second jaw member is held proximal to the distal end of the elongate body.

* * * * *